United States Patent
Cramer et al.

(10) Patent No.: US 6,240,374 B1
(45) Date of Patent: May 29, 2001

(54) FURTHER METHOD OF CREATING AND RAPIDLY SEARCHING A VIRTUAL LIBRARY OF POTENTIAL MOLECULES USING VALIDATED MOLECULAR STRUCTURAL DESCRIPTORS

(75) Inventors: Richard D. Cramer, O'Fallon; David E. Patterson, St. Louis, both of MO (US)

(73) Assignee: Tripos, Inc., St. Louis, MO (US)

( * ) Notice: Subject to any disclaimer, the term of this patent is extended or adjusted under 35 U.S.C. 154(b) by 0 days.

(21) Appl. No.: 08/903,217

(22) Filed: Jul. 20, 1997

Related U.S. Application Data

(63) Continuation-in-part of application No. 08/657,147, filed on Jun. 3, 1996, now abandoned, which is a continuation-in-part of application No. 08/592,132, filed on Jan. 26, 1996.

(51) Int. Cl.[7] .............. G06F 1/00; G06F 3/00; G06F 7/00; G06F 7/06
(52) U.S. Cl. ................. 703/11; 703/12; 435/7.1; 435/DIG. 51
(58) Field of Search ............... 702/27, 19, 22; 435/7.1, DIG. 51; 364/496; 703/11, 12

(56) References Cited

U.S. PATENT DOCUMENTS

| | | | |
|---|---|---|---|
| 4,642,762 | 2/1987 | Fisanich | 364/300 |
| 4,811,217 | 3/1989 | Tokizane et al. | 364/300 |
| 5,025,388 | * 6/1991 | Cramer, III et al. | 364/496 |
| 5,056,035 | 10/1991 | Fujita | 364/497 |
| 5,157,736 | 10/1992 | Boyer et al. | 382/10 |
| 5,270,170 | 12/1993 | Schatz et al. | 435/737 |
| 5,307,287 | 4/1994 | Cramer, III et al. | 364/496 |
| 5,345,516 | 9/1994 | Boyer et al. | 382/10 |
| 5,386,507 | 1/1995 | Teig et al. | 395/161 |
| 5,418,944 | 5/1995 | Dipace et al. | 395/600 |
| 5,424,963 | 6/1995 | Turner et al. | 364/578 |
| 5,434,796 | 7/1995 | Weininger | 364/496 |
| 5,463,564 | 10/1995 | Agrafiotis et al. | 364/496 |
| 5,500,807 | 3/1996 | Lavin et al. | 364/496 |
| 5,526,281 | 6/1996 | Chapman et al. | 364/496 |
| 5,555,366 | 9/1996 | Teig et al. | 395/161 |
| 5,574,656 | 11/1996 | Agrafiotis et al. | 364/500 |
| 5,577,239 | 11/1996 | Moore et al. | 395/603 |
| 5,583,973 | 12/1996 | Delisi et al. | 395/118 |
| 5,619,421 | 4/1997 | Venkataraman et al. | 364/496 |
| 5,703,792 | * 12/1997 | Chapman | 364/496 |
| 5,752,019 | 5/1998 | Rigoutsos et al. | 395/603 |

FOREIGN PATENT DOCUMENTS

WO9607943  9/1994  (WO) ............... G06F/17/60

OTHER PUBLICATIONS

Cohen et al Molecular Modeling Software and Methods for Medicinal Chemistry. J. Med. Chem. 33(3) 883–898, 1990.*
Rothstein et al. GroupBuild: A fragment–based method for de novo. J. Med. Chem. 36(12) 1700–1709, 1993.*

* cited by examiner

*Primary Examiner*—Jyothsna Venkat
*Assistant Examiner*—Joseph W. Ricigliano
(74) *Attorney, Agent, or Firm*—Laurence Weinberger

(57) ABSTRACT

The problem of how to select out of a large chemically accessible universe molecules representative of the diversity of that universe is resolved by the discovery of a method to validate molecular structural descriptors. Using the validated descriptors, optimally diverse subsets can be selected. In addition, from the universe, molecules with characteristics similar to a selected molecule can be identified. The validated descriptors also enable the generation of a huge virtual library of potential product molecules which could be formed by combinatorial arrangement of structural variations and cores. In this virtual library it is possible to search billions of possible product compounds in relatively short time frames.

38 Claims, 44 Drawing Sheets

8B
REMOVE NON-DIVERSE REACTANTS:
  3D STRUCTURE GENERATION
  TOPOMERIC CONFORMER
    ALIGNMENT
  CoMFA FIELD GENERATION:
    HYDROGEN BOND FIELD
      GENERATION
    ROTATABLE BOND FIELD
      ATTENUATION
    CALCULATE FIELD
      DIFFERENCES
  CLUSTER
  REACTANT SELECTION FROM
    EACH CLUSTER

SYBYL: SELECTOR &
  CONCORD 3.2.1
    SPECIALIZED SOFTWARE:
      APPENDIX "A"
      (SYBYL: CoMFA
        STERIC & MSS)

SYBYL: HIERCHICAL
  CLUSTER - MSS
SYLBL: MSS

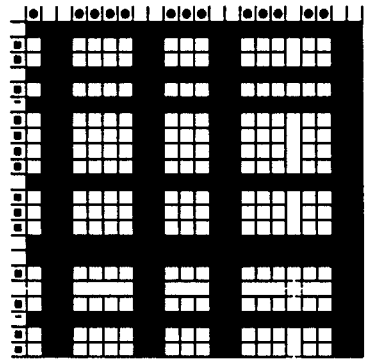

8C
COMBINE REACTANTS TO BUILD PRODUCTS

SYBYL: LEGION MSS

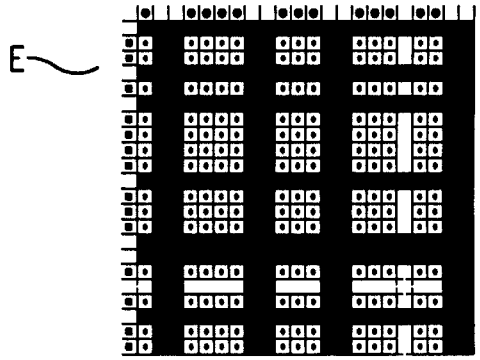

8D
REMOVE PRODUCTS:
  NON-DIVERSITY REASONS
  GENERAL CRITERIA:

SYBYL: SPL SCRIPTS
  ON MSS

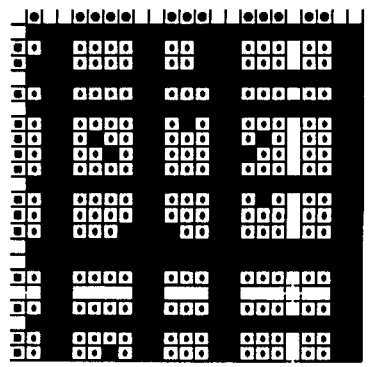

FIG.11(b)

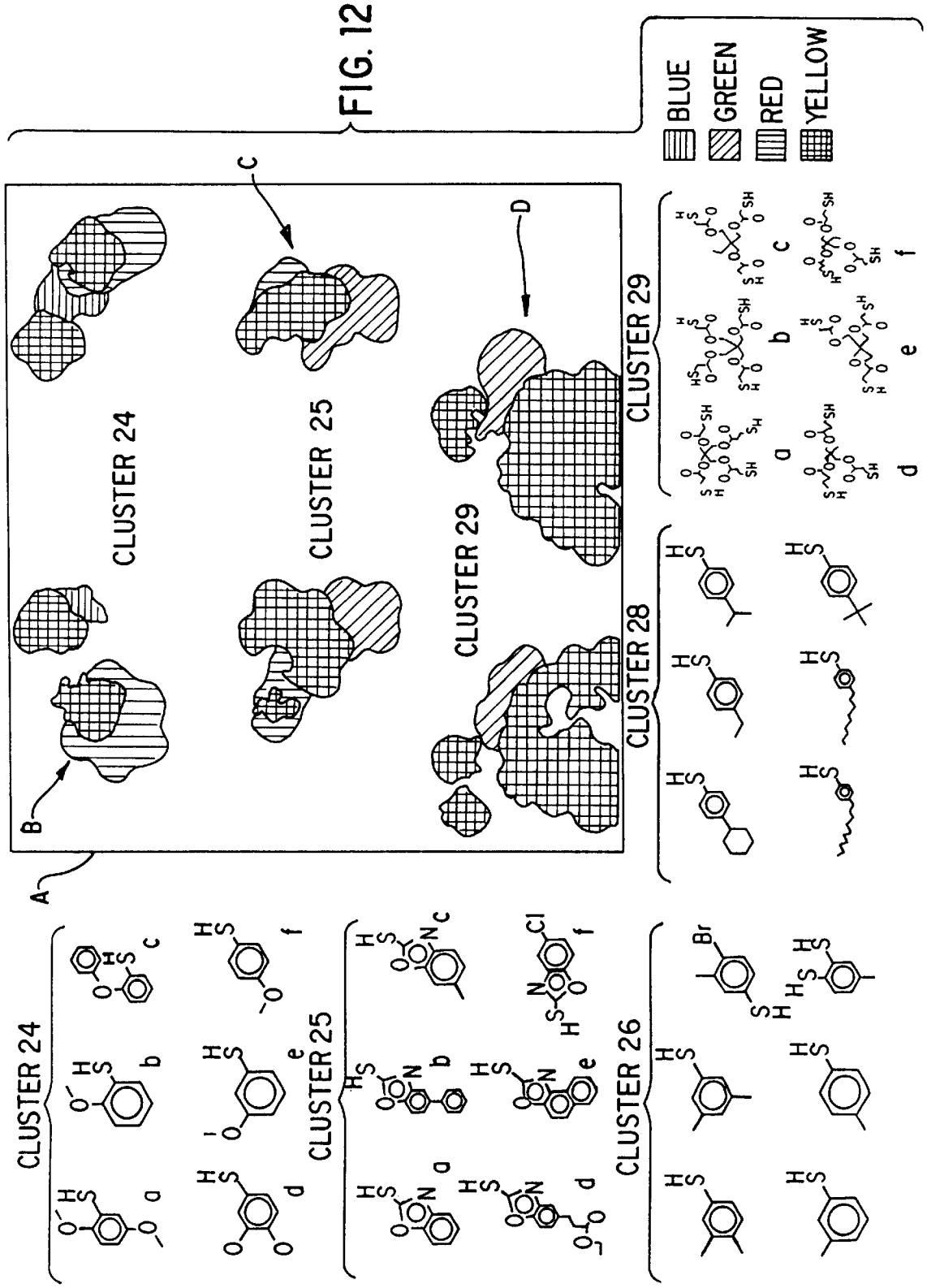

FURTHER METHOD OF CREATING AND RAPIDLY SEARCHING A VIRTUAL LIBRARY OF POTENTIAL MOLECULES USING VALIDATED MOLECULAR STRUCTURAL DESCRIPTORS

This application is a continuation-in-part of application Ser. No. 08/657,147 filed Jun. 3, 1996 entitled *A Method Of Creating And Rapidly Searching A Virtual Library Of Potential Molecules Using Validated Molecular Structural Descriptors*, now abandoned, which is a continuation-in-part of application Ser. No. 08/592,132 filed Jan. 26, 1996 entitled *A Method For Selecting An Optimally Diverse Library Of Small Molecules Based On Validated Molecular Structural Descriptors*, which issued Feb. 6, 2001 as a U.S. Pat. No. 6,185,506.

A portion of the disclosure of this patent document contains material which is subject to copyright protection. The copyright owner has no objection to the facsimile reproduction by anyone of the patent document or the patent disclosure, as it appears in the U.S. Patent and Trademark Office but otherwise reserves all copyright rights whatsoever.

TECHNICAL FIELD

This invention relates to the field of molecular structure/activity analysis and more specifically to: 1) a method of validating molecular structural descriptors; 2) a method using validated molecular descriptors to design an optimally diverse combinatorial screening library; 3) a method of merging libraries derived from different combinatorial chemistries; 4) a method using validated molecular descriptors of generating a searchable virtual library of molecules which can be combinatorially derived; 5) methods of searching the virtual library for combinatorially derived product molecules which meet specified criteria; and 6) methods of following up and optimizing identified leads. The screening libraries designed by the methods of this invention are constructed to ensure that an optimal structural diversity of compounds is represented. The search methods of the invention ensure that the same diversity space is not oversampled and that compounds can be identified having a high likelihood of possessing the same structure and/or activity of a lead compound. In particular, the invention describes the design of libraries of small molecules to be used for pharmacological testing.

BACKGROUND ART

Statement of the Problem

While the present invention is discussed with detailed reference to the search for and identification of pharmacologically useful chemical compounds, the invention is applicable to any attempt to search for and identify chemical compounds which have some desired physical or chemical characteristic(s). The broader teachings of this invention are easily recognized if a different functional utility or useful property describing other chemical systems is substituted below for the term "biological activity".

Starting with the serendipitous discovery of penicillin by Fleming and the subsequent directed searches for additional antibiotics by Waksman and Dubos, the field of drug discovery during the post World War II era has been driven by the belief that nature would provide many needed drugs if only a careful and diligent search for them was conducted. Consequently, pharmaceutical companies undertook massive screening programs which tested samples of natural products (typically isolated from soil or plants) for their biological properties. In a parallel effort to increase the effectiveness of the discovered "lead" compounds, medicinal chemists learned to synthesize derivatives and analogs of the compounds. Over the years, as biochemists identified new enzymes and biological reactions, large scale screening continued as compounds were tested for biological activity in an ever rapidly expanding number of biochemical pathways. However, proportionately fewer and fewer lead compounds possessing a desired therapeutic activity have been discovered. In an attempt to extend the range of compounds available for testing, during the last few years the search for unique biological materials has been extended to all corners of the earth including sources from both the tropical rain forests and the ocean. Despite these and other efforts, it is estimated that discovery and development of each new drug still takes about 12 years and costs on the order of 350 million dollars.

Beginning approximately twenty-five years ago, as bioscientists learned more about the chemical and stereochemical requirements for biological interactions, a variety of semi-empirical, theoretical, and quantitative approaches to drug design were developed. These approaches were accelerated by the availability of powerful computers to perform computational chemistry. It was hoped that the era of "rational drug design" would shorten the time between significant discoveries and also provide an approach to discovering compounds active in biological pathways for which no drugs had yet been discovered. In large part, this work was based on the accumulated observation of medicinal chemists that compounds which were structurally similar also possessed similar biological activities. While significant strides were made using this approach, it too, like the mass screening programs, failed to provide a solution to the problem of rapidly discovering new compounds with activities in the ever increasing number of biological pathways being elucidated by modern biotechnology.

During the past four or five years, a revised screening approach has been under development which, it was hoped, would accelerate the pace of drug discovery. In fact, the approach has been remarkably successful and represents one of the most active areas in biotechnology today. This new approach utilizes combinatorial libraries against which biological assays are screened. Combinatorial libraries are collections of molecules generated by synthetic pathways in which either: 1) two groups of reactants are combined to form products; or 2) one or more positions on core molecules are substituted by a different chemical constituent/moiety selected from a large number of possible constituents.

Two fundamental ideas underlie combinatorial screening libraries. The first idea, common to all drug research, is that somewhere amongst the diversity of all possible chemical structures there exist molecules which have the appropriate shape and binding properties to interact with any biological system. The second idea is the belief that synthesizing and testing many molecules in parallel is a more efficient way (in terms of time and cost) to find a molecule possessing a desired activity than the random testing of compounds, no matter what their source. In the broadest context, these ideas require that, since the binding requirements of a ligand to the biological systems under study (enzymes, membranes, receptors, antibodies, whole cell preparations, genetic materials, etc.) are not known, the screened compounds should possess as broad a range of characteristics (chemical and physical) as possible in order to increase the likelihood of finding one that is appropriate for any given biological target. This requirement for a screening library is reflected in the term "diversity"—essentially a way of suggesting that the library should contain as great a dissimilarity of compounds as possible.

However, as is immediately apparent, a combinatorial approach to synthesizing molecules generates an immense number of compounds many with a high degree of structural similarity. In fact, the number of compounds synthetically accessible with known organic reactions exceeds by many orders of magnitude the numbers which can actually be made and tested. One area where these ideas were first explored is in the design of peptide libraries. For a library of five member peptides synthesized using the 20 naturally occurring amino acids, 3,200,000, ($20^5$) different peptides may be constructed. The number of combinatorial possibilities increases even more dramatically when non-peptide combinatorial libraries are considered. With non-peptide libraries, the whole synthetic chemical universe of combinatorial possibilities is available. Library sizes ranging from $5\times10^7$ to $4\times10^{12}$ molecules are now being discussed. The enormous universe of chemical compounds is both a blessing and a curse to medicinal chemists seeking new drugs. On the one hand, if a molecule exists with the desired biological activity, it should be included in the chemical universe. On the other hand, it may be impossible to find. Thus, the principal focus of recent efforts has been to define smaller screening subsets of molecules derivable from accessible combinatorial syntheses without losing the inherent diversity of an accessible universe.

To date, in order to narrow the focus of the search and reduce the number of compounds to be screened, attention has been directed to designing biologically specific libraries. Thus, many combinatorial screening libraries existing in the prior art have been designed based on prior knowledge about a particular biological system such as a known pharmacophore (a geometric arrangement of structural fragments abstracted from molecular structures known to have activity). Even with this knowledge, molecules are included in these prior art libraries based on intuition—"seat of the pants" estimations of likely similarity based on an intuitive "feel" for the systems under study. This procedure is essentially pseudo-random screening, not rational library design. Several biotechnology startup companies have developed just such proprietary libraries, and success using combinatorial libraries has been achieved by sheer effort. In one example 18 libraries containing 43 million compounds were screened to identify 27 active compounds[1]. With library searches of this magnitude, it is most likely that the enormous number of inactive molecules [($43\times10^6$)–27] must have included staggering numbers of redundantly inactive molecules—molecules not significantly distinguishable from one another—even in libraries designed with a particular biological target in mind. Clearly, when searching for a lead molecule which interacts with an uncharacterized biological target, approaches requiring knowledge of the biological targets will not work. But finding such a lead is exactly the case for which it is hoped general purpose screening libraries can be designed. If the promise of combinatorial chemistry is ever to be fully realized, some rational and quantitative method of reducing the astronomical number of compounds accessible in the combinatorial chemistry universe to a number which can be usefully tested is required. In other words, the efficiency of the search process must be increased. For this purpose, a smaller rationally designed screening library, which still retains the diversity of the combinatorially accessible compounds, is absolutely necessary.

Thus, there are two criteria which must be met by any screening library subset of some universe of combinatorially accessible compounds. First, the diversity, the dissimilarity of the universe of compounds accessible by some combinatorial reaction, must be retained in the screening subset. A subset which does not contain examples of the total range of diversity in such a universe would potentially miss critical molecules, thereby frustrating the very reason for the creation of the subset. Second, for efficient screening, the ideal subset should not contain more than one compound representative of each aspect of the diversity of the larger group. If more than one example were included, the same diversity would be tested more than once. Such redundant screening would yield no new information while simultaneously increasing the number of compounds which must be synthesized and screened. Therefore, the fundamental problem is how to reduce to a manageable number the number of compounds that need to be synthesized and tested while at the same time providing a reasonably high probability that no possible molecule of biological importance is overlooked. (In this regard, it should be recognized that the only way of absolutely insuring that all diversity is represented in a library is to include and test all compounds.) A conceptual analogy to the problem might be: what kind of filter can be constructed to sort out from the middle of a blinding snowstorm individual snowflakes which represent all the classes of crystal structures which snowflakes can form?

The fundamental question plaguing progress in this area has been whether the concept of the diversity of molecular structure can be usefully described and quantified; that is, how is it possible to compare/distinguish the physical and chemical properties determinative of biological activity of one molecule with that of another molecule? Without some way to quantitatively describe diversity, no meaningful filter can be constructed. Fortunately, for biological systems, the accumulated wisdom of bioscientists has recognized a general principle alluded to earlier which provides a handle on this problem. As framed by Johnson and Maggiora[2], the principle is simply stated as: "structurally similar molecules are expected to exhibit similar (biological) properties." Based on this principle, quantifying diversity becomes a matter of quantifying the notion of structural similarity. Thus, for design of a screening subset of a combinatorial library (hereafter referred to as a "combinatorial screening library"), it should only be necessary to identify which molecules are structurally similar and which structurally dissimilar. According to the selection criteria outlined above, one molecule of each structurally similar group in the combinatorially accessible chemical universe would be included in the library subset. Such a library would be an optimally diverse combinatorial screening library. The problem for medicinal chemists is to determine how the intuitively perceived notions of structural similarity of chemical compounds can be validly quantified. Once this question is satisfactorily answered, it should be possible to rationally design combinatorial screening libraries.

Prior Art Approaches

Many descriptors of molecular structure have been created in the prior art in an attempt to quantify structural similarity and/or dissimilarity. As the art has recognized, however, no method currently exists to distinguish those descriptors that quantify useful aspects of similarity from those which do not. The importance of being able to validate molecular descriptors has been a vexing problem restricting advances in the art, and, before this invention, no generally applicable and satisfactory answer had been found. The problem may be conceptual in terms of a multidimensional space of structurally derivable properties which is populated by all possible combinatorially accessible chemical compounds. Compounds lying "near" one another in any one dimension may lie "far apart" from one another in another dimension. The difficulty is to find a useful design space—a quantifiable dimensional space (metric space) in which compounds with similar biological properties cluster; ie., are found measurably near to each other. What is desired is a molecular structural descriptor which, when applied to the molecules of the chemical universe, defines a dimensional space in which the "nearness" of the molecules with respect to a specified characteristic (ie.; biological activity) in the chemical universe is preserved in the dimensional space. A molecular structural descriptor (metric) which does not have this property is useless as a descriptor of molecular diversity. A valid descriptor is defined as one which has this property.

In light of the above, it should be noted that there is a difference between a descriptor being valid and being perfect. There may or may not be a "perfect" metric which precisely and quantitatively maps the diversity of compounds (much less those of biological interest). However, a good approximation is sufficient for purposes of designing a combinatorial screening library and is considered valid/useful. Acceptance of this validation/usefulness criteria is essentially equivalent to saying that, if there is a high probability that if one molecule is active (or inactive), a second molecule is also active (or inactive), then most of the time sampling one of the pair will be sufficient. Restating this same principle with a slightly different emphasis highlights another feature, namely: the design criteria for combinatorial screening libraries should yield a high probability that, for any given inactive molecule, it is more probable to find an active molecule somewhere else rather than as a near neighbor of that inactive molecule. While this is a probabilistic approach, it emphasizes that a good approximation to a perfect metric is sufficient for purposes of designing a combinatorial screening library as well as in other situations where the ability to discriminate molecular structural difference and similarities is required. A perfect descriptor (certainty) for pharmacological searching is not needed to achieve the required level of confidence as long as it is valid (maps a subspace where biological properties cluster).

The typical prior art approach for establishing selection criteria for screening library subsets relied on the following clustering paradigm: 1) characterization of compounds according to a chosen descriptor(s) (metric[s]); 2) calculation of similarities or "distances" in the descriptor (metric) between all pairs of compounds; and 3) grouping or clustering of the compounds based on the descriptor distances. The idea behind the paradigm is that, within a cluster, compounds should have similar activities and, therefore, only one or a few compounds from each cluster, which will be representative of that cluster, need be included in a library. The actual clustering is done until the prior art user feels comfortable with the groupings and their spacing. However, with no knowledge of the validity/usefulness of the descriptor employed, and no guidance with respect to the size or spacing of clusters to be expected from any given descriptor, prior art clustering has been, at best, another intuitive "seat of the pants" approach to diversity measurement.

The prior art describes the construction and application of many molecular structural descriptors while all the while tacitly acknowledging that little progress has been made towards solving the fundamental problem of establishing their validity. The field has nevertheless proceeded based on the belief/faith that, by incorporating in the descriptors certain measures which had been recognized in QSAR studies as being important contributors to defining structure-activity relationships, valid/useful descriptors would be produced. In a leading method representative of this prior art approach to defining a similarity descriptor, E. Martin et al.[3] construct a metric for quantifying structural similarity using measures that characterize lipophilicity, shape and branching, chemical functionality, and receptor recognition features. (For the reasons set forth later in relation to the present invention, Martin et al. applied their metric to the reactants which would be used in combinatorial synthesis.) This large set of measures is used to generate a statistically blended metric consisting of a total of 16 properties for each individual reactant studied (5 shape descriptors, 5 measures of chemical functionality, 5 receptor binding descriptors, and one lipophilicity property). This generates a 16 dimensional property space. The 16 properties are simultaneously displayed in a circular "Flower Plots" graphical environment, where each property is assigned a petal. All the plots together visually display how the diversity of the studied reactants is distributed through the computed property space. Martin acknowledges that the plots ". . . cannot, of course, prove that the subset is diverse in any 'absolute'sense, independent of the calculated properties." (Martin at 1434)

In another approach relating to peptoid design, Martin et al.[4] have characterized the varieties of shape that an unknown receptor cavity might assume by a few assemblages of blocks, called "polyominos". Candidates for a combinatorial design are classified by the types of polyominos into which they can be made to fit, or "docked". The 7 flexible polyomino shape descriptors are added to the previously defined 16 descriptors to yield a 23 dimensional property space. Martin has demonstrated that the docking procedure generates for a methotrexate ligand in a cavity of dihydrofolate reductase nearly the correct structure as that established by X-ray diffraction studies. The docking procedure, which must be applied to every design candidate for each polyomino, requires a considerable amount of CPU time (is computationally expensive). However, a problem with this approach is the conceptually severe (unjustified) approximation of representing all possible irregularly shaped receptor cavities by only about a dozen assemblies of smooth-sided polyomino cubes. Martin has also presented no validation of the approach, which in this case, would be a demonstration that molecules which fit into the same polyominos tend to have similar biological properties.

One approach which has been taken to try to empirically assess the relative validity of prior art metrics has been to survey the metrics to see if any of them appeared to be superior to any others as judged by clustering analysis. Y. C. Martin et al.[5] have reported that 3D fingerprints, collections of fragments defined by pairs of atoms and their accessible interatomic distances, perform no better than collections of 2D fragments in defining clusters that separate biologically active from inactive compounds. As will be seen later, some of this work pointed towards the possible validity of one metric, but the authors concentrated on the comparative clustering aspects and did not follow up on the broader import of the data.

W. Herndon[6] among others has pointed out that an experimentally determined similarity QSAR is, by definition, a good test of the validity of that similarity concept for the biological system from which it is derived and may have some usefulness in estimating diversity for that system. However, QSARs essentially map only the space of a particular receptor, do not provide information about the validity of other descriptors, and would be generally inapplicable to construction of a combinatorial screening library designed for screening unknown receptors or those for which no QSAR data was available.

Finally, D. Chapman et al.[7] have used their "Compass" 3D-QSAR descriptor which is based on the three dimensional shape of molecules, the locations of polar functionalities on the molecules, and the fixation entropies of the molecules to estimate the similarity of molecules. Essentially, using the descriptor, they try to find the molecules which have the maximum overlap (in geometric/cartesian space) with each other. The shape of each molecule of a series is allowed to translate and rotate relative to each other molecule and the internal degrees of freedom are also allowed to rotate in an iterative procedure until the shapes with greatest or least overlap similarity are identified. Selecting 20 maximally diverse carboxylic acids based on seeking the maximally diverse alignment of each of the 3000 acids considered took approximately 4 CPU computing weeks by their method. No indication was given of whether their descriptor was valid in the sense defined above, and, clearly, such a procedure would be too time consuming to apply to a truly large combinatorial library design.

One way in which many of the prior art approaches attempt to work around the problem of not knowing if a molecular structural descriptor is valid is to try, when clustering, to maximize as much as possible the distance between the clusters from which compounds will be selected for inclusion in the screening library subset. The thinking behind this approach is that, if the clusters are far enough apart, only molecules diverse from each other will be chosen. Conversely, it is thought that, if the clusters are close together, oversampling (selection of two or more molecules representative of the same elements of diversity) would likely occur. However, as we have seen, if the metric used in the cluster analysis is not initially valid (does not define a subspace in which molecules with similar biological activity cluster), then no amount of manipulation will prevent the sample from being essentially random. Worse yet, an invalid metric might not yield a selection as good as random! The acknowledgement by Martin quoted above is a recognition of the prior art's failure to yet discover a general method for validating descriptors.

Another related problem in the prior art is the failure to have any objective manner of ascertaining when the library subset under design has an adequate number of members; that is, when to stop sampling. Clearly, if nothing is known about the distribution of the diversity of molecules, one arbitrary stopping point is as good as any other. Any stopping point may or may not sample sufficiently or may oversample. In fact, the prior art has not recognized a coherent quantitative methodology for determining the end point of selection. Essentially, in the prior art, a metric is used to maximize the presumed differences between molecules (typically in a clustering analysis), and a very large number of molecules are chosen for inclusion in a screening library subset based on the belief that there is safety in numbers; that sampling more molecules will result in sampling more of the diversity of a combinatorially accessible chemical space. As pointed out earlier, however, only by including all possible molecules in a library will one guarantee that all of the diversity has been sampled. Short of such total sampling, users of prior art library subsets constructed along the lines noted above do not know whether a random sample, a representative sample, or a highly skewed sample has been screened.

Several other problems flow from the inability to rationally select a combinatorial screening library for optimal diversity and these are related both to the chemistry used to create the combinatorial library and the screening systems used. First, because many more molecules may have to be synthesized than may be needed, mass synthetic schemes have to be devised which create many combinations simultaneously. In fact, there is a good deal of disagreement in the prior art as to whether compounds should be synthesized individually or collectively or in solution or on solid supports. Within any synthetic scheme, an additional problem is keeping track of and identifying the combinations created. It should be understood that, where relatively small (molecular weight of less than about 1500) organic molecules are concerned, generally standard, well known, organic reactions are used to create the molecules. In the case of peptide like molecules, standard methods of peptide synthesis are employed. Similarly for polysaccharides and other polymers, reaction schemes exist in the prior art which are well known and can be utilized. While the synthesis of any individual combinatorial molecule may be straightforward, much time and effort has been and is still being expended to develop synthetic schemes in which hundreds, thousands, or tens of thousands of combinatorial combinations can be synthesized simultaneously.

In many synthetic schemes, mixtures of combinatorial products are synthesized for screening in which the identity of each individual component is uncertain. Alternatively, many different combinatorial products may be mixed together for simultaneous screening. Each additional molecule added to a simultaneous screen means that many fewer individual screening operations have to be performed. Thus, it is not unusual that a single assay may be simultaneously tested against up to 625 or more different molecules. Not until the mixture shows some activity in the biological screening assay will an attempt be made to identify the components. Many approaches in the prior art therefore face "deconvolution" problems; ie. trying to figure out what was in an active mixture either by following the synthetic reaction pathway, by resynthesizing the individual molecules which should have resulted from the reaction pathway, or by direct analysis of duplicate samples. Some approaches even tag the carrier of each different molecule with a unique molecular identifier which can be read when necessary. All these problems are significantly decreased by designing a library for optimal diversity.

Another major problem with the inclusion of multiple and potentially non-diverse compounds in the same screening mixture is that many assays will yield false positives (have an activity detected above a certain established threshold) due to the combined effect of all the molecules in the screening mixture. The absence of the desired activity is only determined after expending the time, effort, and expense of identifying the molecules present in the mixture and testing them individually. Such instances of combined reactivity are reduced when the screening mixture can be selected from molecules belonging to diverse groups of an optimally designed library since it is not as likely that molecules of different (diversity) structures would likely produce a combined effect.

It is clear that a great deal of cleverness has been expended in actually manufacturing the combinatorial libraries. While the basic chemistry of synthesizing any given molecule is straight forward, the next advance in the development of combinatorial chemistry screening libraries will be optimization of the design of the libraries.

Further problems in the prior art arise in the attempt to follow up leads resulting from the screening process. As noted above, many libraries are designed with some knowledge of the receptor and its binding requirements. While, within those constraints, all possible combinatorial molecules are synthesized for screening, finding a few molecules with the desired activity among such a library yields no information about what active molecules might exist in the universe accessible with the same combinatorial chemistry but outside the limited (receptor) library definition. This is an especially troubling problem since, from serendipitous experience, it is well known that sometimes totally unexpected molecules with little or no obvious similarity to known active molecules exhibit significant activity in some biological systems. Thus, even finding a candidate lead in a library whose design was based on knowledge of the receptor is no guarantee that the lead can be followed to an optimal compound. Only a rationally designed combinatorial screening library of optimal diversity can approach this goal.

For prior art library subsets designed around the use of some descriptor to cluster compounds, similar problems may exist. In such a library design, one or at most a few compounds will have been selected from each cluster. Only if the descriptor is valid, does such a selection procedure make sense. If the descriptor is not valid, each cluster will contain molecules representative of many different diversities and selecting from each cluster will still have resulted in a random set of molecules which do not sample all of the diversity present. Since the prior art does not possess a generally applicable method of validating descriptors, all screening performed with prior art libraries is suspect and may not have yielded all the useful information desired about the larger chemical universe from which the library subsets were selected.

Finally, as the expense in time and effort of creating and screening combinatorial libraries increases, the question of the uniqueness of the libraries becomes ever more critical. Questions can be asked such as: 1) does library "one" cover the same diversity of chemical structures as library "two"; 2) if libraries "one" and "two" cover both different and identical aspects of diversity, how much overlap is there; 3) what about the possible overlap with libraries "three", "four", "five", etc.? To date, the prior art has been unable to answer these questions. In fact, assumptions have been made that as long as different chemistries were involved (ie., proteins, polysaccharides, small organic molecules), it was unlikely that the same diversity space was being sampled. However, such an assumption contradicts the well known reality that biological receptors can recognize molecular similarities arising from different structures. When screening for compounds possessing activity for undefined biological receptors, there is no way of telling a priori which chemistry or chemistries is most likely to produce molecules with activity for that receptor. Thus, screening with as many chemistries as possible is desired but is only really practical if redundant sampling of the same diversity space in each chemistry can be avoided. The prior art has not provided any guidance towards the resolution of these problems.

BRIEF SUMMARY OF THE INVENTION

In order to select a screening subset of a combinatorially accessible chemical universe which is representative of all the structural variation (diversity) to be found in the universe, it is necessary to have the means to describe and compare the molecular structural diversity in the universe. The first aspect of the present invention is the discovery of a generalized method of validating descriptors of molecular structural diversity. The method does not assume any prior knowledge of either the nature of the descriptor or of the biological system being studied and is generally applicable to all types of descriptors of molecular structure. This discovery enables several related advances to the art.

The second aspect of the invention is the discovery of a method of generating a validated three dimensional molecular structural descriptor using CoMFA fields. To generate these field descriptors required solving the alignment problem associated with these measurements. The alignment problem was solved using a topomeric procedure.

A third aspect of the invention is the discovery that validated molecular structural descriptors applicable to whole molecules can be used both to: 1) quantitatively define a meaningful end-point for selection in defining a single screening library (sampling procedure); and 2) merge libraries so as not to include molecules of the same or similar diversity. It is shown that a known metric (Tanimoto 2D fingerprint similarity) can be used in conjunction with the sampling procedure for this purpose.

A fourth aspect of the invention is the discovery of a method of using validated reactant and whole molecule molecular structural descriptors to rationally design a combinatorial screening library of optimal diversity. In particular, the shape sensitive topomeric CoMFA descriptor and the atom group Tanimoto 2D similarity descriptor may be used in the library design. As a benefit of designing a combinatorial screening library of optimal diversity based on validated molecular descriptors, many prior art problems associated with the synthesis, identification, and screening of mixtures of combinatorial molecules can be reduced or eliminated.

A fifth aspect of the invention is the use of validated molecular structural descriptors to guide the search for optimally active compounds after a lead compound has been identified by screening. In the case of a screening library designed for optimal diversity using validated descriptors, a great deal of the information necessary for lead optimization flows directly from the library design. In the case where a lead has been identified by screening a prior art library or through some other means, validated descriptors provide a method for identifying the molecular structural space nearest the lead which is most likely to contain compounds with the same or similar activity.

A sixth aspect of this invention is the discovery of a method for generating, using validated molecular descriptors, a virtual library of product molecules derivable from combinatorial reactions (or which may be represented by a combinatorial SLN [CSLN]) in which the characteristics of product molecules can be searched and compared without the actual construction of the product molecules. This virtual library allows the searching of billions of possible product molecules in reasonable amounts of time.

A seventh aspect of this invention is the discovery that, using validated molecular descriptors, the virtual library can be searched over billions of possible product molecules in ways to yield both optimally diverse screening libraries and to follow up on lead explosions. Using the virtual library, a much larger fraction of the chemically accessible universe can be searched for molecules of interest.

An eighth aspect of this invention is the discovery of a way to search, using validated molecular descriptors, the virtual library for possible molecules which have similar structures and/or activities to a query molecule which is not necessarily derived from a combinatorial synthesis. This discovery opens up a whole new method for seeking molecules with similar characteristics to a previously identified molecule.

It is an object of this invention to define a general process which may be used with randomly selected literature data sets to validate molecular structural descriptors.

It is a further object of this invention to define a process to derive CoMFA steric fields (and, if desired, additional relevant fields) using topomeric alignment so that the resulting descriptor is valid.

It is a further object of this invention to teach that topomeric alignments may be used to describe molecular conformations.

It is a further object of this invention to define a general process for using a validated molecular descriptor to establish a meaningful end-point for the sampling of compounds thereby avoiding the oversampling of compounds representing the same molecular structural characteristics.

It is yet a further object of this invention to design an optimally diverse combinatorial screening library using multiple validated molecular structural descriptors.

It is a further object of this invention to use the topomeric CoMFA molecular structural descriptor as a reactant descriptor in the design of an optimally diverse combinatorial screening library.

It is a further object of this invention to use the Tanimoto 2D similarity molecular structural descriptor as a product descriptor in the design of an optimally diverse combinatorial screening library.

It is a further object of this invention to define a method for merging assemblies of molecules (libraries), both those designed by the methods of this invention and others not designed by the methods of this invention, in such a manner that molecules representing the same or similar diversity space are not likely to be included.

It is a further object of this invention to define methods for the use of validated molecular structural descriptors to guide the search for optimally active compounds after a lead compound has been identified by screening or some other method.

It is a further object of this invention to generate a virtual library, using validated molecular descriptors, of potential product molecules derivable from combinatorial reactions (or which may be represented by a combinatorial SLN [CSLN]) which can be searched for molecules having desired characteristics.

It is a further object of this invention to define methods for creating optimal diversity screening libraries as subsets of the virtual library.

It is still a further object of this invention to locate within the virtual library possible product molecules similar in structure and/or activity to lead compounds.

These and further objects of the invention will become apparent from the detailed description of the invention which follows.

BRIEF DESCRIPTION OF DRAWINGS

FIGS. 11a through 11c are a schematic of the combinatorial screening library design process.

FIG. 12 shows a comparison of the volumes of space occupied by different molecules which are determined to be similar according to the Tanimoto 2D fingerprint descriptor but which are determined to be dissimilar according to the topomeric CoMFA field descriptor.

Disclosure Of Invention

Figure 1A:
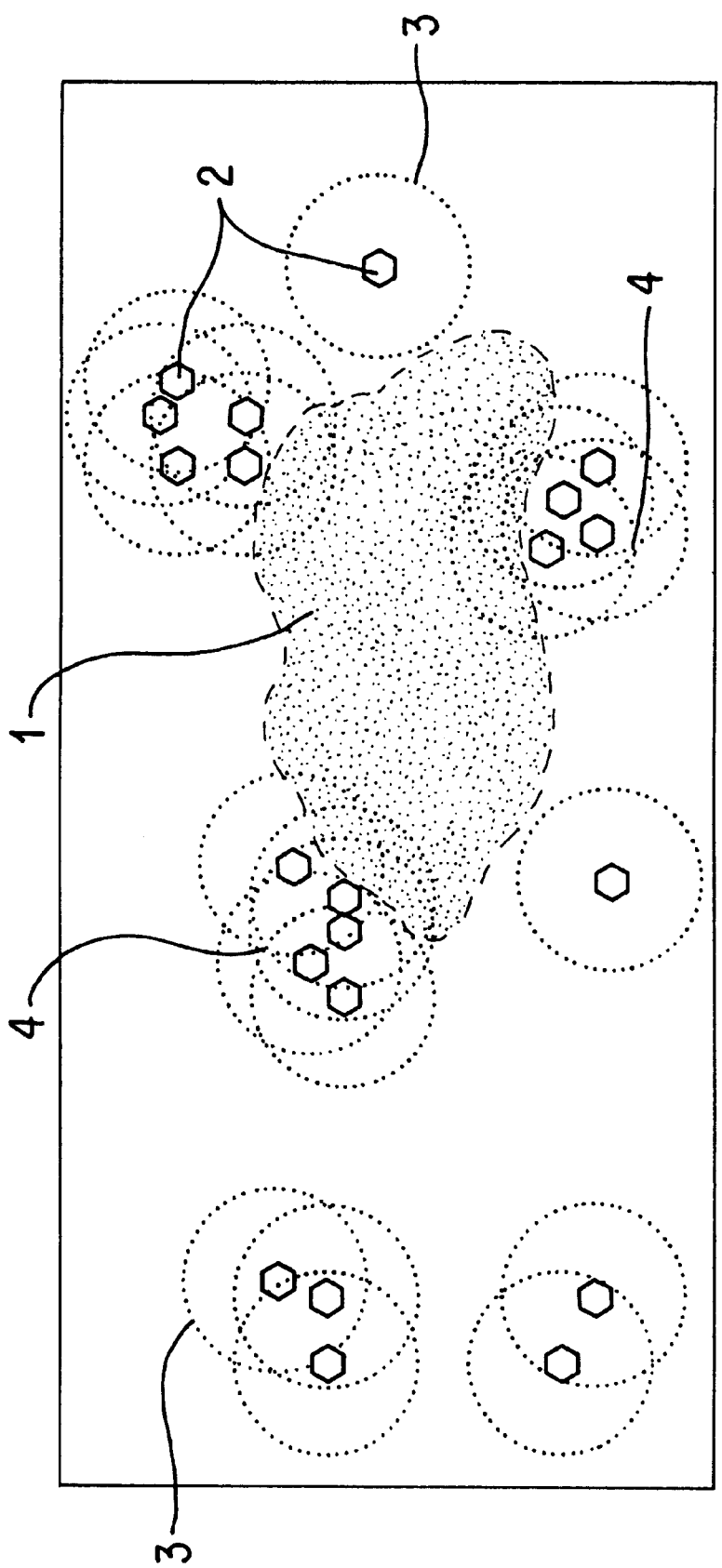
FIGS. 1a and 1b schematically show the distribution of molecular structures around and about an island of biological activity in a hypothetical two dimensional metric space for a poorly designed prior art library and for an efficiently designed optimally diverse screening library.

1. Computational Chemistry Environment
2. Definitions
3. Validating Metrics
   A. Theoretical Considerations - Neighborhood Property
   B. Construction, Application, and Analysis Of Patterson Plots
4. Topomeric CoMFA Descriptor
   A. Topomeric Alignment
      i. General Topomeric Allignment
      ii. Specialized Allignment for Chiral and Equivalent Atoms
   B. Calculation Of CoMFA and Hydrogen Bonding Fields
   C. Validation Of Topomeric CoMFA Descriptor
5. Tanimoto Fingerprint Descriptor
   A. Neighborhood Property
   B. Applicability Of Tanimoto To Different Biological Systems
   C. Comparison of Sigmoid and Patterson Plots
6. Comparison of Tanimoto and Topomeric CoMFA Metrics
7. Additional Validation Results
8. Combinatorial Library Design Utilizing Validated Metrics
   A. Removal Of Reactants For Non-Diversity Reasons
      i. General Removal Criteria
      ii. Biologically Based Criteria5
   B. Removal of Non-Diverse Reactants
   C. Identification (Building) Of Products
   D. Removal Of Products For Non-Diversity Reasons
   E. Removal of Non-Diverse Products
9. Lead Compound Optimization
   A. Advantages Resulting From Product Filter
   B. Advantages Resulting From Reactant Filter
   C. Additional Optimization Methods Using Validated Metrics
10. Merging Libraries
11. Other Advantages of Optimally Diverse Libraries
12. Virtual Library Construction & Searching
    A. Derivation of the Database (Virtual Library) of Compounds
    B. Overview of Methodology
    C. Overview of Virtual Library Construction
    D. Virtual Library Construction
       i. Representation of the Database of Compounds
       ii. Application of A First Metric (Topomeric CoMFA)
       iii. Application of A Second Metric (Tanimoto Fingerprint)
       iv. Summary of Method & Scope of Chemistry
    E. Searching the Virtual Library
       i. Example Search Routine of Virtual Library - Tanimoto Similarity
       ii. Design Screening Libraries (Subsets of the Virtual Library)
          (a) Subset Screening Library Based On Topomeric Fields and Tanimoto
          (b) Subset Based on Tanimoto Similarity
          (c) Subset Based on Topomeric Fields
          (d) Subset Based on Combined Metric
       iii. Designing lead Optimizations
          (a) Search Based on Tanimoto Similarity
          (b) Searches Based on Topomer Similarity
          (c) Topomeric (3D) Searching of Arbitrary Molecular Structures
          (d) Topomeric (3D) Searching of Core Structures 1. Computational Chemistry Environment Generally, all calculations and analyses to conduct combinatorial chemistry screening library design and follow up are implemented in a modern computational chemistry environment using software designed to handle molecular structures and associated properties and operations. For purposes of this Application, such an environment is specifically referenced. In particular, the computational environment and capabilities of the SYBYL and UNITY software programs developed and marketed by Tripos, Inc. (St. Louis, Mo.) are specifically utilized. Unless otherwise noted, all software references and commands in the following text are references to functionalities contained in the SYBYL and UNITY software programs. Where a required functionality is not available in SYBYL or UNITY, the software code to implement that functionality is provided in an Appendix to this Application. Software with similar functionalities to SYBYL and UNITY are available from other sources, both commercial and non-commercial, well known to those in the art. A general purpose programmable digital computer with ample amounts of memory and hard disk storage is required for the implementation of this invention. In performing the methods of this invention, representations of thousands of molecules and molecular structures as well as other data may need to be stored simultaneously in the random access memory of the computer or in rapidly available permanent storage. The inventors use a Silicon Graphics, Inc. Challenge-M computer having a single 150 Mhz R4400 processor with 128 Mb memory and 4 Gb hard disk storage space. As the size of the virtual library increases, a corresponding increase in hard disk storage and computational power is required. For these tasks, access to several gigabytes of storage and Silicon Graphics, Inc. processors in the R4400 to R10000 range are useful.

2. Definitions

The words or phrases in capital letters shall, for the purposes of this application, have the meanings set forth below:

2D MEASURES shall mean a molecular representation which does not include any terms which specifically incorporate information about the three dimensional features of the molecule. 2D is a misnomer used in the art and does not mean a geometric "two dimensional" descriptor such as a flat image on a piece of paper. Rather, 2D descriptors take no account of geometric features of a molecule but instead reflect only the properties which are derivable from its topology; that is, the network of atoms connected by bonds.

2D FINGERPRINTS shall mean a 2D molecular measure in which a bit in a data string is set corresponding to the occurrence of a given 2–7 atom fragment in that molecule. Typically, strings of roughly 900 to 2400 bits are used. A particular bit may be set by many different fragments.

COMBINATORIAL SCREENING LIBRARY shall mean a subset of molecules selected from a combinatorial accessible universe of molecules to be used for screening in an assay.

MOLECULAR STRUCTURAL DESCRIPTOR shall mean a quantitative representation of the physical and chemical properties determinative of the activity of a molecule. The term METRIC is synonymous with MOLECULAR STRUCTURAL DESCRIPTOR and is used interchangeably throughout this Application.

PATTERSON PLOTS shall mean two dimensional scatter plots in which the distance between molecules in some metric is plotted on the X axis and the absolute difference in some biological activity for the same molecules is plotted on the Y axis.

SIGMOID PLOTS shall mean two dimensional plots for which the proportion of molecular pairs in which the second molecule is also active is plotted on the Y axis and the pairwise Tanimoto similarity is plotted in intervals on the X axis.

TOPOMERIC ALIGNMENT shall mean conformer alignment based on a set of alignment rules.

3. Validating Metrics

A. Theoretical Considerations—Neighborhood Property

As noted above, the similarity principle suggests a way to quantify the concept of diversity by quantifying structural similarity. While the prior art devised many structural descriptors, no one has been able to explicitly show that any of the descriptors are valid. It is possible with the method of this invention to determine the validity of any metric by applying it to presently existing literature data sets, for which values of biological activity and molecular structure are known. Once the validity has been determined, the metric may be used with confidence in designing combinatorial screening libraries and in following up on discovered leads. Examples of these applications will be given below.

The present invention is the first to recognize that the similarity principle also provides a way to validate metrics. Specifically, the similarity principle requires that any valid descriptor must have a "neighborhood property". That is: the descriptor must meet the similarity principle's constraint that it measure the chemical universe in such a way that similar structures (as defined by the descriptor) have substantially similar biological properties. Or stated slightly differently: within some radius in descriptor space of any given molecule possessing some biological property, there should be a high probability that other molecules found within that radius will also have the same biological property. If a descriptor does not have the neighborhood property, it does not meet the similarity principle, and can not be valid. Regardless of the computations involved or the intentions of the users, using prior art descriptors without the neighborhood property results, at best, in random selection of compounds to include in screening libraries.

Figure 1B:
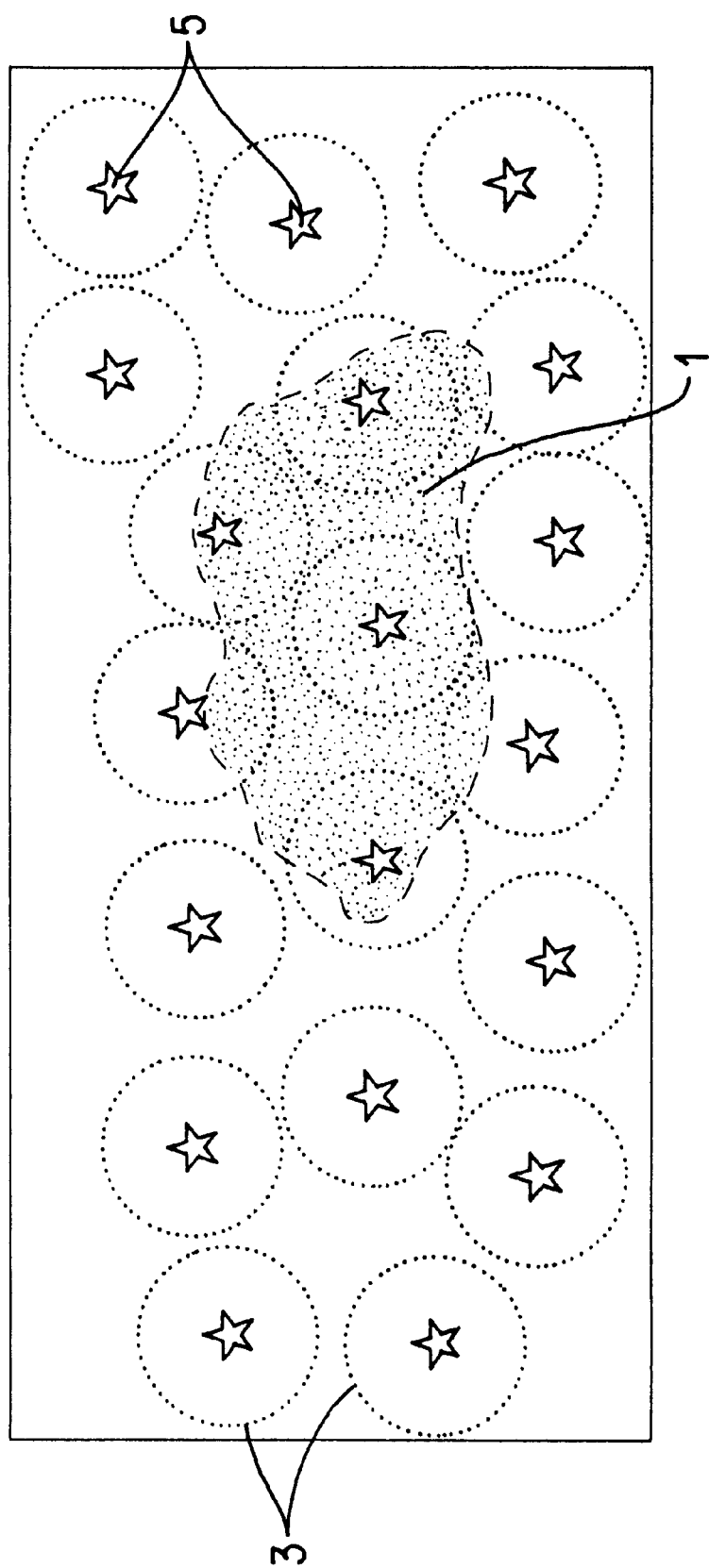

The importance of the neighborhood property to the design of combinatorial screening libraries is schematically illustrated in FIG. 1. FIG. 1A and FIG. 1B show an "island" 1 of biological activity plotted in some relevant two dimensional molecular descriptor space. In FIG. 1A the molecules 2 of a typical prior art library are plotted as hexagons. Around each hexagon a circle 3 describes the area of the metric space (the neighborhood) in which molecules of similar structural diversity to the plotted molecule would be found. Since the prior art metric used to select these molecules was not valid, the molecules are essentially distributed at random in the metric space. The circles 3 (neighborhoods) of similar structural diversity of several of the molecules overlap at 4 indicating that they sample the same diversity space. Clearly, there is no guarantee that the island area will be adequately sampled or that a great deal of redundant testing will not be involved with such a library design.

In FIG. 1B the molecules 5 of a optimally designed library are plotted as stars along with their corresponding circles 3 of similar structural diversity. Since a valid molecular descriptor with the neighborhood property was used to select the molecules, molecules were identified which not only sampled that part of the descriptor space accessible with the molecular structures available but also did not sample the same descriptor space more than once. Clearly, the likelihood of sampling the "island" 1 is greater when it is possible to identify the unique neighborhood 3 around each sample molecule and choose molecules that sample different areas. FIG. 1B represents an optimally diverse design.

A method to quantitatively analyze whether any given metric obeys the neighborhood principle has been discovered. In the prior art, absolute values of biological activity have always been considered the dependent variable with the structural metric as the independent variable. This is the case for traditional QSARs (quantitative structure activity relationships). Note however, that the similarity principle requires that for any pair of molecules, differences in activity are related to differences in structure. In particular, small differences in structure should be associated with small differences in activity. However, the converse is not necessarily true; large differences in activity are not necessarily associated with large differences in structure. The first novel feature of the present invention is that it uses differences in both measures: biological differences and structural (metric) differences. There is no rationale present in the prior art suggesting that the use of both differences in such a manner would be useful. Thus, instead of looking at the values assigned by the metric to each molecule, the absolute differences in the metric values for each pair of molecules are the independent variables and the absolute differences in biological activity for each pair of molecules are the dependent variables. The absolute value is used since it is the difference, not its sign, which is important.

Figure 2:
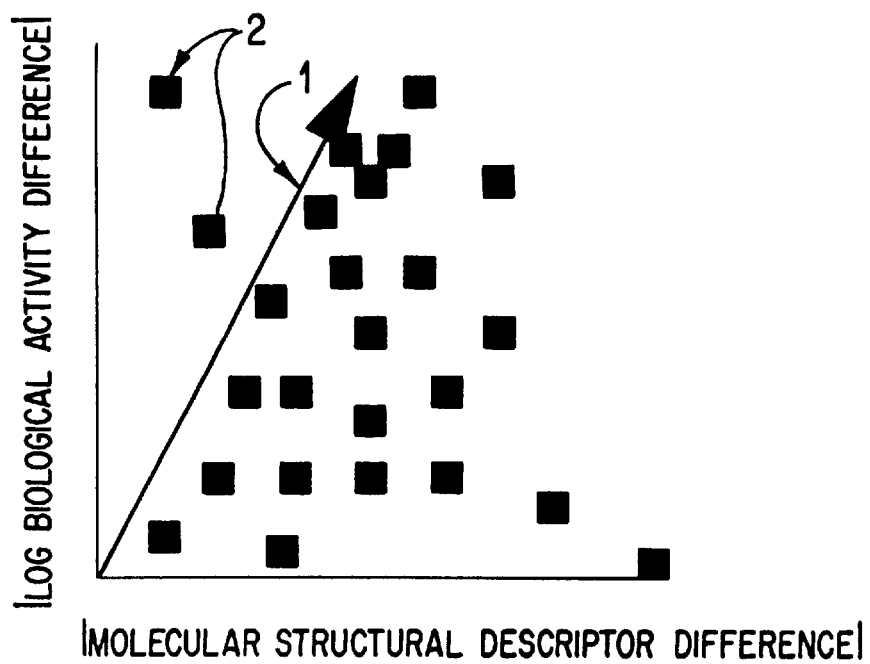
FIG. 2 shows a theoretical scatter plot (Patterson Plot) for a metric having the neighborhood property in which the X axis shows distances in some metric space calculated as the absolute value of the pairwise differences in some candidate molecular descriptor and the Y axis shows the absolute value of the pairwise differences in biological activity.

For a metric possessing the neighborhood property, a scatter plot of pairwise absolute differences in descriptors for each set of molecules versus pairwise absolute differences in biological activity for the same set of molecules (Patterson plot) will have a characteristic appearance as shown in FIG. 2. Note that it is important that pairwise absolute differences for all molecules in a data set are used, that is; the absolute metric "distance" between every molecule and every other molecule is plotted. Accordingly, there are $n(n-1)/2$ pairwise comparisons for every data set containing $n$ compounds. The use of pairwise differences for every possible pair reflects all the relationships between all structural changes with all activity changes for the molecules under study.

Line 1 on the graph of FIG. 2 depicts a special case where there is a strictly linear relationship between differences in metric distance and differences in biological activity. However, the neighborhood property does not imply a linear correlation (corresponding to points lying on a straight line) and need not imply anything about large property differences causing large biological activity differences. (Generally, the line should be linear for only very small changes in molecular structure and would exhibit a complex shape overall depending on the nature of the biological interaction. However, for purposes of discussion and analysis, it is useful to employ a straight line as a first approximation.) The slope of line 1 will vary depending on the biological activity of the measured system. Thus, the lower right trapezoid (LRT) {defined by the vertices [0,0], [actual metric value, max. bio. value], [max. metric value, max. bio. value], and [max. metric value, 0]} of the plot may be populated as shown in any number of ways.

The upper left triangle (ULT) of the plot (above the line) should not be populated at all as long as the descriptor completely characterizes the compound and there are no discontinuities in the behavior of the molecules. However, in the real world, some population of the space (as indicated by points 2) above the line would be expected since there are known discontinuities in the behavior of real molecular ligands. For instance, it is well known amongst medicinal chemists that adding one methyl group can cause some very active compounds to lose all sign of activity.

Figure 3:
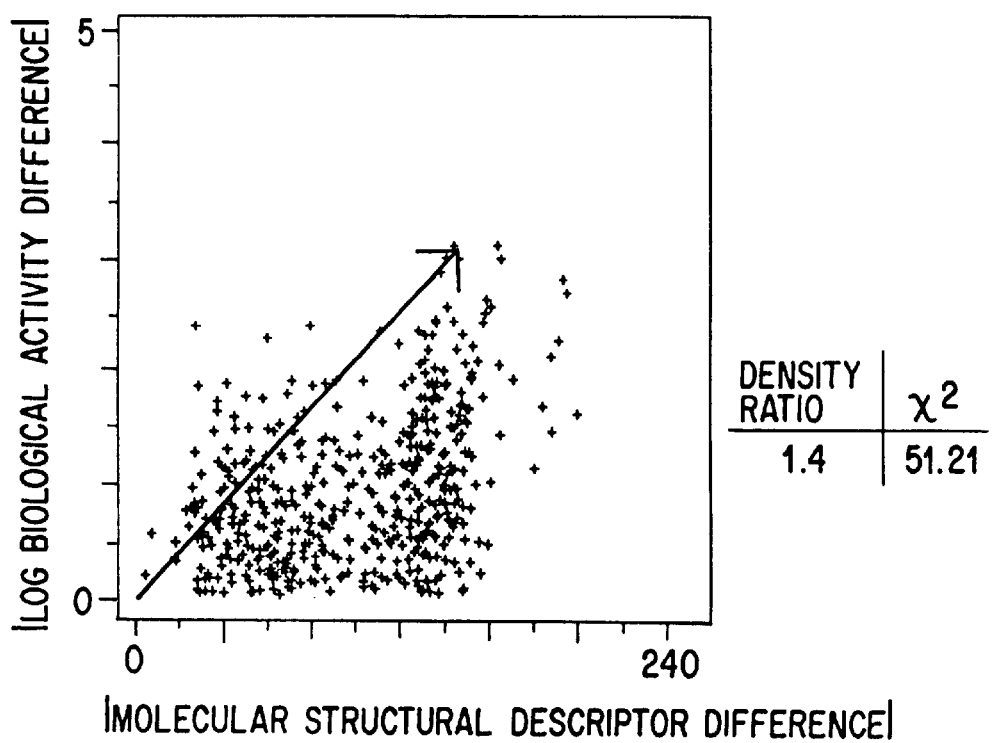
FIG. 3 shows a Patterson plot for an illustrative data set.

FIG. 3 shows a Patterson plot of a real world example. Points lying above the solid line near the Y axis reflect a metric space where a small difference in metric property (structure) produces a large difference in biological property. These points clearly violate the similarity principle/neighborhood rule. Thus, in the real world sometimes relatively small differences in structure can produce large differences in activity. If some points lie above the line, the metric is less ideal, but, clearly still useful. The major criteria and the key point to recognize is that for a metric to be valid the upper left triangle will be substantially less populated than the lower right trapezoid.

Thus, it should be recognized that for any receptor, the presence of some particular side group or combination of side groups may produce a discontinuity in the receptor response. Generally, however, any (metric) descriptor displaying the above characteristic of predominantly populating the lower right trapezoid (such as in FIG. 3) will possess the neighborhood property, and the demonstration that a metric possesses such behavior indicates the validity/usefulness of that metric. Conversely, a descriptor in which the points in the difference plot are uniformly distributed (equal density of points in ULT and LRT) does not obey the neighborhood principle and is invalid as a metric. While a brief glance at the difference plots may quickly indicate validity or non-validity, visual analysis may be misleading. As it turns out, data points in the plot frequently overlap so that visually only one point is seen where there may be two (or more). A quantitative analysis of the data distribution, therefore, yields a more accurate picture. An objective validation procedure for determining the validity/usefulness of metrics from Patterson plots of real world data including a method for assessing its statistical significance is set forth below.

Viewing the metric data in this way requires no knowledge about either the actual value of the biological activities or the actual values assigned by the descriptor under review. Because all pairwise differences are displayed, all possible gradations of molecular structural diversity and activity are represented and utilized. Consequently, there is no arbitrary lower limit set on the usable data.

B. Construction, Application, and Analysis of Patterson Plots

For purposes of objectively examining metrics for validity, it is first necessary to accurately determine the slope (placement) of the line which divides a Patterson plot into the two areas, a lower right trapezoid (LRT) and an upper left triangle (ULT). The triangle is defined by the points [0, 0], [actual metric value, max. bio. value], and [0, max. bio. value]. The trapezoid is defined by the points [0,0], [actual metric value, max. bio. value], [max. metric value, max. bio. value], and [max. metric value, 0]. For a metric to be a valid and a useful measure of molecular diversity, the density of points in the lower right trapezoid should be significantly greater than the density in the upper left triangle. To determine the correct placement of the line, the variation in the density of points is used. The line must always pass through (0,0) at the lower left corner of a Patterson plot since no change in any metric must imply no change in the biological activity. As noted earlier, considering a straight line is only a first approximation. A "perfect" metric, which totally describes the structure activity relationship of the biological system, would display a complex line reflecting the biological interaction. As a first approximation, a "useful" straight line can be found which meaningfully reflects the variation in the density of points.

The preferred search for the correct/useful line tests only those slopes which a particular data set can distinguish; specifically those drawn from [0,0] to each point [actual metric value, max bio value]. The process starts by drawing the line to a point having the smallest actual metric value [smallest metric value, max. bio. value] and continues for all of the values observed for actual metric value up to the largest [largest metric value, max. bio. value]; ie, subsequent lines are of decreasing slope. (In the limiting case of drawing the line to [largest metric value, max. bio. value] the trapezoid becomes a triangle.) When searching for the correct diagonal, it is defined to be the one which yields the highest density (number of data points/unit graph area) for a lower right triangle, which for this process is defined to have its vertices at [0, 0], [actual metric value, 0], and [actual metric value, max bio. value]. Thus, the line is identified based on the density of points under this triangle, but the evaluation ratios for the metric are calculated based on the density within the trapezoid compared to the density of the entire plot (sum of triangle and trapezoid areas). The software necessary to implement this procedure (as well as to determine the $X^2$ values to be discussed below) is contained in Appendix "A". There may be other procedures for determining the placement of the line since the line is only a first approximation. Any such procedure must meet two tests: 1) it must consistently distinguish between diversity descriptors; and 2) it must clearly distinguish/recognize meaningless diversity descriptors. The procedure described here clearly meets both tests. (The preferred search for the placement of the line is as described above. However, the lines shown in the Figures accompanying this description were found slightly differently. For the Figures, the search was started by requiring that the diagonal also pass through the point defined by the largest descriptor difference and the maximum biological activity difference [max.metric value, max. bio. value]. The line was then systematically tilted towards the vertical trying each of 100 evenly spaced steps (in terms of the Y/X ratio). As in the preferred method, the line yielding the highest density for the LRT was drawn. The line placements yielded by the two methods are not substantially different. AU numerical values reported in this specification were obtained from Patterson plots in which the preferred line drawing process was used.)

Figure 4:
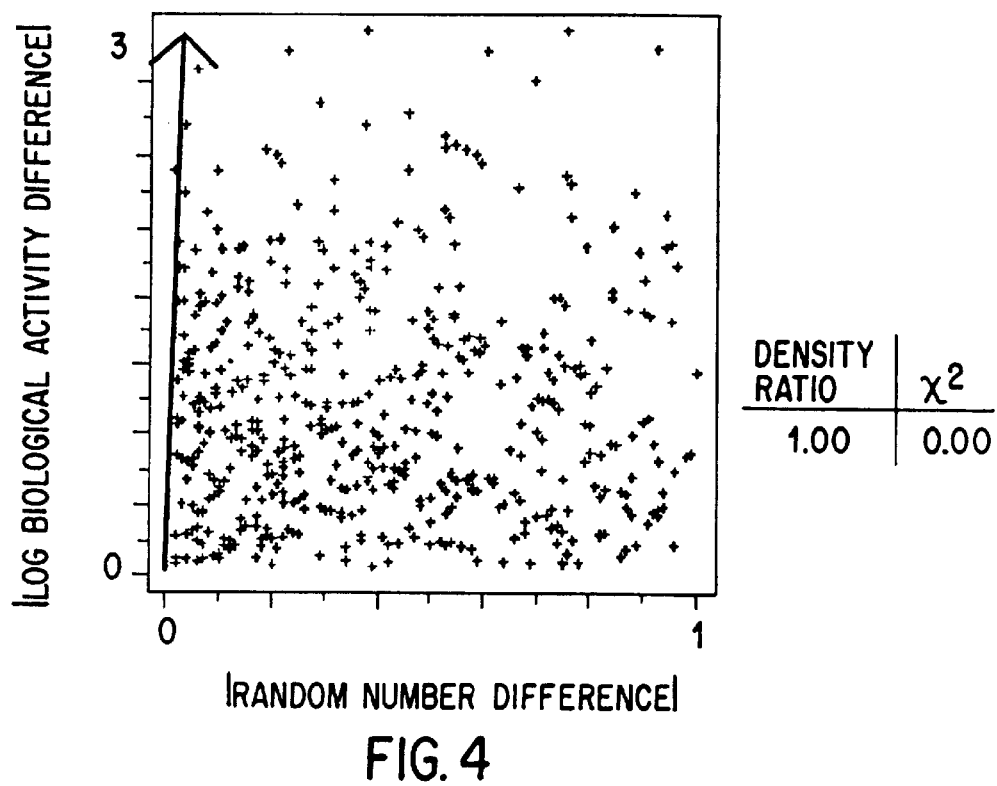
FIG. 4 shows a Patterson plot for the same data set as in FIG. 3 but where the diversity descriptor values (X axis) associated with each molecule have been replaced by random numbers.
Figure 5:
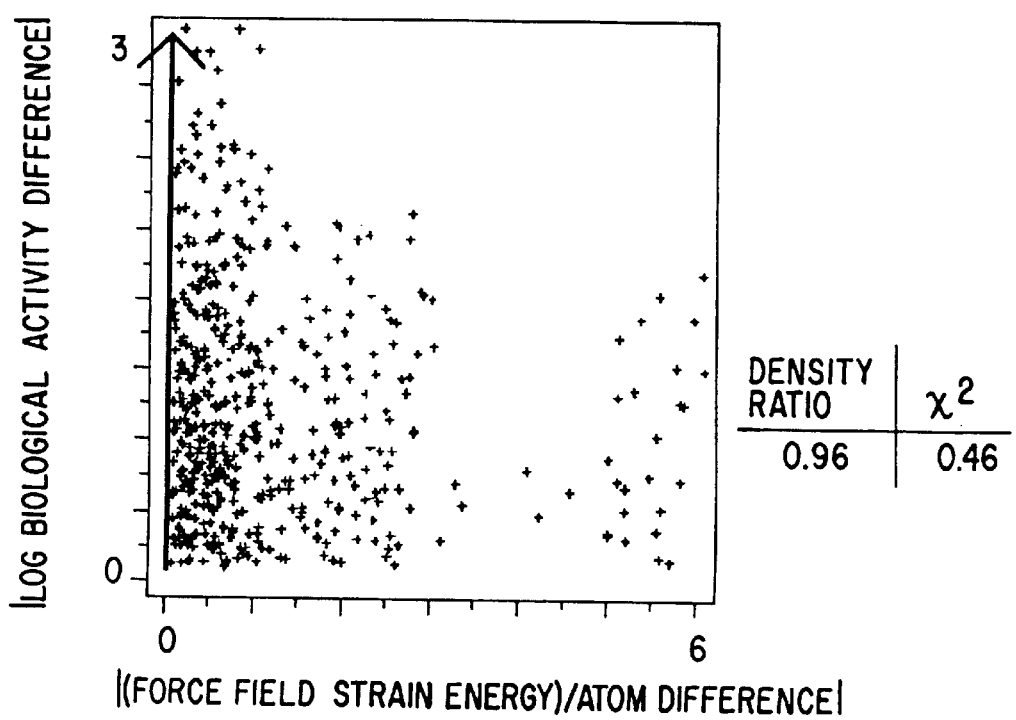
FIG. 5 shows a Patterson plot for the same data set as in FIG. 3 but where the diversity descriptor values (X axis) associated with each molecule have been replaced by a normalized force field strain energy/atom value.

The Patterson plot showing the diagonal for an exemplary data set used to validate the topomeric CoMFA descriptor (discussed in Section 4.C. below) is shown in FIG. 3. For comparison, FIGS. 4 and 5 show Patterson plots for two other variations of the same data which would not be expected to be valid molecular "measurements" useful as diversity metrics. For FIG. 4, in place of the actual metric values of FIG. 3, random numbers were generated for the diversity descriptor values of each compound and the Patterson plot generated from the differences in these random numbers. As expected from a random number assignment, no line can be found by the procedure which enriches the density in the triangle and the best ratio is not significantly different from 1.0. The best line is always reported by the procedure, which in this case corresponds to a nearly vertical line drawn to the point [minimum metric value, max. bio. value]. For randomly distributed values, this line yields the highest density for the test triangle since the X axis value and, therefore, the area of the tested triangle, is at a minimum. It is possible with some random data sets that this line, although nearly vertical, might include a couple points under the line. The placement of the line at this position is essentially an artifact of the procedure which results from an inability to find any other line which enriches the density in the tested triangle.

Because random numbers are not "real" metrics, an example of a "real molecular measurement" that is unlikely to be a valid diversity metric was examined. For the Patterson plot of FIG. 5, a force field strain energy (for the topomeric conformations using the standard Tripos force field) was calculated for each of the compounds in the same data set as was used for FIGS. 3 and 4. Because force field strain energy tends to increase with the number of atoms and thus, correlate roughly with the occasionally useful molecular weight, to normalize the value, the force field energy was divided by the number of atoms in each molecule. As expected, just as with random numbers, no optimum line could be found. This is essentially a confirmation that the points in the graph were also distributed randomly. Again, the best ratio is not significantly different from 1.0.

To objectively quantify the validity/usefulness determination, the ratio of the density of points in the lower right trapezoid to the average density of points is determined. This value can vary from somewhere above 0 but significantly less than 1, through 1 (equal density of points in each area) to a maximum of 2 (all the points in the lower right trapezoid, and the upper triangle and lower trapezoid are equal in area [imiting case of trapezoid merging into triangle]). According to the theoretical considerations discussed above, a ratio very near or equal to 1 (approximately equal densities) would indicate an invalid metric, while a ratio (significantly) greater than 1 would indicate a valid metric. The value of this ratio is set forth next to each Patterson plot in FIGS. 3 (real data), 4 (random numbers substituted), and 5 (force field energy substituted) under the column "Density Ratio". Clearly, the topomeric CoMFA data of FIG. 3 reflect a valid metric (ratio much larger than 1), while the random numbers of FIG. 4 and force field energies of FIG. 5 reflect a meaningless invalid metric (ratio very near 1). As will be discussed below, a density ratio of 1.1 is a useful threshold of validity/usefulness for a molecular diversity descriptor.

The statistical significance of the Patterson plot data can also be determined by a chi-squared test at any chosen level of significance. In this case the data are handled as:

$$X^2 = \frac{(\text{Actual } LRT \text{ Count} - \text{Expected } LRT \text{ Count})^2}{\text{Expected } LRT \text{ Count}}$$

where:

$$\text{Expected } LRT \text{ Count} = \frac{LRT \text{ Area}}{\text{Total Area}} \times \text{Total Count}$$

The chi-squared values for the Patterson plots of FIGS. 3, 4, and 5 are also set forth next to the plots under the column $X^2$. For 95% confidence limits and one degree of freedom, the chi-squared value is 3.84. The chi-squared values confirm the visual inspection and density ratio observations that the CoMFA metric is valid and the other two "constructed" metrics are invalid. A full set of topomeric CoMFA, random number, and force field data are discussed below under validation of the topomeric CoMFA descriptor.

The analysis of metrics using the difference plot of this invention is a powerful tool with which to examine metrics and data sets. First, the analysis can be used with any system and requires no prior assumptions about the range of activities or structures which need to be considered. Second, the plot extracts all the information available from a given data set since pairwise differences between all molecules are used. The prior art believed that not much information, if any, could be extracted from literature data sets since, generally, there is not a great deal of structural variety in each set. On the contrary, as will be shown below, using the Patterson plot method of this invention, a metric can be validated based on just such a limited data set. As will also be demonstrated below, metrics can be applied to literature data sets to determine the validity of the metrics. This ability opens up vast amounts of pre-existing literature data for analysis. Since in any analysis there is always a risk of making an improper determination due to sampling error when too few data sets are used or too narrow a variety of biological systems (activities) are included, the ability to use much of the available literature is a significant advance in the art. Also, the fact that the validation analysis methodology of this invention is not dependent on the study of a specific biological system, strongly implies that a validated metric is very likely to be applicable to molecular structures of unknown biological activity encountered in designing combinatorial screening libraries or making other diversity based selections. Or stated slightly differently, there is a high degree of confidence that metrics validated across many chemistries and biologies can be used in situations where nothing is known about the biological system under study.

4. Topomeric CoMFA Descriptor

Many of the prior art descriptors are essentially 2D in nature. That this is the case with the prior art probably reflects three underlying reasons. First, the rough general associations between fragments and biological properties were validated statistically decades ago.[8] Second, 2D fragment keys or "fingerprints" are widely available since they are used by all commercial molecular database programs to compare structures and expedite retrieval. Third, no one in the prior art has yet met the challenge of figuring out how to formulate and validate an appropriate three dimensional molecular structural descriptor. The situation in the prior art before the present invention is very similar to the field of QSAR about ten years ago. Then, the prior art had long recognized the desirability of three dimensional descriptors but had not been able to implement any. When a 3D technique (CoMFA) became available[9], its widespread acceptance[10] and application[11] confirmed the expected importance of 3D descriptors in general.

It has been discovered that a CoMFA approach to generating a molecular structural descriptor using a specially developed alignment procedure, topomeric alignment, produces a three dimensional descriptor of molecules which is shown to be valid by the method outlined above. In addition, this new descriptor provides a powerful tool with which to design combinatorial screening libraries. It is equally useful any time selection based on diversity from within a congeneric series is required. A full description of CoMFA and the generation of molecular interaction energies is contained in U.S. Pat. Nos. 5,025,388 and 5,307,287. The disclosures of these patents are incorporated in this Application. The usual challenge in applying CoMFA to a known set of molecules is to determine the proper alignment of the molecular structures with respect to each other. Two molecules of identical structure will have substantially different molecular interaction energies if they are translated or rotated so as to move their atoms more than about 4 Å from their original positions. Thus, alignment is hard enough when applying CoMFA to analyze a set of molecules which interact with the same biological receptor. The more difficult question is how to "align" molecules distributed in multidimensional chemistry space to create a meaningful descriptor with respect to arbitrary and unknown receptors against which the molecules will ultimately be tested. The topomeric alignment procedure was developed to correct the usual CoMFA alignments which often over-emphasize a search for "receptor-bound", "minimum energy", or "field-fit" conformations. It has been discovered that, when congenericity exists, a meaningful alignment results from overlaying the atoms that lie within some selected common substructure and arranging the other atoms according to a unique canonical rule with any resulting steric collisions ignored. When CoMFA fields are generated for molecules so aligned, it has been discovered that the resulting field differences are a valid molecular structural descriptor.

Two major advantages are achieved by applying the topomeric CoMFA metric to the reactants proposed for use in a combinatorial synthesis rather than the products resulting from the synthesis. First, the computational time/effort is dramatically reduced. Instead of analyzing for diversity a combinatorial matrix of product compounds (R1×R2×R3 . .

.) only the values for the sum of the reactants (R1+R2+R3 . . . ) need to be computed. For example, assuming 2000 reactants for R1 and 2000 reactants for R2, only 4000 calculations need be performed on the reactants versus $2000^2$ (4,000,000) if calculations on the combinatorial products were performed. Second, by identifying reactants which explore similar diversity space, it is only necessary to choose one of each reactant representative of each diversity. This immediately reduces the number of combinatorial products which need to be considered and synthesized.

A. Topomeric Alignment

Usually a CoMFA modeler seeks low energy conformations. However, if alignment with unknown receptors is desired (such as is the case in designing combinatorial screening libraries for general purpose screening), then the major goal in conformer generation must be that molecules having similar topologies should produce similar fields. In fact, topomeric CoMFA fields may be used as a validated diversity descriptor to identify molecules with similar or dissimilar structures anytime there is a problem of having more compounds than can be easily dealt with. Thus, its applicability extends well beyond its use in combinatorial chemistry to all situations where it is necessary to analyze an existing group of compounds or specify the creation of new ones. The topomeric alignment procedure is especially applicable to the design of a combinatorial screening library. Typically, as noted earlier, in the creation of combinatorially derived compounds there is often an invariant central core to which a variety of side chains (contributed by reactants of a particular class) are attached at the open valences. Within the combinatorial products, this central core tethers each of the side chains contributed by any set of reactants into the same relative position in space. In the language of CoMFA alignments, the side chains contributed by each reactant can thus be oriented by overlapping the bond that attaches the side chain to the central core and using a topomeric protocol to select a representative conformation of the side chain. Nowhere does the prior art suggest that a topomeric protocol could possibly yield a meaningful alignment. Indeed, the prior art inherently teaches away from the idea because the topomerically derived conformers often may be energetically inaccessible and incapable of binding to any receptor.

The idea of a topomeric conformer is that it is rule based. The exact rules may be modified for specific circumstances. In fact, once it is appreciated from the teaching of this invention that a particular topomeric protocol is useful (yields a valid molecular descriptor), other such protocols may be designed and their use is considered within the teaching of this disclosure.

i. General Topomeric Alignment

With the exception of two specialized situations (molecules containing chiral atoms or requiring a choice between two equivalent atoms) which will be discussed in section 4(A)(ii) below, the following topologically-based rules will generate a single, consistent, unambiguous, aligned topomeric conformation for any molecule. The software necessary to implement this procedure is contained in Appendix "A". The starting point for a topomeric alignment of a molecule is a CONCORD generated three dimensional model which is then FIT as a rigid body onto a template 3D model by least-squares minimization of the distances between structurally corresponding atoms. By convention, the template model is originally oriented so that one of its atoms is at the Cartesian origin, a second lies along the X axis, and a third lies in the XY plane.

Torsions are then adjusted for all bonds which: 1) are single and acyclic; 2) connect polyvalent atoms; and 3) do not connect atoms that are polyvalent within the template model structure since adjusting such bonds would change the template-matching geometry. Unambiguous specification of a torsion angle about a bond also requires a direction along that bond and two attached atoms. In this situation, for acyclic bonds the direction "away from the FIT atoms" is always well-defined.

The following precedence rules then determine the two attached atoms. From each candidate atom, begin growing a "path", atom layer by atom layer, including all branches but ending whenever another path is encountered (occurrence of ring closure). At the end of the bond that is closer to the FIT atoms, choose the attached atom beginning the shortest path to any FIT atom. If there are several ways to choose the atom, first choose the atom with the lowest X. If there are still several ways to choose the atom, choose next the atom with the lowest Y, and finally, if necessary, the lowest Z coordinate (coordinate values differing by some small value, typically less than 0.1 Angstroms, are considered as identical). At the other end of the bond, choose the atom beginning the path that contains any ring. When more than one path contains a ring, choose the atom whose path has the most atoms. If there are several ways to choose the path, in precedence order choose the path with the highest sum of atomic weights, and finally, if still necessary, the atom with the highest X, then highest Y, then highest Z coordinate. The new setting of the torsional value depends only on whether the bonds to the chosen atoms are cyclic or not. If neither are cyclic, the setting is 180 degrees; if one is cyclic, the setting is 90 degrees; and if both are cyclic, the setting is 60 degrees. Any steric clashes that may result from these settings are ignored.

Figure 6A:
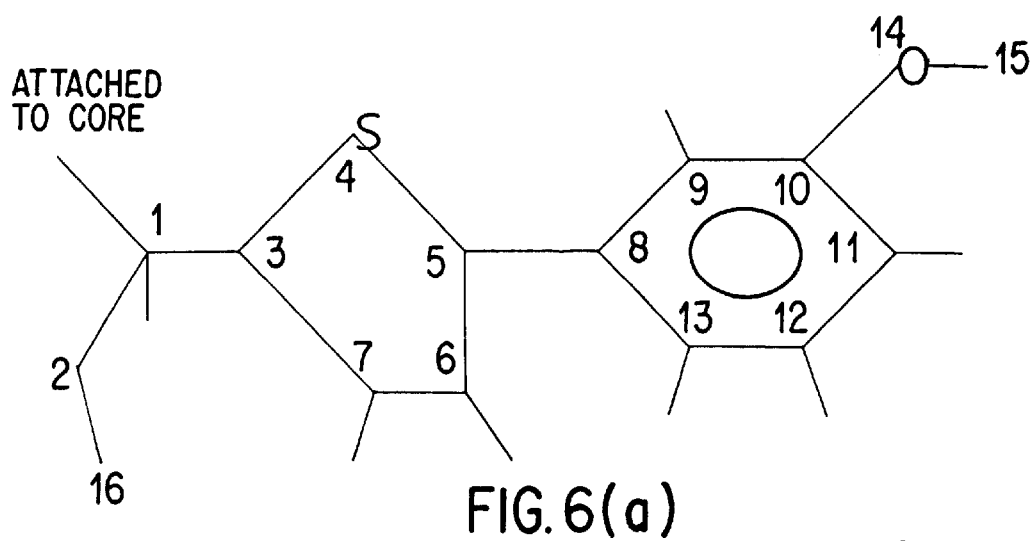
FIGS. 6a through 6d show three molecular structures numbered and marked in accordance with the topomeric alignment rule.

As an illustrative example, consider generation of the topomeric conformer for the side chain shown in FIG. 6(A), in which atom 1 is attached to some core structure by the upper left-most bond. Assuming that the alignment template for this fragment involves atom 1 only, there are three bonds whose torsions require adjustment, those connecting atoms pairs 1-3; 5-8; and 10-14. (Adding atom 3 to the alignment template would make atom 1 "polyvalent within the template model structure", so that the 1-3 bond would then not be altered.) The atom whose attached atoms will move (in the torsion adjustment) is the second atom noted in each atom pair. For example, if a torsional change were applied to the 14-10 bond instead of the 10-14 bond as shown in FIG. 6 A, all of the molecule except atoms 10, 14 and 15 (and 13 by symmetry) would move. Correspondingly, if a torsional change were applied to the 10-14 bond instead of the 14-10 bond, only atom 15 would move.

Figure 6B:
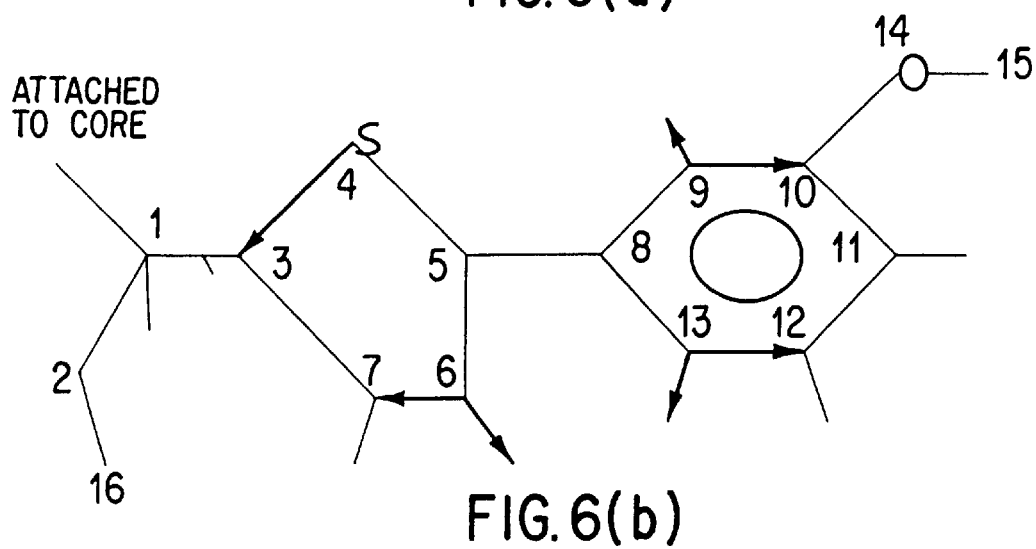
Figure 6C:
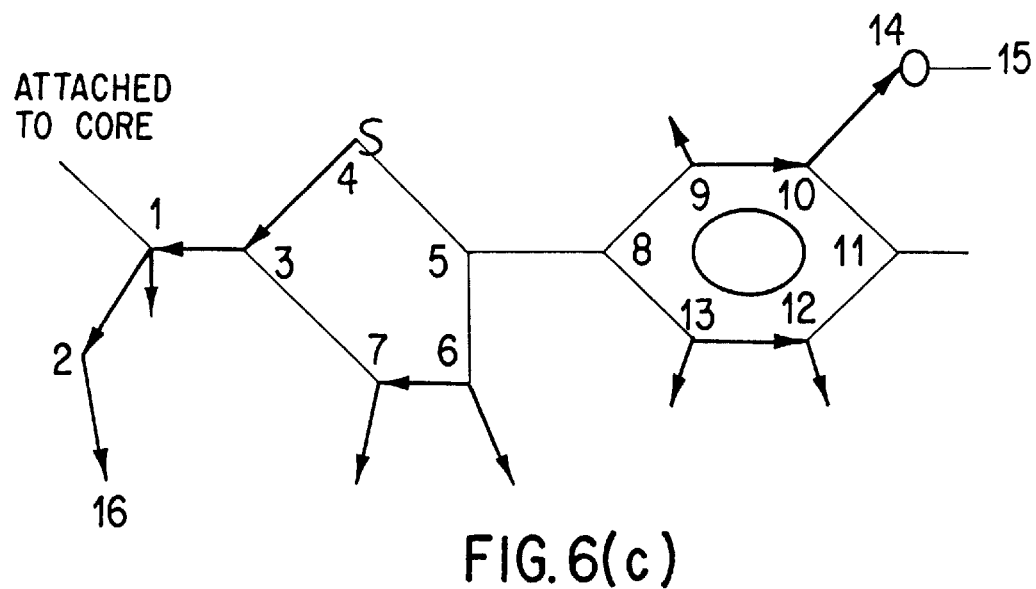

To define a torsional change, atoms attached to each of the bonded atoms must also be specified. For example, setting torsion about the bond 5-8 to 60 degrees would yield four different conformers depending on whether it is the 6-5-8-13, 6-5-8-9, 4-5-8-9, or dihedral angle which becomes 60 degrees. To make such a choice, "paths" are grown from each of the candidate atoms, in "layers", each layer consisting of all previously unvisited atoms attached to any existing atom in any path. In choosing among the four attached-atom possibilities of the 5-8 bond, FIG. 6(B) shows the four paths after the first layer of each is grown, and FIG. 6(C) shows the final paths. In FIG. 6(C), notice within the rings that, not only is the bond between 3 and 7 not crossed, but also atom 11 is not visited because the third layer seeks to include 11 from two paths, so both fail. The attached atoms chosen for the torsion definition becomes the ones that begin the highest-ranking paths according to the rules stated above. For example, in FIG. 6(C), attached atom 4 outranks atom 6 because its path is the only one reaching the alignment template, and atom 9 outranks atom 13 because its path has more atoms, so that it is the 4-5-8-9 torsion which is set to a prescribed value. For the same reasons, the other complete torsions become 9-10-14-15, attached 1-3-4 and attached 1-2-16. The other decision rules would need to be applied if atom 9 was, instead of carbon, an aromatic nitrogen (with the consequent loss of the attached hydrogen) so that the 9 and 13 paths have the same number of atoms. In this case, the 9 path still takes priority, since it has the higher molecular weight. If instead atom 14 is deleted, so that the 9 and 13 paths are topologically identical, the 9 path again takes priority because atom 9 has the same X coordinate but a larger Y coordinate than does atom 13.

As for the dihedral angle values themselves, torsion 4-5-8-9 is set to 60 degrees, because both the 4-5 and 8-9 bonds are within a ring; torsions 9-10-14-15 and attached -1-4 become 90°, because only the 3-4 and 9-10 bonds respectively are cyclic; and the attached -1-2-16 dihedral becomes 180° since none of the bonds are cyclic. It should be noted that this topomeric alignment procedure will not work with molecules containing chiral centers since, for each chiral center, two possible three dimensional configurations are possible for the same molecule, and, clearly, each configuration by the above rules would yield a different topomeric conformer.

ii. Specialized Alignment for Chiral and Equivalent Atoms

Figure 6D:
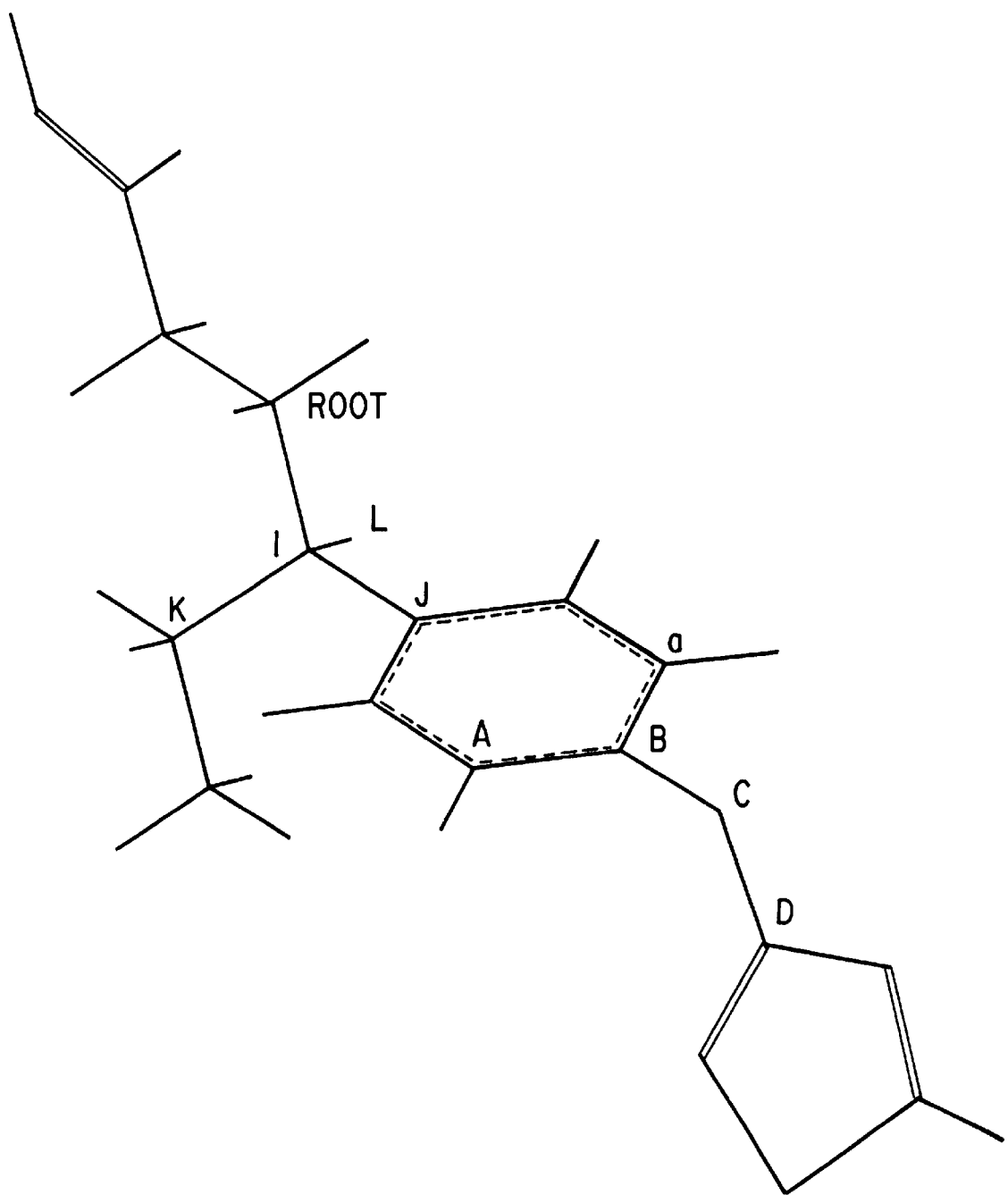

In order to resolve the ambiguity introduced by a chiral center or centers in a molecule, a specialied topermic allignment rule must be adopted. FIG. 6(D) shows a side chain whose attachment atom is marked as "Root" and in which atom I is chiral. Atom I has four non-equivalent attachments, indicated by Root, J, K, and L. Although the absolute configuration of such a chiral atom is not usually specified, an allingment methodology of an explicit 3D model must necessarily consistently select one of the two possible conformations, even if arbitrarily chosen. Proceeding as taught above, generating the topomeric conformation for the side chain leads to selection of atom J (the largest of the attachments rooted by J, K, and L) as the atom defining the Root-I torsion and thus fixes the position of J. However the relative positions of K and L remain ambiguous. Unless such "prochiral" atoms (including pyramidally hydrolyzed nitrogen) are recognized and a configuration explicitly assigned, side chains which are topologically identical may seem to be very different in shape.

The procedure used to make sure that the actual topomeric 3D models generated around chiral centers are as similar as possible is as follows: first, form a list of all such chiral centers including pyramidal nitrogen (many algorithms for doing this are described in the literature and are found in any modelling software); second, after an individual torsion has been set, as described earlier, if the third atom of the four in the torsion list is one of the chiral centers, [in FIG. 6(D) the configuration of atom I will be adjusted just after the torsion about Root-I has been set] proceed to replace the fourth atom on the torsion list [J in FIG. 6(D)] with the next highest attachment atom [following the earlier description this will be atom K in FIG. 6(D)]. If the dihedral angle value for the new torsion is greater than 180 degrees, then the reative position of atoms K and L must be exchanged To exchange the positions of atoms K and L, generate the plane defined by the second (Root) through fourth (J) atoms on the torsion that was initially set. Finally, reflect the coordinates of all the atoms attached to the third atom (I) through that plane. This topomeric procedure will generate a consistent topomeric alignment for all side chains containing chiral centers.

A second specialized topomeric alignment problem which may be enconterred is the requirement to select between two equivalent atoms. This situation is also illustrated in FIG. 6(D) where there are two candidate attachment atoms, "A" and "a", for the torsion A(a)-B-C-D. Topologically atoms "A" and "a" are identical, but a different position for the five-membered ring, hence a very different shape, will be generated depending on whether "A" or "a" is used to assign the torsion of A(a)-B-C-D. The following rule is used to ensure that the choice between "A" and "a" is made consistently. Measure the two dihedral angles defined by the atom lists Root-B-C-A and Root-B-C-a. (Although these atoms are obviously not directly connected, the dihedral angle values are well-defined.) Of the two possibilities, select the atom to define the torsion for which the torsional value lies between 170 and 350 degrees.

Using the selection rules set out above, the critical point is that the use of a single topomerically aligned conformer in computing a CoMFA three dimensional descriptor has been found to yield a validated descriptor. While other approaches to conformer selection such as averaging many representative conformers or classifying a representative set by their possible interactions with a theoretically averaged receptor (such as in the polyomino docking) are possible, it has been found that topomerically aligned conformers yield a validated descriptor which, as will be seen below, produces clustering highly consistent with the accumulated wisdom of medicinal chemistry.

B. Calculation of CoMFA and Hydrogen Bonding Fields

The basic CoMFA methodology provides for the calculation of both steric and electrostatic fields. It has been found up to the present point in time that using only the steric fields yields a better diversity descriptor than a combination of steric and electrostatic fields. There appear to be three factors responsible for this observation. First is the fact that steric interactions—classical bioisosterism—are certainly the best defined and probably the most important of the selective non-covalent interactions responsible for biological activity. Second, adding the electrostatic interaction energies may not add much more information since the differences in electrostatic fields are not independent of the differences in steric fields. Third, the addition of the electrostatic fields will halve the contribution of the steric field to the differences between one shape and another. This will dilute out the steric contribution and also dilute the neighborhood property. Clearly, reducing the importance of a primary descriptor is not a way to increase accuracy. However, it is certainly possible that in a given special situation the electrostatic contribution might contribute significantly to the overall "shape". Under these unique circumstances, it would be appropriate to also use the electrostatic interaction energies or other molecular characterizers, and such are considered within the scope of this disclosure. For instance, in some circumstances a topomeric CoMFA field which incorporates hydrogen bonding interactions, characterized as set forth below, may be useful.

The steric fields of the topomerically aligned molecular side chain reactants are generated almost exactly as in a standard CoMFA analysis using an $sp^3$ carbon atom as the probe. As in standard CoMFA, both the grid spacing and the size of the lattice space for which data points are calculated will depend on the size of the molecule and the resolution desired. The steric fields are set at a cutoff value (maximum value) as in standard CoMFA for lattice points whose total steric interaction with any side-chain atom(s) is greater than the cutoff value. One difference from the usual CoMFA procedure is that atoms which are separated from any template-matching atom by one or more rotatable bonds are set to make reduced contributions to the overall steric field. An attenuation factor (1–"small number"), preferably about 0.85, is applied to the steric field contributions which result from these atoms. For atoms at the end of a long molecule, the attenuation factor produces very small field contributions (ie: $[0.85]^N$) where N is the number of rotatable bonds between the specified atom and the alignment template atom. This attenuation factor is applied in recognition of the fact that the rotation of the atoms provides for a flexibility of the molecule which permits the parts of the molecule furthest away from the point of attachment to assume whatever orientation may be imposed by the unknown receptor. If such atoms were weighted equally, the contributions to the fields of the significant steric differences due to the more anchored atoms (whose disposition in the volume defined by the receptor site is most critical) would be overshadowed by the effects of these flexible atoms.

The derivation of a hydrogen-bond field is slightly different from the standard CoMFA measurement. The intent of the hydrogen-bonding descriptor is to characterize similarities and differences in the abilities of side chains to form hydrogen-bonds with unknown receptors. Like the successful use of the topomeric conformation to characterize steric interactions, the topomeric conformation is also an appropriate way to characterize the spatial position of a side chain's hydrogen-bonding groups. However, unlike a steric field, hydrogen-bonding is a spatially localized phenomenon whose strength is also difficult to quantitative. Therefore, it is appropriate to represent a hydrogen-bonding field as a bitset, much like a 2D fingerprint, or as an array of 0 or 1 values rather than as an array of real numbers like a CoMFA field.

The hydrogen-bonding loci for a particular side chain are specified using the DISCO approach of "extension points" developed by Y. Martin[12] and coworkers, wherein, for example, a carbonyl oxygen generates two hydrogen-bond accepting loci at positions found by extending a line passing from the oxygen nuclei through each of the two "lone-pair" locations to where a complementary hydrogen-bond donating atom on the receptor would optimally be. It is not possible with a bitset representation to attenuate the effects of atoms by the number of intervening rotatable bonds. Instead, uncertainty about the location of a hydrogen-bonding group can be represented by setting additional bits for grid locations spatially adjacent to the single grid location that is initially set for each hydrogen-bonding locus. In other words, each hydrogen-bonding locus sets bits corresponding to a cube of grid points rather than a single grid point. The validation results shown in Table 4 were obtained for a cube of 27 grid locations for each hydrogen bonding locus. The single bitset representing a topomeric hydrogen-bonding fingerprint has twice as many bits as there are lattice points, in order to discriminate hydrogen-bond accepting and hydrogen bond-donating loci. The difference between two topomeric hydrogen-bonding fingerprints is simply their Tanimoto coefficient which now represents a difference in actual field values. Software which implements the hydrogen-bonding field calculations is provided in Appendix "B".

C. Validation of Topomeric CoMFA Descriptor

Figure 7A:
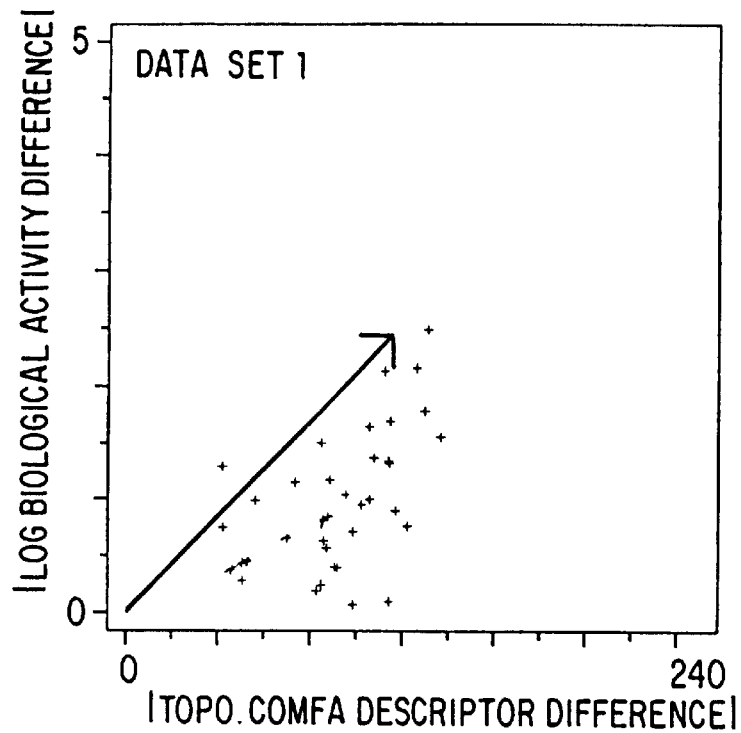
FIGS. 7a through 7t are a complete set of Patterson plots for the twenty data sets used for the validation studies of the topomeric CoMFA descriptor.
Figure 7B:
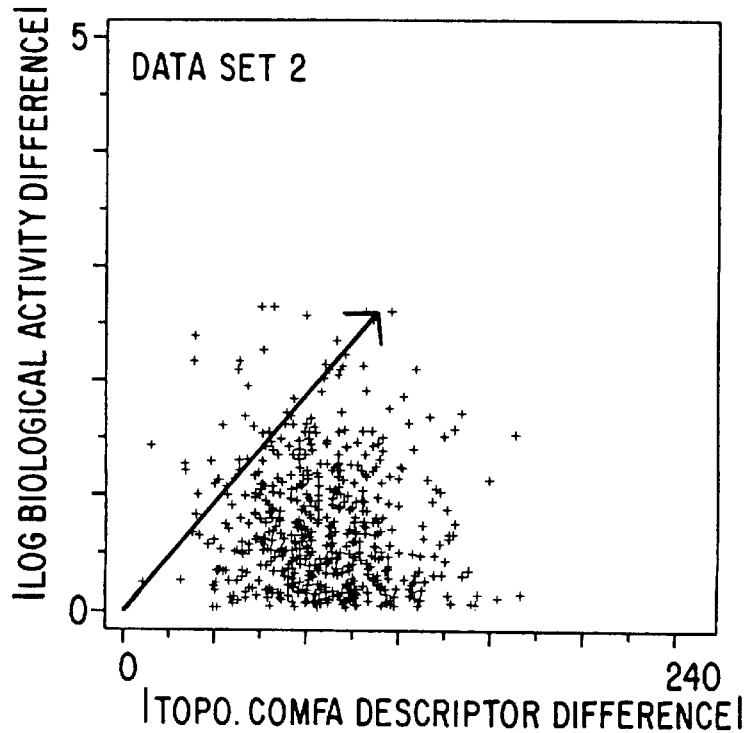
Figure 7C:
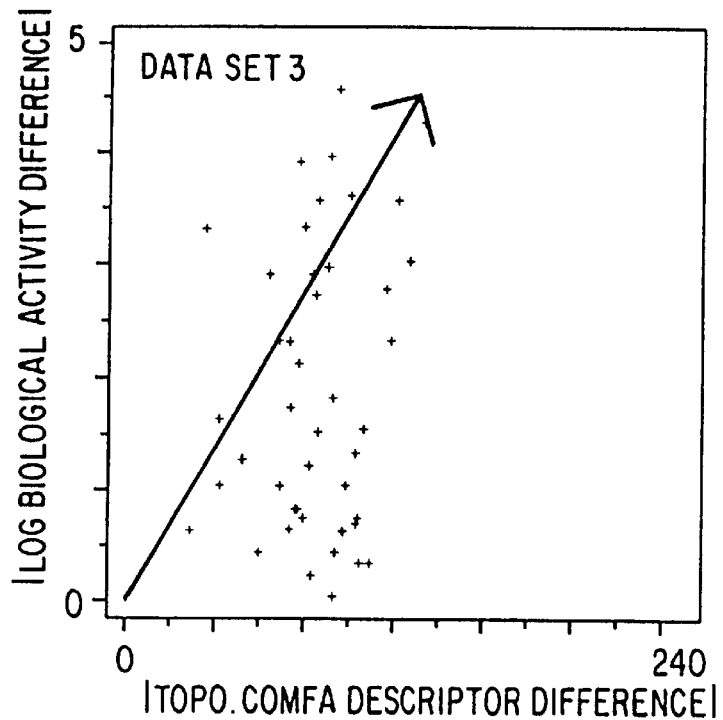
Figure 7D:
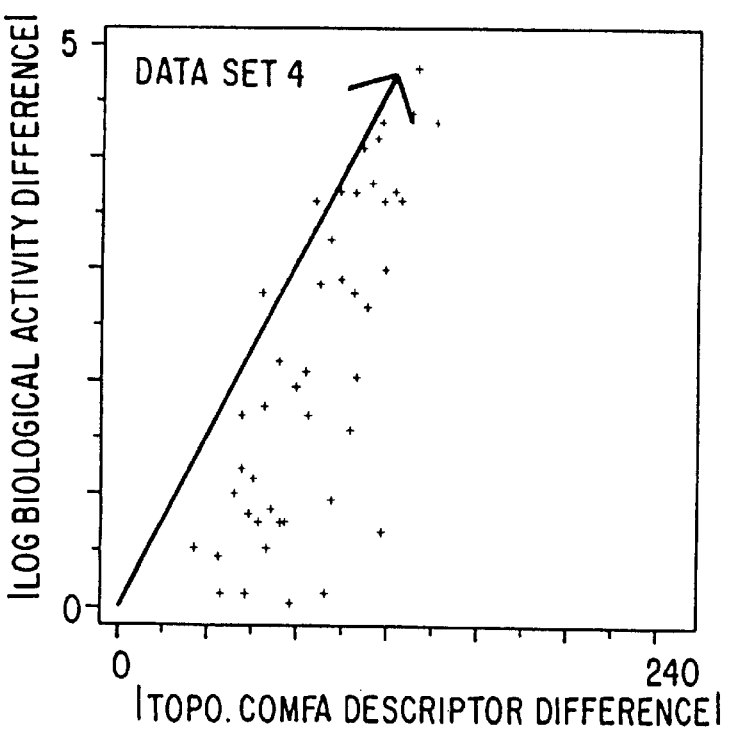
Figure 7E:
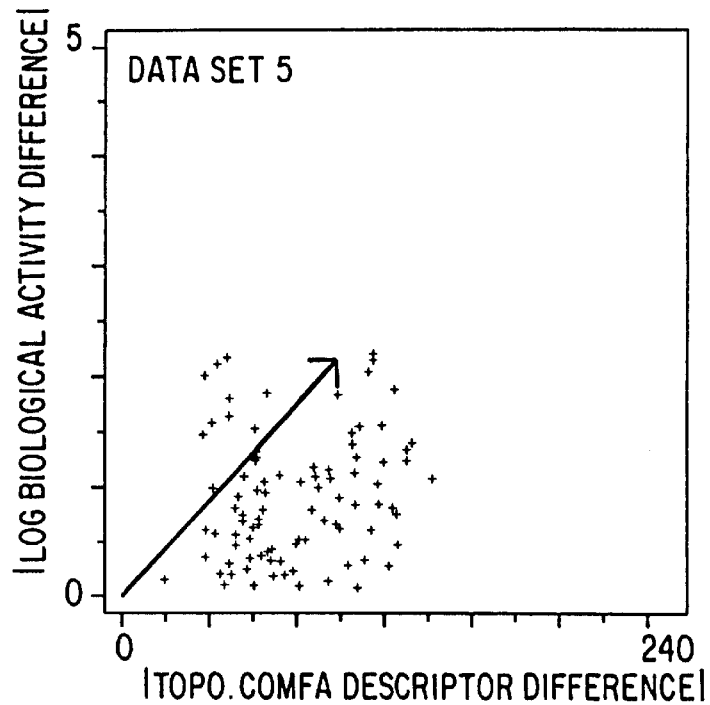
Figure 7F:
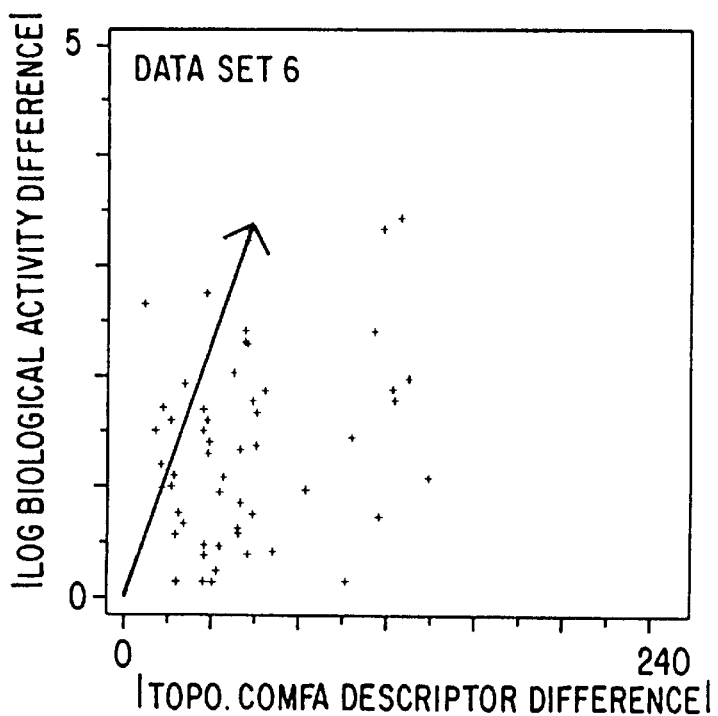
Figure 7G:
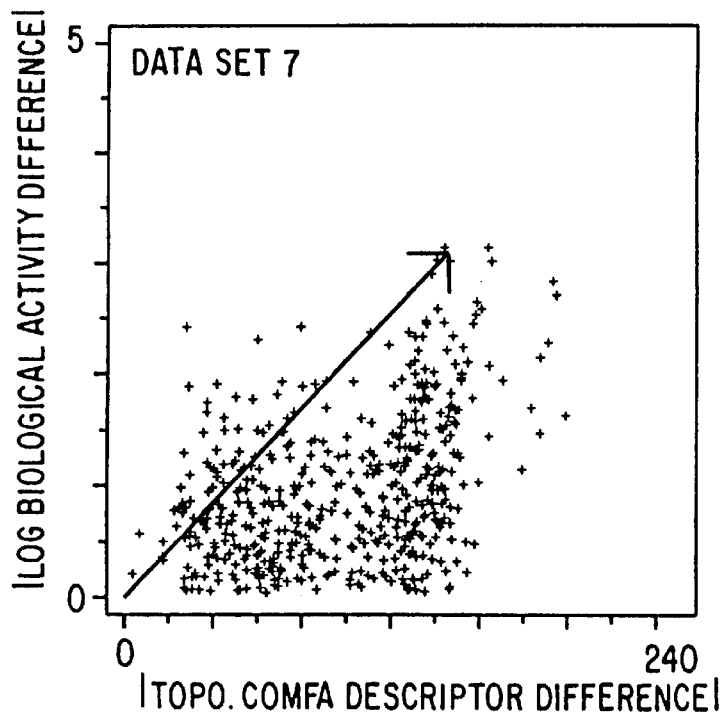
Figure 7H:
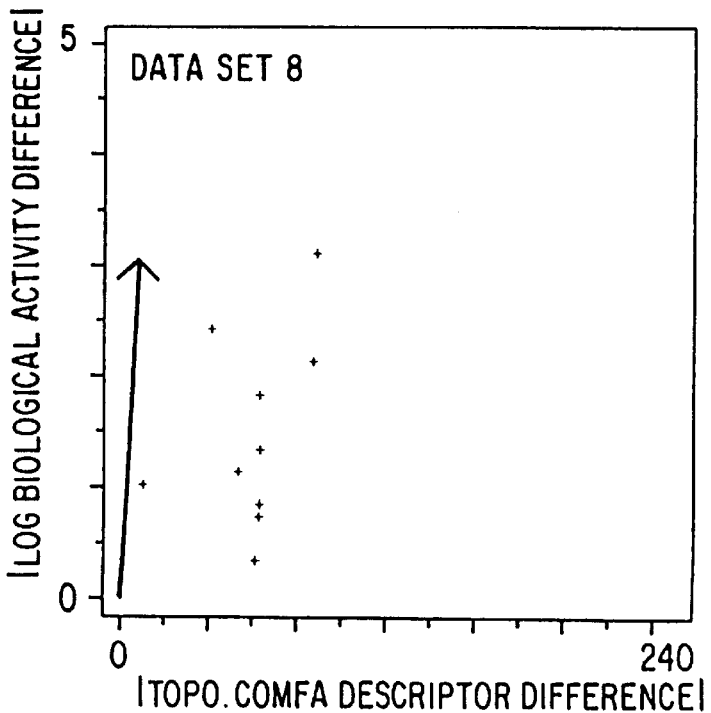
Figure 7I:
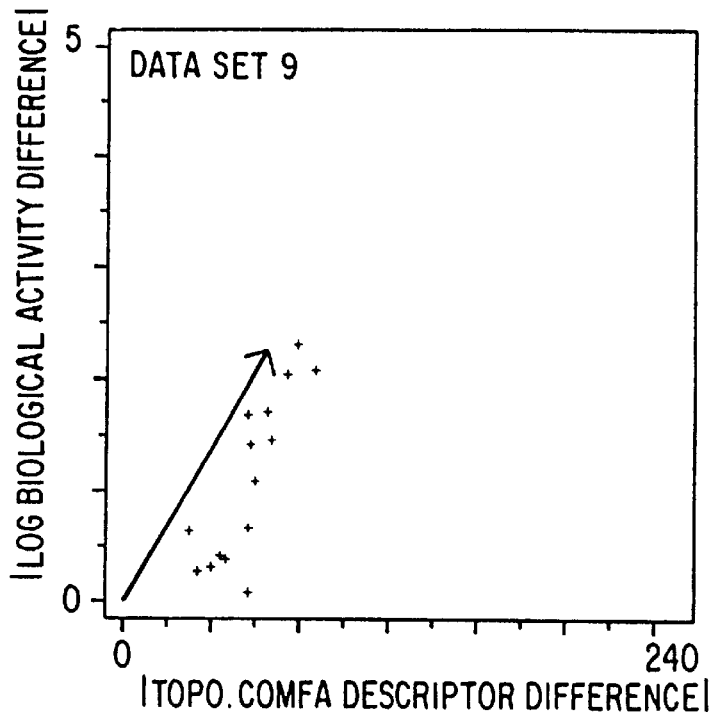
Figure 7J:
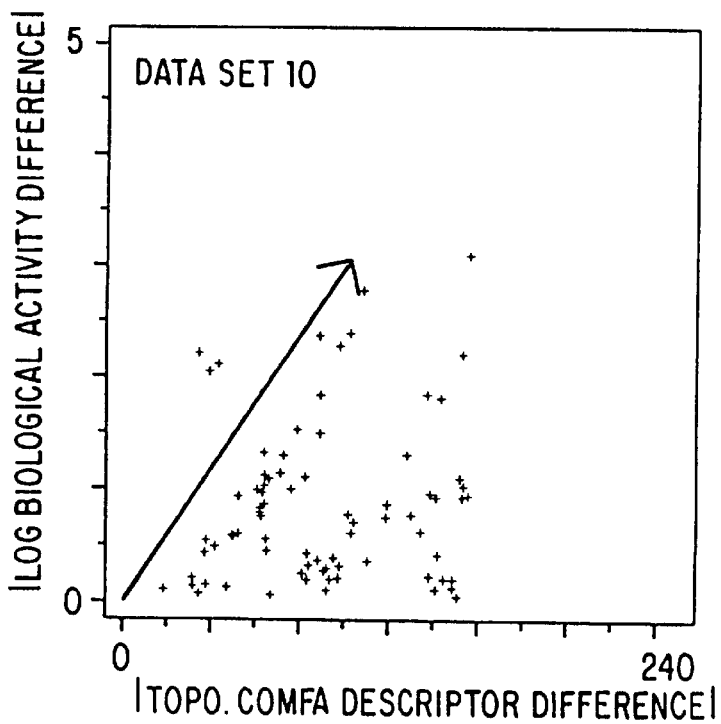
Figure 7K:
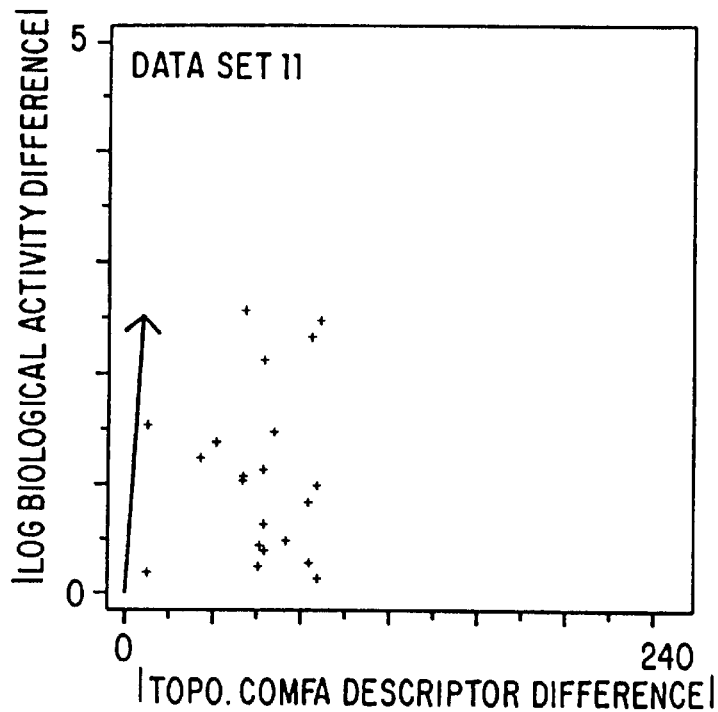
Figure 7L:
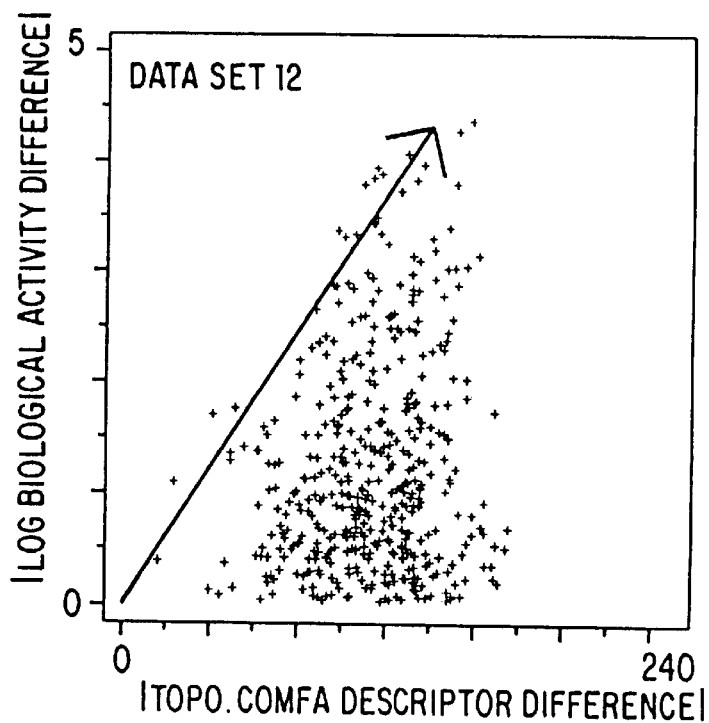
Figure 7M:
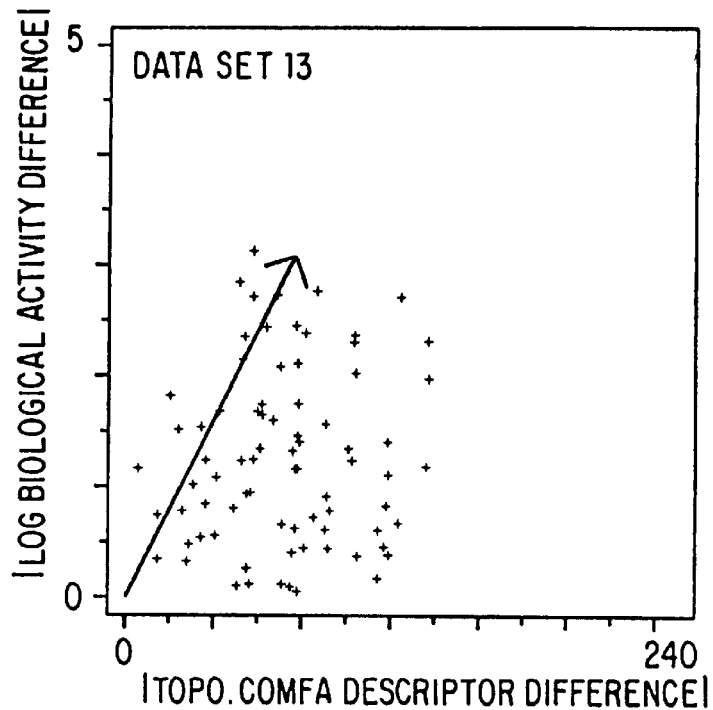
Figure 7N:
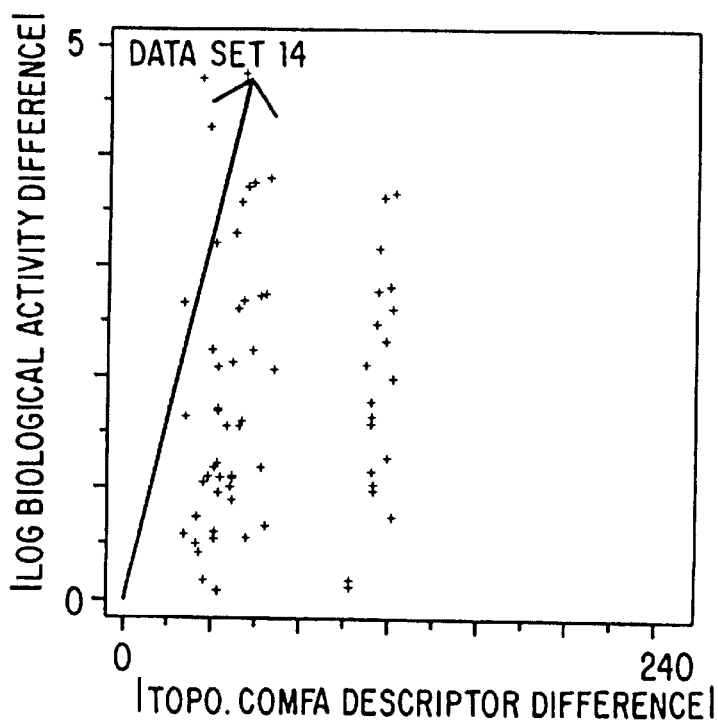
Figure 7O:
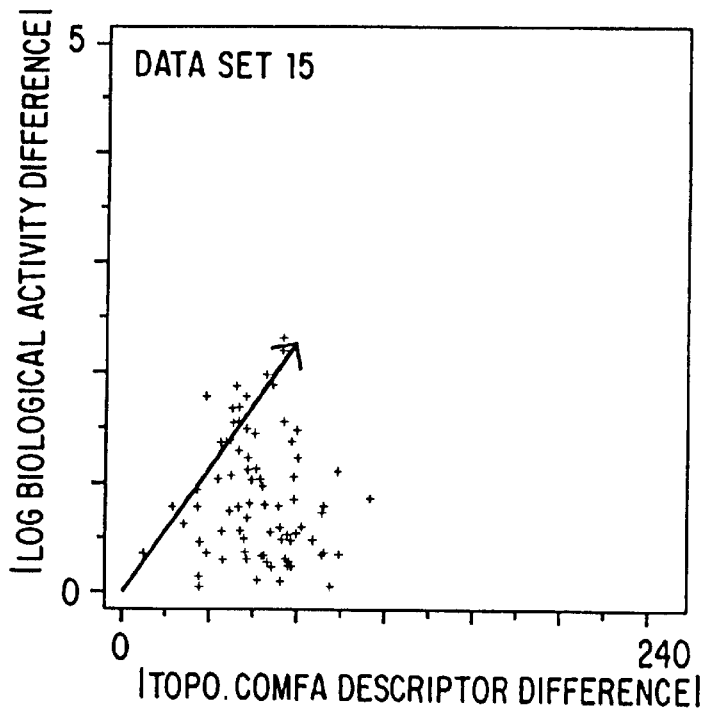
Figure 7P:
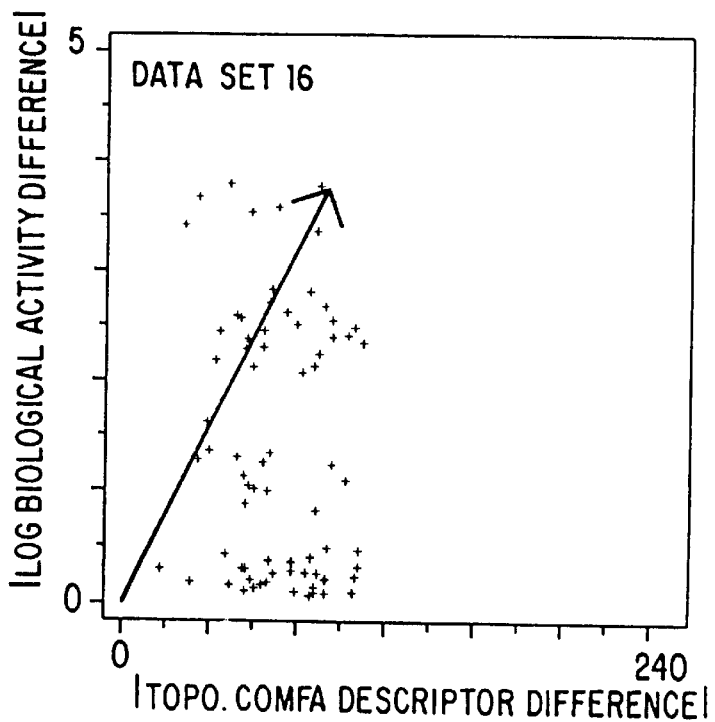
Figure 7Q:
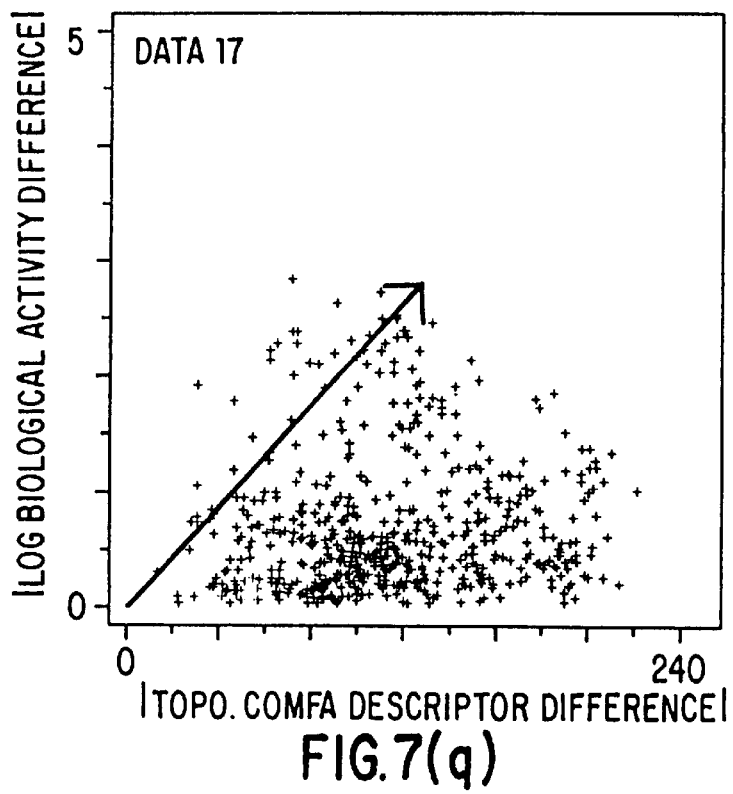
Figure 7R:
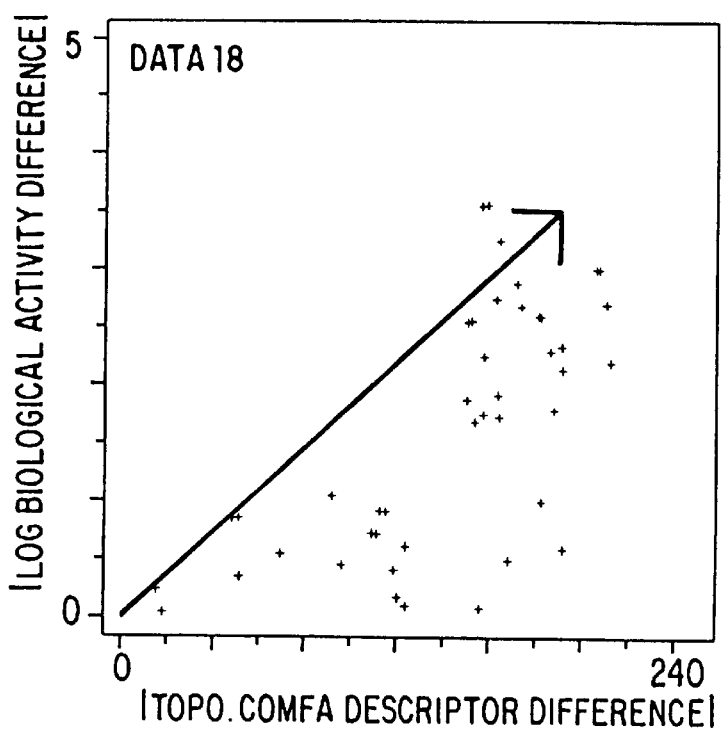
Figure 7S:
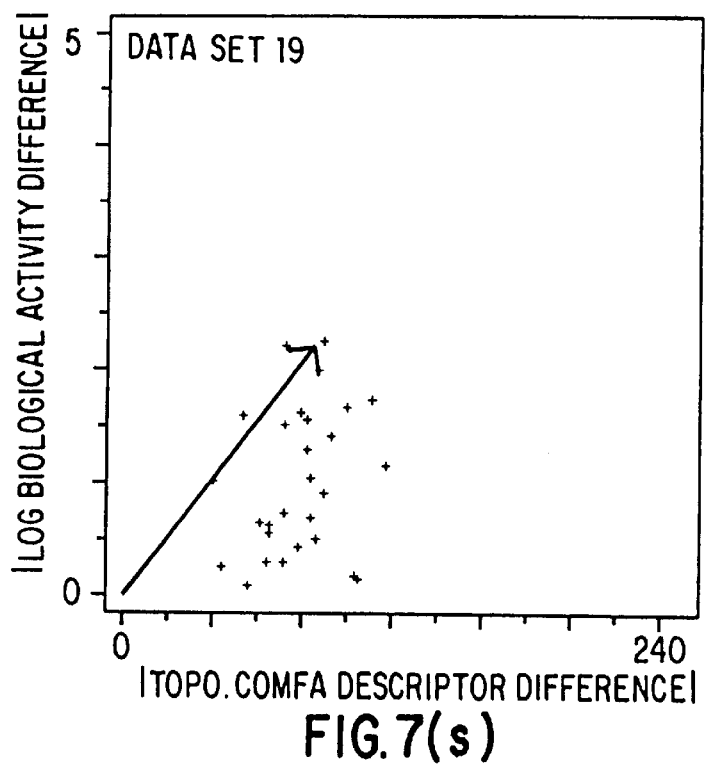
Figure 7T:
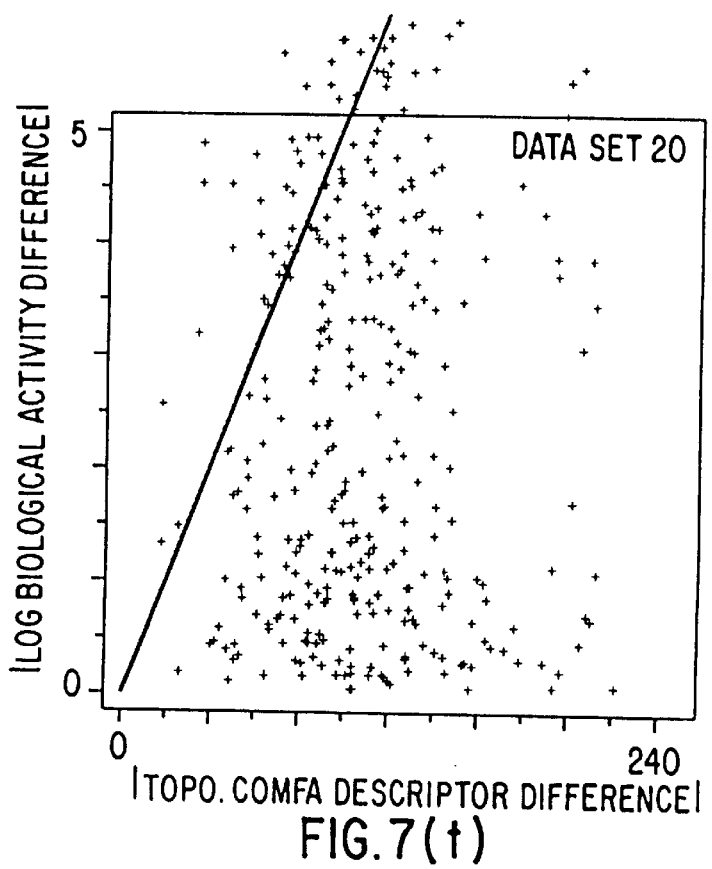

The validity of topomerically aligned CoMFA fields as a molecular structural descriptor, which can be used to describe the diversity of compounds, was confirmed on twenty data sets randomly chosen from the recent biochemical literature. The data sets spanned several different types of ligand-receptor binding interactions. The only criteria for the data sets were: 1) the reported biological activities must span at least two orders of magnitude; 2) the structural variation must be "monovalent" (only one difference per molecule); 3) the molecules contain no chiral centers; and 4) no page turning was required for data entry in order to reduce the likelihood of entry errors. Each data set was analyzed independently. The identification of the data sets is set forth in Appendix "C". The structural variations of the side chains of the core templates were entered as the Sybyl Line Notations of the corresponding thiols. (Sybyl Line Notations [SLNs] define molecular structures.) An -SH was substituted for the larger common template portion of each molecule and provided the two additional atoms needed for 3D orientation. According to the validation method of this invention the Patterson plots constructed as discussed above for the twenty data sets are shown in FIGS. 7(a)–7(t).

In 17 of the 20 cases, visual inspection of the plots suggests that the density of points in the lower right trapezoid is, indeed, greater than the density in the upper left triangle as predicted for a metric descriptor obeying the neighborhood rule. Also, for reasons noted earlier, some points do fall above the line as would be expected for the real world. However, the relative rarity of points in the upper left triangle of the plots indicates that "small steric field differences are not likely to produce large differences in bioactivity", the neighborhood rule. Thus, the distribution of points in the Patterson plots across all the randomly selected data sets is remarkably consistent with the theoretical prediction for a valid/useful diversity metric. It can be easily seen that the topomeric CoMFA metric is validated/useful.

Table 1 contains the density ratios from the quantitative analysis of the twenty data sets. The density ratios of the two test metrics (random number assignments and molecular force field energy divided by number of atoms for the diversity descriptor values) described earlier are presented for comparison. $X^2$ values reflecting the statistical significance of the ratios are also set forth next to the corresponding ratios.

TABLE 1

Patterson Plot Ratios and Associated $X^2$

| No. | Reference | CoMFA Ratio | CoMFA $X^2$ | Random Ratio | Random $X^2$ | Energy Ratio | Energy $X^2$ |
|---|---|---|---|---|---|---|---|
| 1 | Uehling | 1.71 | 10.27 | 0.98 | 0.01 | 0.98 | 0.02 |
| 2 | Strupczewski | 1.39 | 57.33 | 1.01 | 0.02 | 0.97 | 0.47 |
| 3 | Siddiqi | 1.44 | 6.26 | 0.92 | 0.01 | * | * |
| 4 | Garratt-1 | 1.72 | 13.01 | 1.02 | 0.02 | 1.00 | 0.00 |
| 5 | Garratt-2 | 1.37 | 8.02 | 1.04 | 0.11 | 0.97 | 0.07 |
| 6 | Heyl | 1.04 | 0.08 | 0.99 | 0.01 | 0.97 | 0.05 |
| 7 | Cristalli | 1.40 | 51.21 | 1.00 | 0.00 | 0.96 | 0.46 |
| 8 | Stevenson | 0.95 | 0.02 | 0.98 | 0.00 | 0.98 | 0.01 |
| 9 | Doherty | 1.63 | 3.54 | 1.02 | 0.01 | 0.96 | 0.02 |
| 10 | Penning | 1.45 | 10.33 | 0.99 | 0.01 | 1.00 | 0.00 |
| 11 | Lewis | 0.95 | 0.04 | 1.05 | 0.05 | 0.97 | 0.02 |
| 12 | Krystek | 1.64 | 119.92 | 1.00 | 0.00 | 0.97 | 0.49 |
| 13 | Yokoyama-1 | 1.18 | 1.88 | 1.00 | 0.00 | 0.93 | 0.41 |
| 14 | Yokoyama-2 | 1.23 | 2.62 | 1.02 | 0.02 | 0.99 | 0.01 |
| 15 | Svensson | 1.27 | 3.72 | 1.04 | 0.00 | 0.99 | 0.00 |
| 16 | Tsutsumi | 1.38 | 6.50 | 0.94 | 0.02 | 0.96 | 0.06 |

TABLE 1-continued

Patterson Plot Ratios and Associated $X^2$

| No. | Reference | CoMFA Ratio | CoMFA $X^2$ | Random Ratio | Random $X^2$ | Energy Ratio | Energy $X^2$ |
|---|---|---|---|---|---|---|---|
| 17 | Chang | 1.34 | 45.55 | 1.01 | 0.12 | 0.99 | 0.03 |
| 18 | Rosowsky | 1.71 | 12.46 | 0.95 | 0.10 | 1.00 | 0.00 |
| 19 | Thompson | 1.47 | 3.96 | 1.06 | 0.09 | 1.00 | 0.00 |
| 20 | Depreux | 1.22 | 10.85 | 0.98 | 0.07 | * | * |
|  | MEAN | 1.38 | 18.38 | 1.00 | 0.03 | 0.98 | 0.12 |
|  | STND. DEVIATION | 0.24 | 29.43 | 0.04 | 0.04 | 0.02 | 0.19 |

*Data sets 3 and 20 are not reported for the force field energy because one of the structures in each data set (in the topomeric conformation) had a very strained energy greater than 10 kcal/mole-atom, which produced a discontinuously large metric difference.

The chi-squared distributions for 1 degree of freedom are:

| P = | .75 | .90 | .95 | .99 | .999 |
|---|---|---|---|---|---|
| $X^2$ = | 1.32 | 2.71 | 3.84 | 6.64 | 10.83 |

Figure 8A:
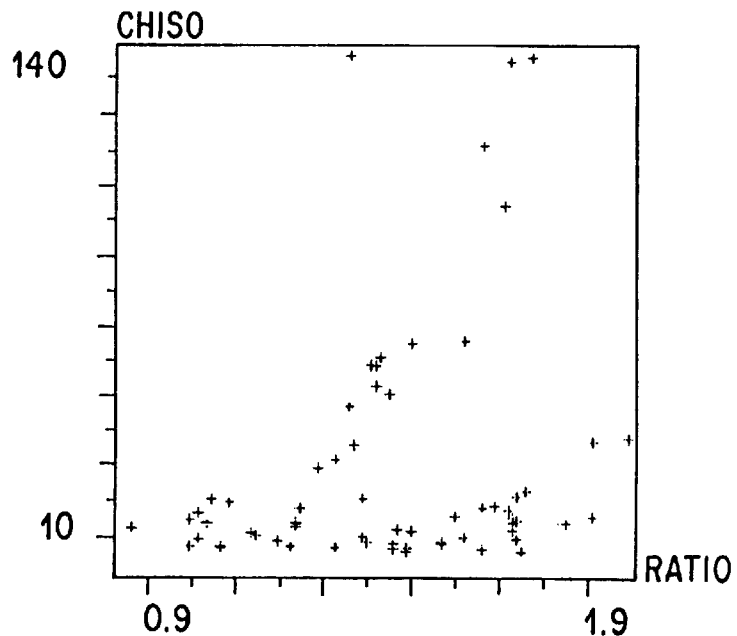
FIGS. 8a and 8b show the two scatter plots displaying the relation between $X^2$ values and their corresponding density ratio values for the tested metrics over the twenty random data sets.
Figure 8B:
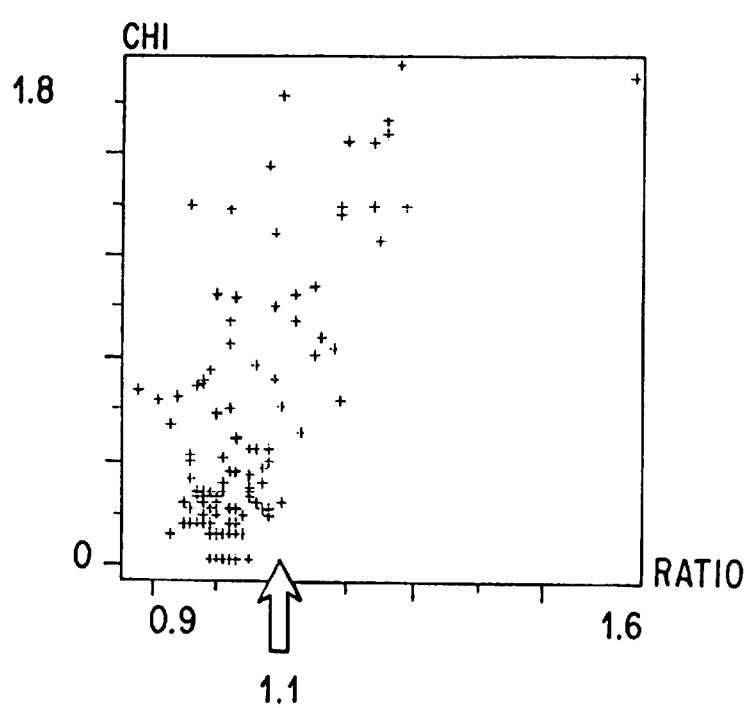

Typically, a confidence level of 95% is considered appropriate in statistical measures A metric is considered valid/useful for an individual data set if the Patterson plot ratio is greater than 1.1; that is, there is greater than a 10% difference in the density between the ULT and LRT. The use of 1.1 as a decisional criteria is confirmed by an examination of the scatter diagrams of $X^2$ values versus their corresponding ratios as shown in FIGS. 8A and 8B. (The value of X is actually plotted in FIG. 8B in order to separate the data points.) FIG. 8A shows the plot of $X^2$s having a value of greater than 3.84 (95% confidence limits) versus their corresponding ratios, while FIG. 8B shows the plot of $X^2$s (plotted as $\sqrt{X^2}$) having a value less than 3.84 versus their corresponding ratios. A ratio value of greater than 1.1 (FIG. 8A) clearly includes most of the statistically significant ratios, while a ratio value of less than 1.1 clearly includes most of the statistically insignificant ratios. While this is not a perfect dividing point and there is some overlap, there is also some distortion of the $X^2$ values due to limited population sizes as discussed below. Overall, the value of 1.1 provides a reasonable decision point.

As noted earlier, the validity of a metric should not be determined on the basis of one data set from the literature. A single literature data set usually presents only a limited range of structure/activity data and examines only a single biological activity. To obtain a proper sense of the overall validity/quality of a metric, its behavior over many data sets representing many different biological activities must be considered. It should be expected for randomly selected data sets that due to biological variability, an otherwise valid metric may appear invalid for some particular set. An examination of the data in Table 1 confirms this observation.

Except for data sets 6, 8, and 11, the ratios in Table 1 clearly confirm for the topomeric CoMFA metric that the density of points in the LRT is greater than in the ULT, and the $X^2$ values confirm the significance of the plots. At the same time, the data for the two test metrics clearly demonstrates with great sensitivity that this validation technique yields exactly the results expected for a meaningless metric; specifically, a density ratio substantially equal to 1 and no significance as determined by the $X^2$ test. Contrary to accepted notions in the prior art, with the discovery of this invention, random literature data sets can be used to validate metrics. The type of publicly unavailable data set (as will be discussed in relation to the Abbott data set below) where the bioactivity or inactivity for each molecule in the set has been experimentally verified is not required.

Sets 6, 8, and 11 are the exceptions which help establish the rule. It is realistic to expect that randomly selected data sets would include some where molecular edge (typically a collision with receptor atoms) or other distorting effects would be present. For set 6, one experimental value was so inconsistent with other reported values that the authors even called attention to that fact. In addition to a problematic experimental value, all the structural changes are rather small but some of the biological changes are fairly large. Something very unusual is clearly happening with this system. For set 8, there is simply not enough data. Only 5 compounds (10 differences) were included and this proved insufficient to analyze even with the sensitivity of the Patterson plot. For data set 11, there were two contributing factors. First, the data set was small (only 7 compounds). Second, this set is a good example of an edge effect where a methyl group protruding from the molecules interacts with the receptor site in a unique manner which dramatically alters the activity.

Generally, the $X^2$ values support the significance (or lack of significance) of the ratio values. However, for data sets 9, 13, 14, and 15 the 95% confidence limit is not met. As with all statistical tests, $X^2$ is sensitive to the sample size of the population. For these data sets the N was simply too low. This sensitivity is well demonstrated by the difference in $X^2$ for sets 14 and 20. The ratio values of the two sets are virtually identical, but the $X^2$s differ significantly since set 14 has few points and set 20 many points. Thus, $X^2$ may be used to confirm the significance of a ratio value, but, on the other hand, can not be used to discredit a ratio value when too few data points are present. It can be clearly seen that the topomeric CoMFA metric appears to define a useful dimensional space (measures chemistry space) better for some of the target sets than for others.

As was discussed above, a metric need not be perfect to be valid. Even using an imperfect metric significantly increases the probability that molecules can be properly characterized based on structural differences. As the quality of the metric increases, the probability increases. Thus, metrics which appear valid by the above analysis with respect to only a few test data sets are still useful. Metrics, like topomeric CoMFA, which are valid for 85% (17/20) of the data sets yield a higher probability that structurally diverse molecules can be identified.

Only with respect to data sets 6, 8, and 1 does the topomeric CoMFA metric not appear to provide a useful measure. Considering the fact that some of the data sets have limited samples and that a very wide range of biological interactions is represented, it is not unexpected that random variations like this will appear. The critically important aspect of this analysis is the fact that the metric is valid over a truly diverse range of types of ligand-substrate interactions. This strongly confirms its generally applicability as a valid measure of the diversity of molecules which can be used to select optimally diverse molecules from large data sets such as for use in combinatorial screening library design.

Another important aspect of the invention can be derived from these plots. Upon close examination it can be seen that molecules having topomeric CoMFA differences (distances) of less than approximately 80–100 generally have activities within 2 log units of each other. This provides a quantitative definition of the radius of an area encompassing molecules possessing similar characteristics (similarly diverse) in topomeric CoMFA metric space—the neighborhood radius. Because the topomeric CoMFA metric is a valid molecular structural descriptor, it is known that molecules with similar structure and activity will cluster in topomeric CoMFA space. Topomeric CoMFA distances can, therefore, be usefully used as a diversity measure in selecting which molecules of a proposed combinatorial synthesis should be retained in the combinatorial screening library in order to have a high probability that most of the diversity available in that combinatorial synthesis is represented in the library. Thus, for a combinatorial screening library, only one example of a molecular pair having a pairwise distance from the other of less than approximately 80–100 kcal/mole (belonging to the same diversity cluster) would be included. However, every molecule of a pair having a pairwise distance greater than approximately 80–100 would be included. Of course, the "fineness" of the resolution (the radius of the neighborhood in metric space) can be changed by using a different activity difference. The Patterson plot permits by direct inspection the determination of a neighborhood distance appropriate to any chosen biological activity difference. It is suggested, however, that for a reasonable search of chemistry space for biologically significant molecules, a difference of 2 log units is appropriate. The exact value chosen be adjusted to the circumstances. Clearly, the opportunity for real world perturbing effects to dominate the measure is magnified by using less than 2 log units difference in biological activity. This is another example of the general signal to noise ratio problem often encountered in measurements of biological systems. For more accurate signal detection less perturbed by unusual effects, the data sets would ideally contain biological activity values spread over a wider range than what is usually encountered. The neighborhood radius predicted from an analysis of the topomeric CoMFA metric can now be used to cluster molecules for use in selecting those of similar structure and activity (such as is desired in designing a combinatorial screening library of optimal diversity).

The teachings of this disclosure so far may be summarized as follows: 1) a generalizable method for validating metric descriptors has been taught; 2) a specific descriptor, topomeric CoMFA, has been described; and 3) the topomeric CoMFA descriptor has been validated over a diverse sampling of different types of biological interactions from published data sets.

The extraordinary power inherent in the validation method to quantitatively determine a significant neighborhood radius is further demonstrated by a remarkable result obtained in the analysis of a data set of potential reactants for a combinatorial synthesis (all 736 commercially available thiols) from the chemical literature. The results were obtained by "complete linkage" hierarchical cluster analysis of the resulting steric field matrices, using "CoMFA_STD" or "NONE" scaling. (CoMFA_STD implies block standardization of each field, but without rescaling of the individual "columns" corresponding to particular lattice points, which here produces the same clusters as no scaling). For clustering the "distance" between any two molecules is calculated as the root sum of the squared differences in steric field values over all of the lattice intersections defined by the CoMFA "region".

In this example, cluster analysis using topomeric CoMFA fields produced a classification of reagents that makes sense to an experienced medicinal chemist. For example, when the topomerically aligned CoMFA fields of the 736 thiols are clustered, stopping when the smallest distance between clusters is about 91 kcal/mole (within the "neighborhood" distance of 80–100 found for these fields in the validation studies), 231 discrete clusters result differing from each other in steric size by at least a —CH$_2$— group. Upon inspection of the clustering, an experienced analyst will immediately recognize that at this clustering level of 231, a natural break occurs, ie: the separation between cluster level 231 and level 232 was greater than any encountered between levels 158 and 682. Further inspection of these results showed that, with perhaps ten exceptions, each cluster contained only compounds having a very similar 2D topology or connectivity, while different clusters always contained compounds having dissimilar 2D topology. Indeed, so logical was the grouping that it was possible to provide a characteristic and distinctive systematic name for each of the 238 clusters using mostly traditional or 2D chemical nomenclature as shown in Appendix "D". It is striking that this entirely automatic clustering procedure, based only on differences among the topomeric steric fields of 3D models of single conformers, generates a classification that coincides so well with chemical experience as embodied in an independently generated 2D nomenclature. From a pragmatic point of view, this result may also be said to validate the validation procedure in the eyes of an experienced medicinal chemist who will tend to judge a metric by whether its assessments of molecular similarity and diversity agree with his/her own experience.

The critical aspect of this clustering result is that the structurally most logical clustering was generated with a nearest neighbor separation of 91, in the middle of the 80–100 neighborhood distance determined from the validation procedure to be a good measure of similarity among the molecules in topomeric CoMFA metric space. That is, the neighborhood distance of approximately 80–100 (corresponding to an approximate 2 log biological difference) predicted from the topomeric CoMFA validation, generates, when used in a clustering analysis, logical systematic groupings of similar chemical structures. The exact size of the neighborhood radius useful for clustering analysis will vary depending upon: 1) the log range of activity which is to be included; and 2) the metric used since, in the real world, different metrics yield different distance values for the same differences in biological activity. As seen, the topomeric CoMFA metric can be used to distinguish diverse molecules from one another—the very quantitative definition of diversity lacking in the prior art which is necessary for the rationale construction of an optimally diverse combinatorial screening library.

The discovered validation method of this invention is not limited to the topomeric CoMFA field metric but is generalizable to any metric. Thus, once any metric is constructed, its validity can be tested by applying the metric to appropriate literature data sets and generating the corresponding Patterson plots. If the metric displays the neighborhood behavior and is valid/useful according to the analysis of the Patterson plots set forth above, the neighborhood radius is easily determined from the Patterson plots once an activity difference is selected. This neighborhood radius can then be used to stop a clustering analysis when the distance between clusters approaches the neighborhood radius. The resulting clusters are then representative of different aspects of molecular diversity with respect to the clustered property/metric. It should be noted that a metric, by definition, is only used to describe something which has a difference on a measurement scale. This necessarily implies a "distance" in some coordinate system. Mathematical transformations of the distances yielded by any metric are still "distances" and can be used in the preparation of the Patterson plots. For instance, the topomeric CoMFA field distances could be transformed into principal component scores and would still represent the same measure.

Since the validity of the metric is not dependent on the particular chemical/biological assays used to establish its validity, the metric can be applied to assemblies of chemical compounds of unknown activity. Clustering of these assemblies using the validated neighborhood radius for the metric will yield clusters of compounds representative of the different aspects of molecular diversity found in the assemblies. (It should be understood that active molecules for any given assay may or may not reside in more than one cluster, and the cluster(s) containing the active compound(s) in one assay may not include the active compound(s) in a different assay.)

As mentioned above, when designing an efficient combinatorial screening library, one wishes to avoid including more than one molecule which is representative of the same structural diversity. Therefore, if a single molecule is included from each cluster derived as above, a true sample of the diversity represented by all the molecules is achieved without overlap. This is what is meant by designing a combinatorial screening library for optimal diversity. The methodologies of the present invention for the first time enable the achievement of such a design.

5. Tanimoto Fingerprint Descriptor

There are other measures of molecular similarity which are not metrics, that is, they do not correspond to a distance in some coordinate system but for which differences between molecules can be calculated. One such measure is the Tanimoto[13] fingerprint similarity measure. This is one of the 2D measurements frequently used in the prior art to cluster molecules or to partially construct other molecular descriptors. (Technically descriptors containing a Tanimoto term are not metrics since the Tanimoto is not a metric). 2D fingerprint measures were originally constructed to rapidly screen molecular data bases for molecules having similar structural components. For the present purposes, a string of 988 has been found convenient and sufficiently long. A Tanimoto 2D fingerprint similarity measure (Tanimoto coefficient) between two molecules is defined as:

$$\frac{\text{No. Of Bits Occuring} \in \text{Both Molecules}}{\text{No. Of Bits} \in \text{Either Molecule}}$$

The Tanimoto fingerprint simply expresses the degree to which the substructures found in both compounds is a large fraction of the total substructures.

A. Neighborhood Property

At an American Chemical Society meeting in April, 1995, Brown, Martin, and Bures[3] of Abbott Laboratories presented clustering data generated in an attempt to determine which, if any, of the common descriptors available in the prior art produced "better clustering". "Better clustering" was defined as a greater tendency for active molecules to be found in the same cluster. One of the measures used was the Tanimoto 2D fingerprint coefficient calculated from the structures of the entire molecules (not just the side chains). Proprietary and publicly unavailable data sets were used by the Abbott group which covered a large number of compounds for which the activity or lack of activity in four assays had been experimentally verified over many years of pharmacological research. Although used as an analytical tool to measure clustering effectiveness and not itself a focus of the presentation, one of the graphs Martin presented plotted the "proportion of molecular pairs in which the second molecule is also active" against the "pairwise Tanimoto similarity between active molecules and all molecules" (hereafter referred to as a "sigmoid plot"). From the resulting graph Martin et al. essentially found that if the Tanimoto coefficient of molecule A (an active molecule) with respect to molecule B is greater than approximately 0.85, then there was a high probability that molecule B will also be active; ie., the activity of molecule B can be usefully predicted by the activity of molecule A and vice versa. While not recognized or taught by the Abbott group at the time, the present inventors recognized that, for a very restricted data set, the Abbott group had data suggesting that the Tanimoto coefficient displayed a neighborhood property.

B. Applicability of Tanimoto to Different Biological Systems

In order to determine whether the Tanimoto coefficient reflects a neighborhood property over a range of different biological assays, 11,400 compounds from Index Chemicus containing 18 activity measures with 10 or more structures were analyzed. (Index Chemicus covers novel compounds reported in the literature of 32 journals.) Lack of a reported activity was assumed to be an inactivity although, in reality, the absence of a report of activity probably means that the compound was just untested in that system. For comparison purposes, this assumption is a more difficult test in which to discriminate a trend than with the Abbott data base where it was experimentally known whether or not a molecule was active or inactive. However, all that is absolutely needed for this analysis is a high likelihood of having compounds that are "similar enough" in fingerprints to also be "similar enough" in biological activity. The converse, "similar biological activity must have similar fingerprints", is patently untrue and is not tested. Table 2 shows the structures and activities analyzed.

TABLE 2

Index Chemicus Activities

| Set No. | No. Anal. | Biological Activity |
|---|---|---|
| 1 | 30 | Antianaphylactic |
| 2 | 12 | Antiasthmatic |
| 3 | 71 | Antibacterial |
| 4 | 16 | Anticholinergic |
| 5 | 55 | Antifungal |
| 6 | 17 | Anti-inflammatory |
| 7 | 21 | Antimicrobial |
| 8 | 13 | B-adrenergic |
| 9 | 21 | Bronchodilator |
| 10 | 34 | Ca Antagonistic |
| 11 | 18 | Cytotoxic |
| 12 | 133 | Enzyme Inhibiting |
| 13 | 210 | Nematocidal |
| 14 | 12 | Opioid Rcptr. Bind |
| 15 | 39 | Platelet Aggr. Inh. |
| 16 | 11 | Radioprotective |
| 17 | 13 | Renin Inhibiting |
| 18 | 11 | Thrombin Inhib. |

Figure 9A:
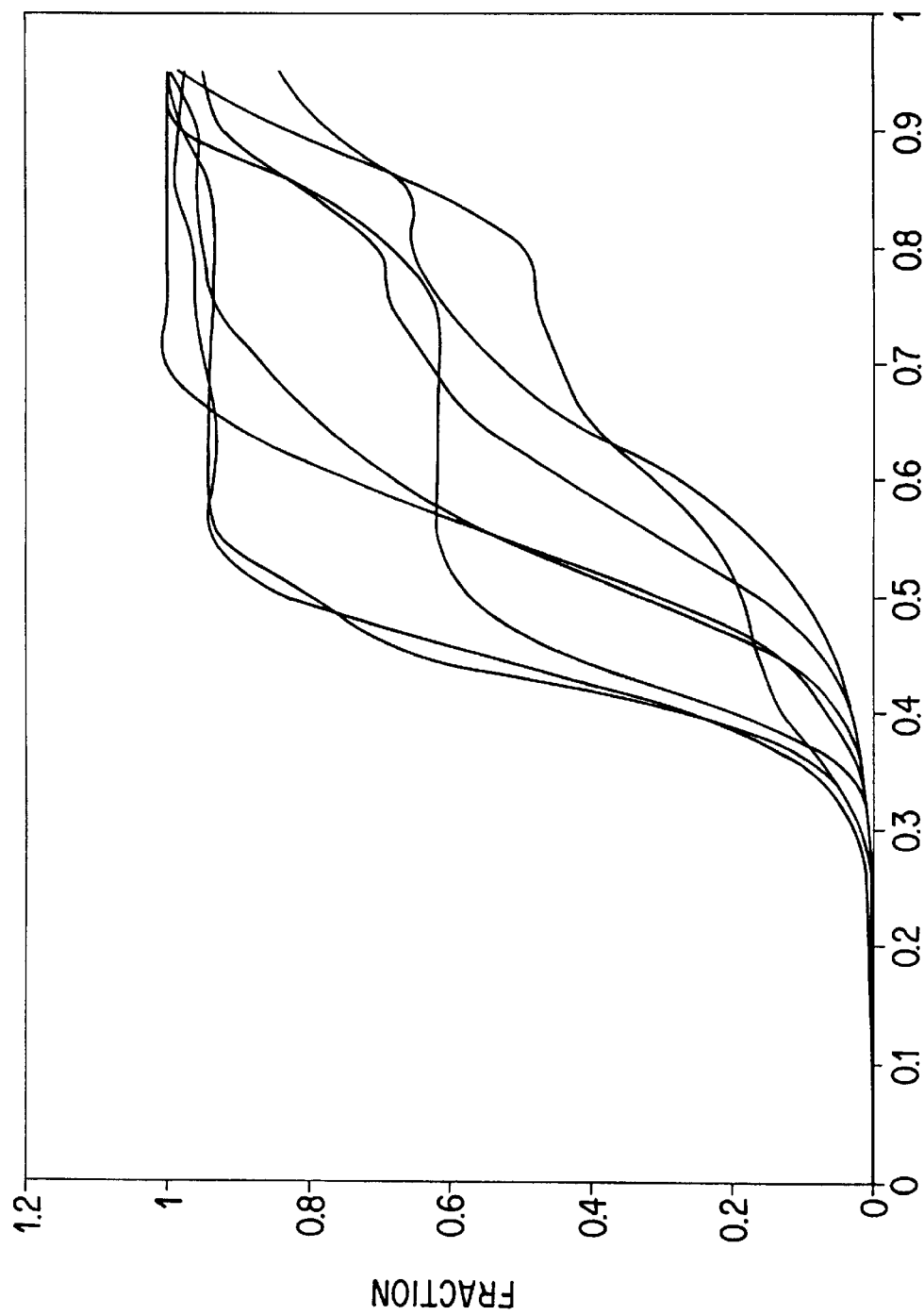
FIGS. 9a through 9c shows the graphs of the Tanimoto similarity measure vs. the pairwise frequency of active molecules for 18 groups examined from Index Chemicus.
Figure 9B:
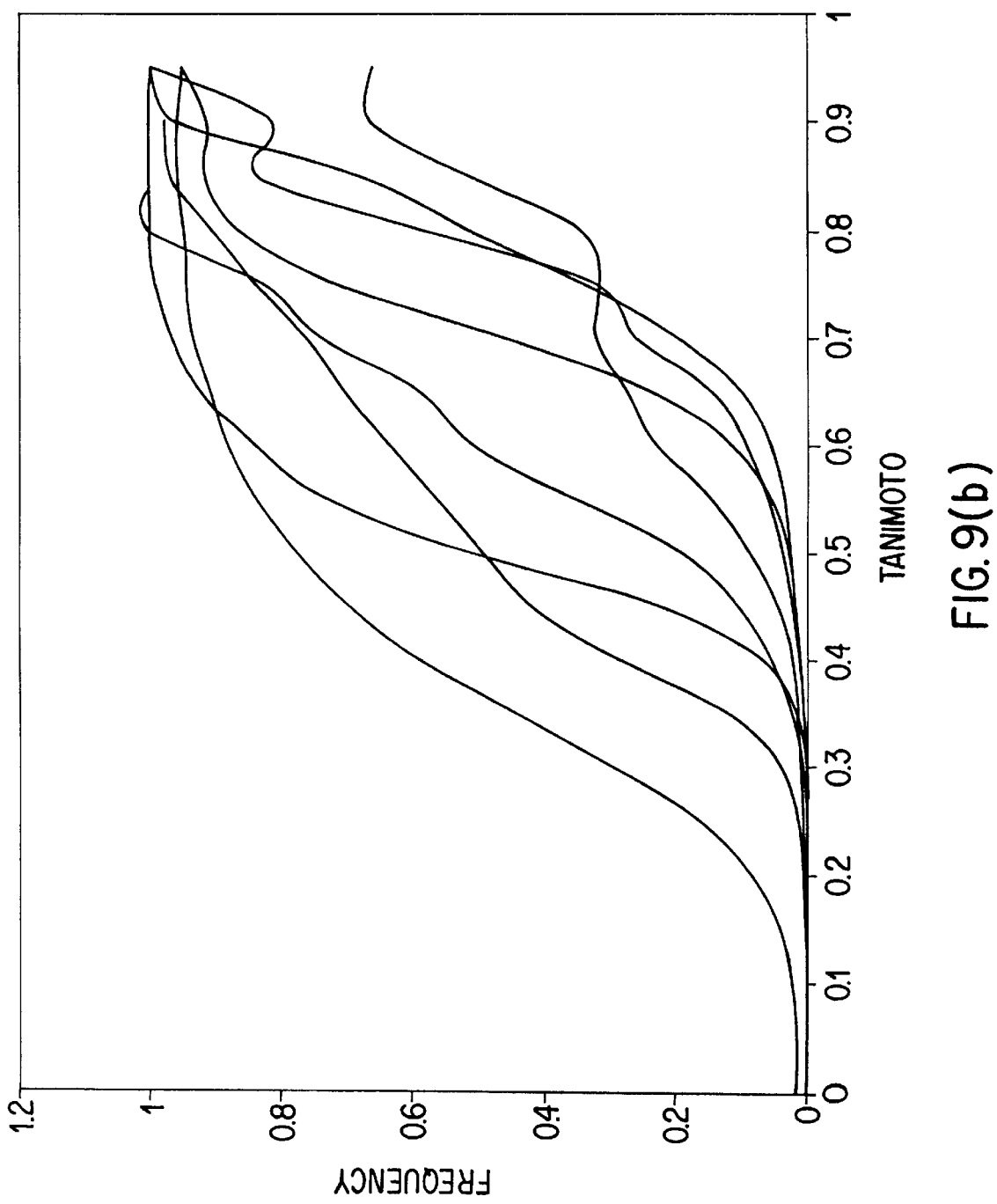
Figure 9C:
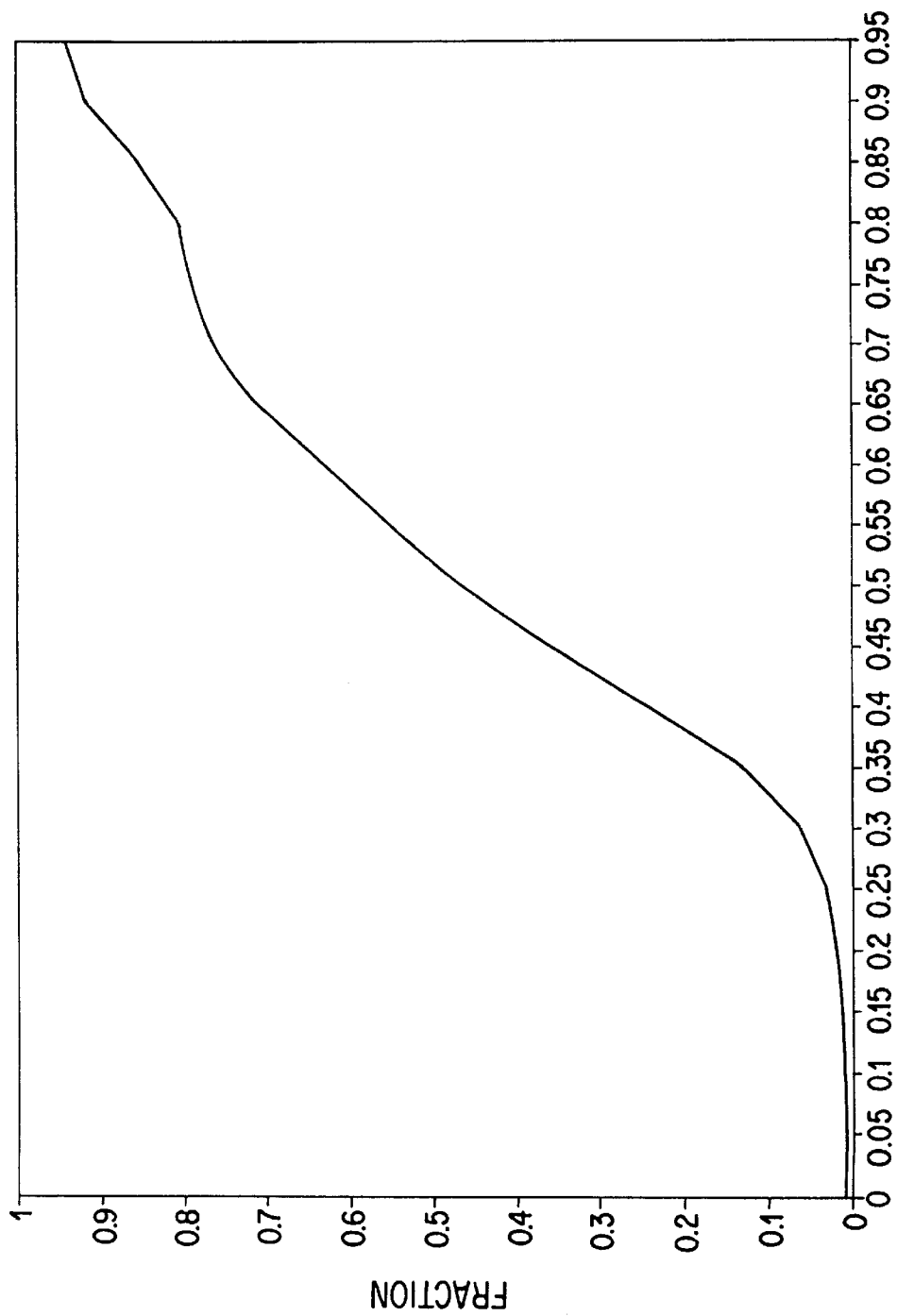

To convert this data to sigmoid plots, the data lists were examined for everything which as active, and a Tanimoto coefficient calculated (on the whole molecule) between every active molecule and everything else in the list. For plotting, the value of the number of molecules which were a given value (X) away from an active compound was determined. The proportion (frequency of such molecules) was plotted on the vertical axis and the Tanimoto coefficient on the horizontal axis. The bin widths for the X axis are 0.05 Tanimoto difference units wide, and the activity from Index Chemicus was simply "active" or "inactive". FIGS. 9A and 9B show the resulting plots for 16 of the 18 data sets broken down into sets of 8 (replication of these Figures in the priority applications did not pick up the ninth curve in each Figure, so that the ninth curve in each set has been ommitted from this application). Many of the curves have a sigmoid shape, but the inflection points clearly differ. Also, it is not clear what effect excluding the differences between active and inactive molecules has on the shape of the curves. To get an overall view, FIG. 9C shows the cumulative plot for both series of 9 activities. This plot generally indicates that, given an active molecule, the probability of an additional molecule, which falls within a Tanimoto similarity of 0.85 of the active, also being active is, itself, approximately 0.85. Stated slightly differently, when a Tanimoto similarity descriptor is summed over an arbitrary assortment of molecules and biological activities, it is clear that molecules having a Tanimoto similarity of approximately 0.85 are likely to share the same activity. Thus, the Tanimoto similarity displays a neighborhood behavior (neighborhood distance of approximately 0.15) when applied to a large enough number of arbitrary sets of compounds. As will be discussed later, one of the more powerful aspects of the Patterson plot validation method is that it can provide a relative ranking of metrics and distinguish on what type of data sets each may be more useful. In this regard, it will be seen that the whole molecule Tanimoto coefficient as a diversity descriptor has unanticipated and previously unknown drawbacks.

However, one of the principle features of the present invention, neither taught by the Abbott researchers nor recognized by anyone in the prior art, is that the Tanimoto descriptor can be used in a unique manner in the construction of a combinatorial screening library. In fact, as will be seen, it has been discovered that this descriptor can be used to provide an important end-point determination for the construction and merging of such libraries and, in addition, is a useful descriptor for constructing and searching the virtual library.

C. Comparison of Sigmoid and Patterson Plots

It is important to understand the difference in the types of information about descriptors and the neighborhood property which is yielded by the Abbott sigmoid plot and the generalized validation method and Patterson plot of the present invention.

To make a sigmoid plot, the molecules must be first be divided into two categories, active molecules and inactive molecules, based on a cut off value chosen for the biological activity. One molecule of a pair must be active (as defined by the cut off value) before the pair is included in the sigmoid plot. Pairs in which neither molecule has any activity, as well as those pairs in which neither molecule has an activity greater than the cut off value, do not contribute information to the sigmoid plot. Thus, the sigmoid plot does not use all of the information about the chemical data set under study. In fact, it uses a limited subset of data derivable from the more general Patterson plot described above. As a consequence very large sets of data (or sets for which both the activity and inactivity in an assay are experimentally known) are needed to get statistically significant results from the sigmoid plots.

By comparison, the Patterson plot clearly displays a great deal more information inherent in the data set which is relevant to evaluating the metric. Most importantly, the validity and usefulness of the metric can be quickly established by examining the Patterson plots resulting from application of the metric to random data sets. As will be shown in the next section, a metric may reflect a neighborhood property (such as in a sigmoid plot), but at the same time may not be a particularly valid/useful metric or may have limited utility. In Patterson plot analysis, all pairs of molecules and their associated activities or inactivities contribute to the validity analysis and to the determinations of the neighborhood radius. Thus, in a Patterson plot, it is easy to see what percentage of the total data set is included when the neighborhood definition is changed by choosing a different biological difference range. This has important consequences for choosing the correct neighborhood radius for clustering.

Figure 10A:
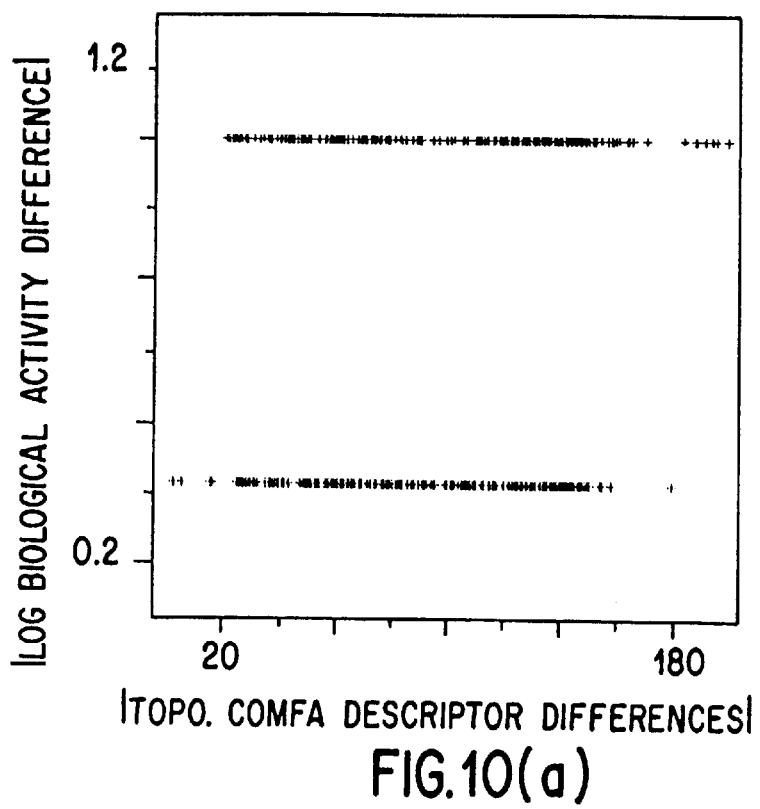
FIGS. 10a and 10b show a Patterson plot of the Cristalli data set using only those values which would have been used for a Tanimoto sigmoid plot of the same data set alongside a Patterson plot of the complete data set.
Figure 10B:
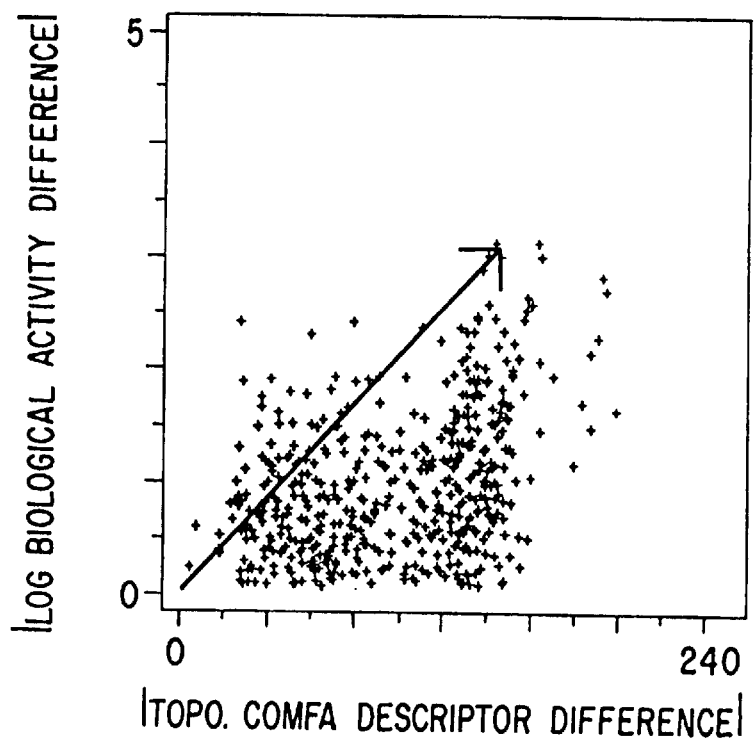

To better see the relationship between the information available from each type of plot, FIG. 10A shows a Patterson plot for the Cristalli data set reconstructed under the Abbott sigmoid plot simplification that the 32 molecules were either "active" (activity=1) or "inactive" (activity =0). The cut off value for biological activity was chosen to be 60 $\mu$M. Thus, "active" molecules were those with an A1 agonist potency of 60 $\mu$M or less, and "inactive" molecules were those with a potency greater than 60 $\mu$M. With this Abbott simplification, only two differences in bioactivities can occur for a pair of molecules: both active or inactive, difference=0; or one active and the other inactive, difference=1. The result of constructing a Patterson plot for this impoverished data set thus must appear as two parallel lines, as shown in FIG. 10A alongside the Patterson plot for the full Cristalli data set in FIG. 10B. Although a triangle and trapezoid should still be anticipated within such a reduced plot, the active/inactive classification so limits the observable biological differences that no pattern whatsoever is apparent. The very limited nature of the information retained is clearly seen. In particular, by only looking at molecular pairs in which one molecule is active above a predetermined cut off value, the sigmoid plot totally fails to take into account all the information about the behavior of the metric with respect to non-active pairs (in which one or both molecules have activities less than the cut off value) contained in the distribution of points in the Patterson plot. As a major consequence, the Patterson plot is: 1) able to derive information from much less data; and 2) much more sensitive to all the nuances contained in the data.

6. Comparison of Tanimoto and Topomeric CoMFA Metrics

Having recognized that both the topomeric CoMFA and Tanimoto coefficient metrics display the neighborhood property, a comparison (between Table 1 and columns 3 and 4 of Table 3) of the application of the two metrics to identical data sets yields interesting insights into their respective sensitivities. The prior art practice of using the value of (1−Tanimoto coefficient) as a distance was followed when performing the analysis. For columns 3 and 4 of Table 3, Patterson plots were constructed using the Tanimoto distances of the whole molecules represented in the 20 data sets which had been used for the topomeric CoMFA analysis. Patterson plots were also constructed using the Tanimoto distances of just the side chains (as was done with the topomeric CoMFA metric) of the molecules for the same 20 data sets. In Table 3 are shown the Tanimoto fingerprint density ratios for the whole molecule and side chain Tanimoto metrics and the corresponding $X^2$ values for the 20 data sets.

TABLE 3

Patterson Plot Ratios and Associated $X^2$

| Col. 1 Side Chain | Col. 2 Side Chain | Col. 3 Whole Molecule | Col. 4 Whole Molecule |
| --- | --- | --- | --- |

| No. | Reference | Tanimoto Fingerprint Ratio | Tanimoto Fingerprint $X^2$ | Tanimoto Finger print Ratio | Tanimoto Finger print $X^2$ |
| --- | --- | --- | --- | --- | --- |
| 1 | Uehling | 1.89 | 14.22 | 1.55 | 6.22 |
| 2 | Strupczewski | 1.70 | 143.48 | 1.41 | 59.61 |
| 3 | Siddiqi | 1.04 | 0.08 | 1.04 | 0.07 |
| 4 | Garratt-1 | 1.60 | 8.10 | 1.07 | 0.19 |
| 5 | Garratt-2 | 1.89 | 36.05 | 1.08 | 0.50 |
| 6 | Heyl | 1.71 | 13.83 | 1.01 | 0.00 |
| 7 | Cristalli | 1.75 | 144.54 | 1.31 | 30.27 |
| 8 | Stevenson | 0.94 | 0.05 | 1.07 | 0.04 |
| 9 | Doherty | 1.73 | 4.03 | 1.05 | 0.04 |
| 10 | Penning | 1.97 | 37.03 | 1.53 | 12.73 |
| 11 | Lewis | 1.64 | 4.80 | 1.01 | 0.00 |
| 12 | Krystek | 1.01 | 0.04 | 1.23 | 16.31 |
| 13 | Yokoyama-1 | 1.48 | 9.94 | 1.01 | 0.00 |
| 14 | Yokoyama-2 | 1.37 | 18.94 | 1.70 | 16.03 |
| 15 | Svensson | 1.64 | 16.61 | 1.02 | 0.02 |
| 16 | Tsutsumi | 1.74 | 21.56 | 1.58 | 14.35 |
| 17 | Chang | 1.34 | 145.00 | 1.13 | 8.36 |
| 18 | Rosowsky | 1.04 | 0.06 | 1.01 | 0.00 |
| 19 | Thompson | 1.72 | 7.83 | 1.17 | 0.68 |
| 20 | Depreux | 1.60 | 64.22 | 1.18 | 6.73 |
|  | MEAN | 1.54 | 34.62 | 1.21 | 8.61 |
|  | STANDARD DEVIATION | 0.32 | 49.85 | 0.23 | 14.57 |

Surprisingly the whole molecule Tanimoto appears to be a good descriptor for only 50% of the data sets (10/20 data sets with a ratio greater than 1.1). At first glance this is surprising in light of the original Abbott data, but, on second consideration, it is consistent with the observed significant individual variability of the plots obtained from the Index Chemicus analysis in FIGS. 9A and 9B. The Patterson plots confirm that the Tanimoto coefficient does display a neighborhood property for some data sets, but clearly it is less valid/useful for other sets. And it is not as consistent as the topomeric CoMFA or the side chain Tanimoto descriptor which were valid 85% (17/20) and 80% (16/20) of the time respectively. Upon inspection of the whole molecule Tanimoto data, it can be seen that the 10 data sets which do not have ratios greater than 1.1 all have a small Tanimoto range and/or contain relatively few compounds. The $X^2$ values for these data sets also confirm the lack of statistical significance. Essentially, the whole molecule Tanimoto is a less discriminating diversity measurement than the others and would appear to need, at the very least, more data and/or a greater range of values. The method of this invention clearly provides much more information and insight into the validation of the Tanimoto metric than did the Abbott style sigmoid plot.

For the majority of sets, 80% (16/20), the side chain Tanimoto metric also appears to be valid/useful. This is an extraordinarily surprising result since this metric has always been thought of in the prior art as useful only as a measure of whole molecule similarity. Overall, it compares favorably with topomeric CoMFA. A very interesting aspect, however, is that the sets for which validity is not apparent are not identical for the topomeric CoMFA and side chain Tanimoto metrics. The side chain Tanimoto metric does not appear valid with respect to sets 3, 8, 12, and 18. Clearly set 8 had too little data for either the topomeric CoMFA or the side chain Tanimoto descriptors. The most interesting comparison involves sets 3, 12, and 18 which validated the topomeric CoMFA metric but for which the side chain Tanimoto metric appears invalid. Upon inspection, these sets all con tained substituents in which only the position of a particular side chain varied. Since the topomeric CoMFA metric is sensitive to the relative spatial orientations of the side chains, while the Tanimoto metric is only sensitive to the presence or absence of the side chains, the sterically driven topomeric CoMFA metric was sensitive to the differences in these sets while the Tanimoto was insensitive. In certain circumstances the Tanimoto may be a useful descriptor of molecular diversity for use on the reactants in a combinatorial synthesis; a result totally at odds with the wisdom of the prior art. Clearly, however, the differences in sensitivities between the metrics should be considered when applying them.

Further, considering the five metrics already discussed above (topomeric CoMFA, whole molecule Tanimoto, side chain Tanimoto, random numbers, and force field energy) it is clear that the validation method of this invention can be used to rank the relative quality (validity/usefulness) of the metrics. In addition, when enough metrics have been examined by the method of this invention, it will be possible to choose metrics appropriate to the type of molecular structural differences which it is desired to analyze. Correspondingly, when a metric, which has been validated over a very wide range of data sets and biological activities, yields surprising results (appears invalid) when applied to a new data set, one potential interpretation may be that the data are in error. This highlights another feature of the invention, the ability to reliably suggest that some experimental observations are generating unusual data. Instead of using a data set to validate a metric, the previously validated metric is used to examine the reliability of the data set. By constructing Patterson plots and checking the associated $X^2$ value for significance, experimental scientists have another tool with which they may independently assess their data, especially in situations where new biological activities are being investigated.

7. Additional Validation Results

Considering that the validation method of this invention has shown that both the topomeric CoMFA metric and the Tanimoto metric define metric spaces where biological properties cluster (that is; the metrics are sensitive to biologically relevant molecular structural differences), a descriptor combining the two metrics was constructed. A combined descriptor has been identified which is the best diversity descriptor discovered to date. This descriptor has been validated and has been found to be far superior to any previously considered metric in its ability to identify a neighborhood of similarity for design purposes. This descriptor, a weighted combination of the topomeric CoMFA descriptor and the Tanimoto descriptor, defines a distance measure as:

$$\sqrt{(1-\text{Tanimoto})^2+(0.003\times\text{topomericCoMFA})^2}$$

This descriptor has a ratio greater than 1.1 in all 20 out of the 20 test data sets, and, in fact, averages a ratio of 1.55. In all 20 data sets for a neighborhood distance of 0.240 (corresponding to a biological activity difference of 2 log units) not one single point was found above the line in the Patterson plot. Although this may appear as a "perfect" metric, it is doubted that this level will be maintained as more and more data sets are added to the validation group. However, it is believed that it will continue to be the strongest of the presently known descriptors. At the present time, the results of performing validation studies on the combined descriptor and other possible metrics using the Patterson plot method of this invention and the 20 described data sets result in the following data:

TABLE 4

Patterson Plot Ratios

| No. | Reference | HB | LOGP | MR | AP | CONN | AUTO | COMBO |
|---|---|---|---|---|---|---|---|---|
| 1 | Uehling | 1.83 | 1.09 | 1.07 | 1.55 | 1.19 | 1.66 | 1.87 |
| 2 | Strupczewski | 1.48 | 1.00 | 0.99 | 1.40 | 1.05 | 1.20 | 1.47 |
| 3 | Siddiqi | 1.47 | 0.97 | 0.92 | 1.00 | 1.07 | 1.00 | 1.48 |
| 4 | Garratt-1 | a | 1.01 | 1.01 | 0.90 | 1.11 | 1.14 | 1.68 |
| 5 | Garratt-2 | a | 1.01 | 1.00 | 0.97 | 1.09 | 1.09 | 1.50 |
| 6 | Heyl | 1.24 | 0.98 | 0.95 | 1.11 | b | 1.01 | 1.34 |
| 7 | Cristalli | 1.22 | 1.06 | 0.99 | 1.27 | 0.98 | 1.17 | 1.44 |
| 8 | Stevenson | a | 1.03 | 1.03 | 1.02 | 1.02 | 1.02 | 1.60 |
| 9 | Doherty | 1.07 | 1.00 | 1.01 | 1.18 | 1.02 | 1.28 | 1.78 |
| 10 | Penning | 1.72 | 1.00 | 0.97 | 1.05 | 1.00 | 1.36 | 1.67 |
| 11 | Lewis | *0.57 | 1.00 | 1.02 | 0.97 | 1.15 | 1.14 | 1.62 |
| 12 | Krystek | 1.69 | 0.85 | 0.85 | 1.43 | 1.01 | 1.00 | 1.75 |
| 13 | Yokoyama-1 | *0.71 | d | 1.01 | 1.25 | 1.01 | 0.99 | 1.52 |
| 14 | Yokoyama-2 | 1.00 | 1.00 | 0.99 | 1.25 | 1.05 | 0.99 | 1.57 |
| 15 | Svensson | *0.31 | 1.01 | 0.99 | 1.31 | 1.08 | 1.00 | 1.39 |
| 16 | Tsutsumi | 1.67 | 1.04 | 0.95 | 1.18 | 1.00 | 0.95 | 1.52 |
| 17 | Chang | 1.35 | 1.00 | 1.00 | 1.00 | c | 1.20 | 1.36 |
| 18 | Rosowsky | 1.44 | 1.03 | 0.96 | 1.23 | 1.08 | 1.21 | 1.66 |
| 19 | Thompson | a | 1.12 | 0.99 | 0.87 | 1.02 | 1.01 | 1.47 |
| 20 | Depreux | *0.44 | 1.02 | 0.99 | 0.99 | 1.01 | 0.98 | 1.26 |
| | MEAN | *1.43 | 1.01 | 0.98 | 1.15 | 1.05 | 1.12 | 1.55 |
| | STANDARD DEVIATION | *0.27 | 0.05 | 0.05 | 0.19 | 0.06 | 0.17 | 0.16 |

HB = Topomeric Hydrogen Bonding
LOGP = Calculated Log P
MR = Molar Refractivity
COMBO = Combined Topomeric CoMFA & Tanimoto
AP = Atom Pairs[14]
AUTO = Autocorrelation[15]
CONN = Connectivity Indices[16]
*Asterisked values are excluded in computing the mean. These values are all artifacts, the result of there being no more than two distinguishable values of the molecular descriptor within the particular series, hence only two possible values of the x variable in a Patterson plot.
[a]No Hydrogen bonding groups exist to define the metric under HB
[b]Too many groups for s/w to handle under CONN
[c]One hexavalent atom confuses the computation under CONN
[d]A LOGP could not be calculated for the molecules in this data set Combining the data from Table 4 with the data from Tables 1 and 3 permits the relative ranking of some known metrics:

| VALIDITY/USEFULNESS RANK: | No. Of Ratios > 1.1 |
|---|---|
| USEFUL | |
| Combined Topomeric Steric CoMFA and Tanimoto | 20/20 |
| Topomeric Steric CoMFA | 17/20 |
| Tanimoto 2D Fingerprints (Side Chain) | 16/20 |
| Topomeric HBond Spatial Fingerprints | 10/12 |
| LESS USEFUL: | |
| Tanimoto 2D Fingerprints (Whole Molecule) | 10/20 |
| Atom Pairs (R. Sheridan) | 11/20 |
| Autocorrelation | 9/20 |
| NOT USEFUL - INVALID: | |
| Connectivity Indices (Health Design Implementation, first 10) | 3/18 |
| Partition Coefficient (CLOGP) | 1/19 |
| Molar Refractivity (CMR) | 0/20 |
| Force Field Strain Energy | 0/18 |
| Random Numbers | 0/20 |

Note: A denominator of less than 20 indicates that the metric could not be calculated for all 20 data sets.

8. Combinatorial Library Design Utilizing Validated Metrics

The starting point for the design of any combinatorial screening library is the choice of synthetic reaction scheme involving the selection of the core molecule and the possible reactants which could be used with any specific chemistry. As mentioned earlier, well known and understood organic reactions are generally utilized. Initially, information about the chemical structure of all the reactants (and cores, when appropriate) and the synthetic chemistry involved (what products can be built) is input as a database in the computer in a form recognizable by the computational software. Using the insights gained from the discovery of the validation method of this invention, it is now possible to design general purpose combinatorial screening libraries of optimal diversity.

Conceptually, the design process may be thought of as a filtering process in which the molecules available in a combinatorially accessible chemical universe are run through consecutive filters which remove different subsets of the universe according to specified criteria. The goal is to filter out (reduce the numbers of) as many compounds as possible while still retaining those compounds which are necessary to completely sample the molecular diversity of the combinatorially accessible universe. The basic design method of this invention along with several ancillary considerations is shown schematically in FIG. 11 using the filter analogy. For this example only two sets of reactants are considered with one reactant of each set being contributed to each final product molecule. The reactants are shown forming the top row and first column of a combinatorial matrix A. Only a portion of the possible combinatorial matrix is shown, the remainder being indicated by the sections connected to the matrix by dots. One set of reactants is represented by circles 1, and the other set by squares 2. Each empty matrix location represents one possible combinatorial product which can be formed from the two sets of reactants. (The matrix of possible products would be a rectangular prism for three sets of reactants, and a multidimensional prism for higher orders of reactant sets.) As the design process is implemented, the number of products to be included in the screening library design is reduced by each filter 4. Beside each filter step is indicated the corresponding text section describing that filter. Also set out opposite each filtering step is an indication of the software and its source required to implement that step.

A. Removal of Reactants for Non-Diversity Reasons

In designing screening libraries derived from combinatorially accessible chemical universes, practical and end use considerations as well as diversity concerns can be used to reduce the number of reactants which will be used to combinatorially specify the product molecules. These practical and end-use criteria can be divided into those of general applicability and those of more specific applicability for a particular type of screening library (such as for drug discovery). The following discussion is not meant to be limiting, but rather is intended to suggest the types of selections which may be made.

i. General Removal Criteria

As a first consideration, reactants with unusual elements (such as the metals) are normally excluded when considering the synthesis of organic molecules. In addition, tautomerization of structures can cause problems when searching a universe of reactants data base either by missing structures that are actually present or by finding a specific functional group which is really not there. The most common example of this is the keto-enol tautomerism. Thus, possible tautomeric reactants must be examined and improper forms eliminated from consideration. Generally, reactants may be provided in solvent, as salts with counterions, or in hydrated forms. Before their structures can be analyzed for diversity purposes, the salt counter-ions, solvent, and/or other species (such as water) should be removed from the molecular structure to be used.

Figure 11A:
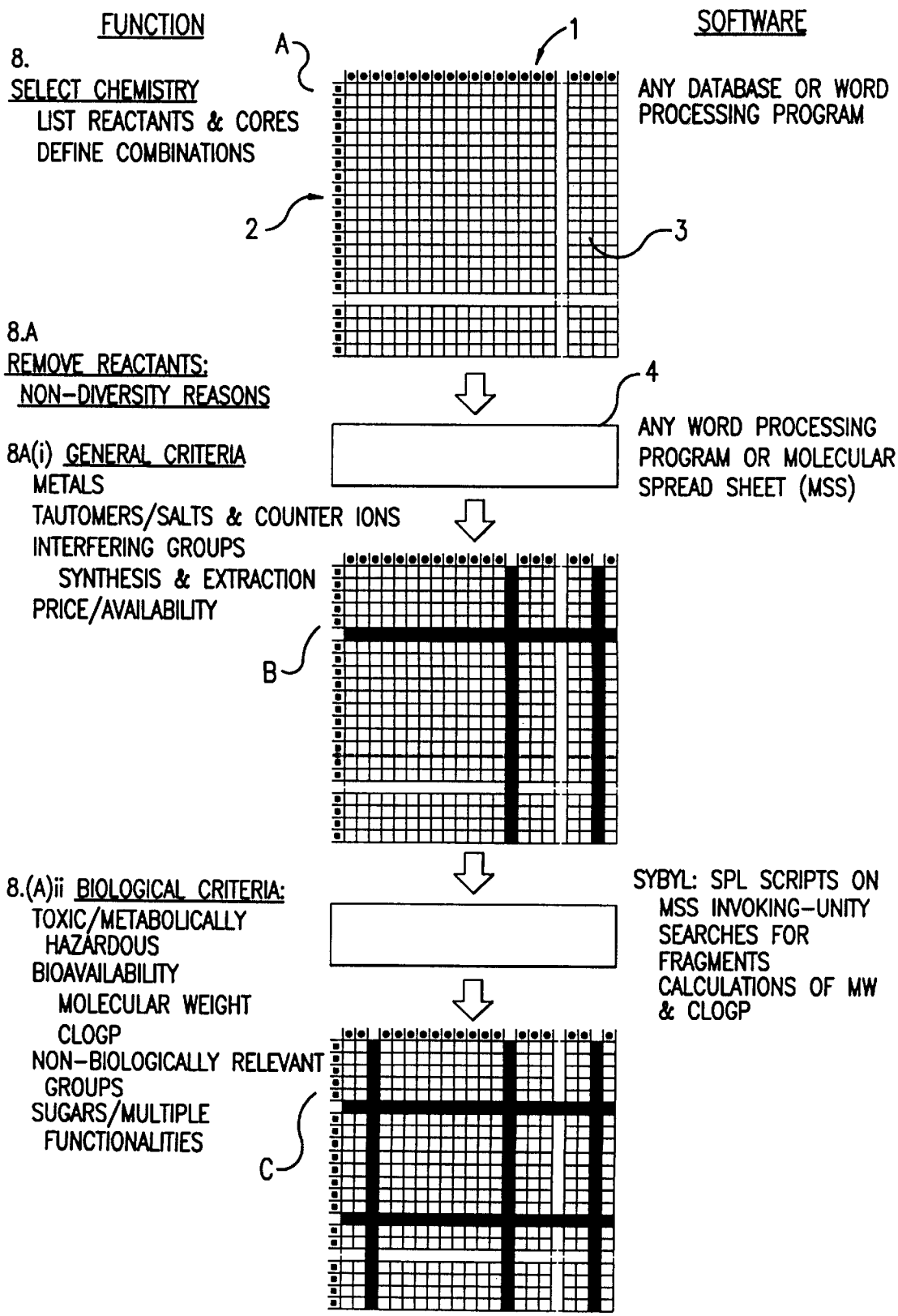
Figure 11C:
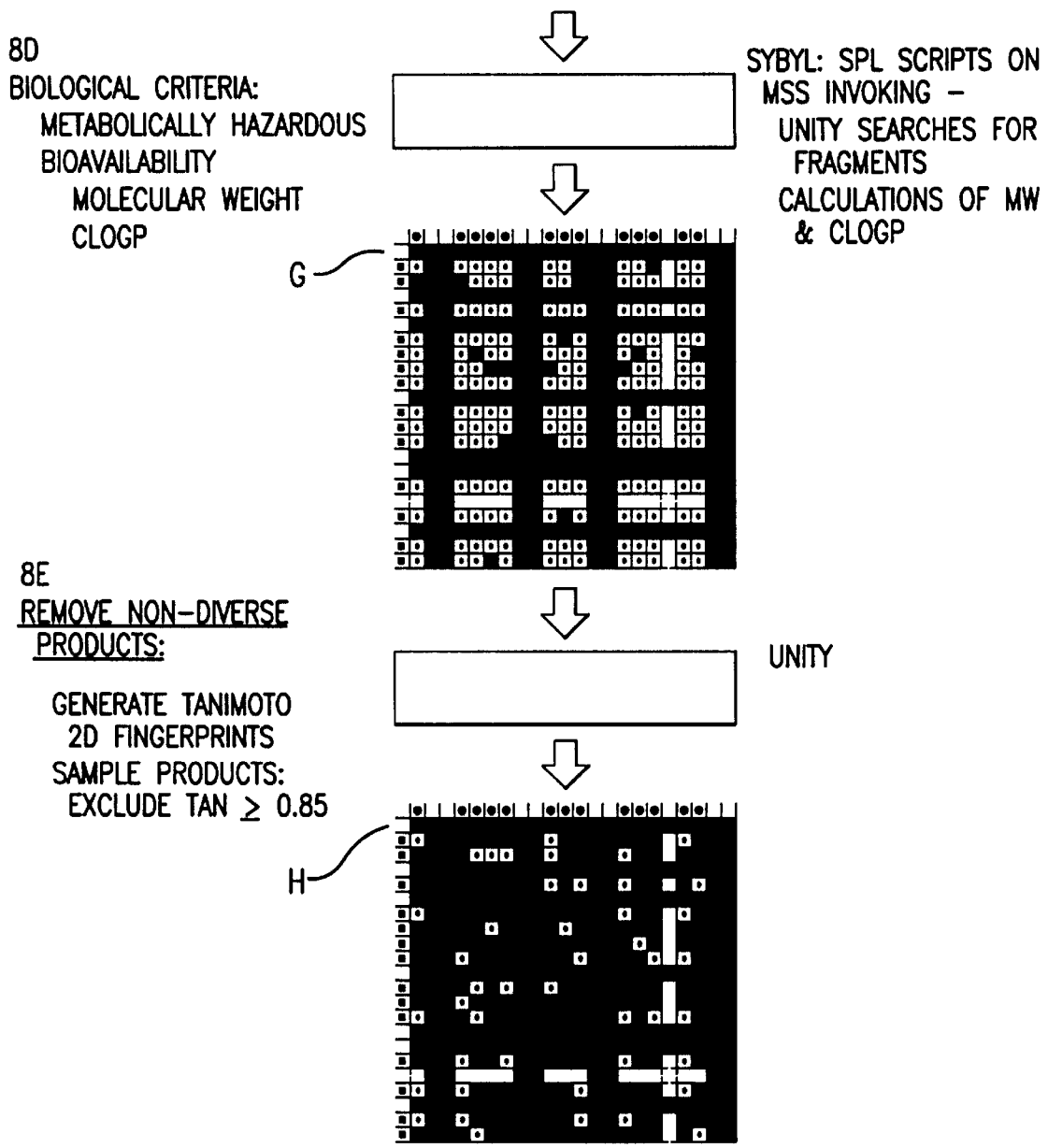

Additionally, reactants may contain chemical groups which would interfere with or prevent the synthetic reaction in which it is desired to use them. Clearly, either different reaction conditions must be used or these reactants removed from consideration. Sometimes, while the synthesis may be possible, extraction of the products resulting from some reactants may be difficult using the proposed synthetic conditions. Again, if possible, another synthetic scheme must be used or the reactants removed from consideration. Price and availability are not insignificant considerations in the real world. Some reactants may need to be specially synthesized for the combinatorial synthesis or are otherwise very expensive. In the prior art, expensive reactants would typically be eliminated before proceeding further with the library design unless they were felt to be particularly advantageous. One of the advantages of the method of this invention is that the decision whether to include expensive reactants may be postponed until the molecular structures have been analyzed by a validated descriptor. With confidence that the validated descriptor permits clustering of molecules representing similar diversity, often another, less expensive, reactant can be selected to represent the diversity cluster which also includes the expensive molecule. The specifics of any particular contemplated combinatorial synthesis may suggest additional appropriate filtering criteria at this level. In FIG. 11 the effect on the number of possible products of removing only a few reactants is easily seen in matrix B. For each reactant removed, whole rows and columns of possible products are excluded.

ii. Biologically Based Criteria

A library designed for screening potential pharmacological agents imposes it own limitations on the type and size of molecules. For instance, for drug discovery, toxic or metabolically hazardous reactants or those containing heavy metals (organometallics) would usually be excluded at this stage. In addition, the likely bioavailability of any synthetic compound would be a reasonable selection criteria. Thus, the size of the reactants needs to be considered since it is well known that molecules above a given range of molecular weights generally are not easily absorbed. Accordingly, the molecular weight for each reactant is calculated. Since the final molecular weight for a bioavailable drug typically ranges from 100 to 750 and since, by definition, at least two reactants are used in a combinatorial synthesis, reactants having a size over some set value are excluded. Typically, those above 600 are excluded at this stage at the present time. A lower value could be used, but it is felt that there is no reason to restrict the diversity unduly at this stage in the design process. Once again, of course, this value can be adjusted depending on the chemistry involved.

Another aspect of bioavailability is the diffusion rate of a compound across membranes such as the intestinal wall. Reactants not likely to cross membranes (as determined by a calculated LogP or other measure) would usually be eliminated. At the present time, although the CLOGP for reactants makes only a partial contribution to the product CLOGP, it is believed that if any reactant has a CLOGP greater than 10, it will not make a usable product. Accordingly, the CLOGP is calculated for each reactant and only those with CLOGP$\leq$10 are kept. Again, in any particular case, a different value of CLOGP could be utilized. For those reactants for which it is difficult or impossible to calculate a LOGP, it is assumed the CLOGP would be less than 10 so that the reactants are kept in the library design at this point. As will be discussed later, a CLOGP will also be calculated on the products.

Other reactants are considered undesirable due to the presence of structural groups not considered "bio-relevant". Bio-relevance is judged by comparison with known drugs and by the experience of medicinal chemists involved in the design of the library. It is hoped that a future formal analysis of drug databases will yield further information about which groups should be excluded. Exclusion on this basis should be minimized since one of the goals of the combinatorial library design process is to find biologically active molecules through the exploration of combinatorial chemistry space which might not otherwise be found. Other removal criteria may be based on whether possible reactants involved sugars or had multiple functionalities. At the present time, the compounds shown in Table 5 are believed to be undesirable and are generally excluded at the initial stage of library design.

TABLE 5

Biologically Non-Relevant Groups

| GROUP DEFINITION | SYBYL Line Notation (SLN) | Reason(s) For Exclusion |
|---|---|---|
| BOC | C(OC(=O)N)(CH3)(CH3)CH3 | Stability |
| FMOC | C[1]H:C[2]:C(:CH:CH:CH @ 1)CH(CH2OC(=O)N)\ C[22]:C @ 2:CH:CH:CCH:CH: @ 22 | Stability |
| Hydrolyzable acyclic groups | Lvg-[!r]C(-Any)-[!r]Lvg{Lvg:O\|N\|Br\|Cl\|I} | Stability |
| Silicon, Aluminum, Calcium | Si, Al, Ca | Unfashionable |
| Polyhydroxyls/sugars | HOCC(OH)COH | Extraction Difficulties |
| Allyl halides | HaloC(Any)C = :Any{Halo:Br\|Cl\|I} | Stability, alkylating agent |
| Benzyl halides | HaloC(Any)C = :Any{Halo:Br\|Cl\|I} | Stability, alkylaling agent |
| Phenacyl halides | HaloC(Any)C = :Any{Halo:Br\|Cl\|I} | Stability, alkylating agent |
| Alpha-halo carbonyls | HaloC(Any)C = :Any{Halo:Br\|Cl\|I} | Stability, alkylating agent |
| Acyl halides | Csp(=O)Hal{Csp:C\|S\|P} | Stability, alkylating agent |
| Phosphyl halides | Csp(=O)Hal{Csp:C\|S\|P} | Stability, alkylating agent |
| Thio halides | Csp(=O)Hal{Csp:C\|S\|P} | Stability, alkylating agent |
| Carbamates | NoroC(=O)Hal{Noro:N\|O\|S} | Stability, alkylating agent |
| Chloroformates | NoroC(=O)Hal{Noro:N\|O\|S} | Stability, alkylating agent |
| Isocyanates | N = C = Het | Stability, alkylating agent |
| Thioisocyanates | N = C = Het | Stability, alkylating agent |
| Diimides | N = C = Het | Stability, alkylating agent |
| Sulfonating agents | Het(=O)(=O))Lvg{Lvg:OHev\|Hal} | Stability, alkylaling agent |
| Phosphorylating agents | Het(=O)(=O))Lvg{Lvg:OHev\|Hal} | Stability, alkylating agent |
| Epoxides, etc. | C[1]HetC @ 1 | Stability, alkylating agent |
| Diazos | Any~N[F]~N[F] | Stability, toxicity |
| Azides | Any~N[F]~N[F]~Oorn[F]{Oorn:O\|N} | Stability, toxicity |
| Nitroso | Any~N[F]~N[F]~Oorn[F]{Oorn:O\|N} | Toxicity |
| Mustards | HaloC(Any)C(Any)Lvg{Lvg:Het\|Halo}{Halo:Br\|Cl\|I} | Stability, alkylating agent |
| 2-halo ethers | HaloC(Any)C(Any)Lvg{Lvg:Het\|Halo}{Halo:Br\|Cl\|I} | Stability, alkylating agent |
| Quaternary Nitrogens | Hev~Norp(~Hev)(~Hev)~Hev{Norp:P\|N} | Extraction difficulties |
| Quaternary Phosphorus | Hev~Norp(~Hev)(~Hev)~Hev{Norp:P\|N} | Extraction difficulties |
| Acid anhydrides | Het = Any-[!r]O-[!r]Any = Het | Stability, alkylating agent |
| Aldehyde | CCH = O | Stability, alkylating agent |
| Polyfluorinates | FC(F)C(F)F | Unfashionable |
| Michael acceptor | O = C(Nothet)-C = Any(H)Nothet{Nothet:C\|H} | Toxicity |
| Trialkylphosphines | P(C)(C)C | Stability |
| Other Triaryls | Any:Any-[!r]Any(-[!r]Any:Any)\ (-[!r]Any:Any)Lvg{Lvg:Het\|Hal} | Stability |
| Alpha-dicarbonyls | Oorn = [!r]Any(AnyHev)-C = [!r]Oorn{Oorn:O\|N} | Stability |

The choice of whether to eliminate some reactants based on such general and specific considerations will vary with the given situation. Except in the case of toxic materials, it is recognized that any other limiting selection decreases the diversity of the combinatorial library and potentially eliminates active molecules. As always, when eliminating reactants at the very beginning of library design, the problem boils down to a question of probabilities: what is the likelihood of missing a significant lead molecule? In the real world, what is desired at the very least is a high probability that it is unlikely that such a molecule will be missed if the selection criteria under consideration are implemented. The application of many of these selection criteria (price, availability, toxicity, bioavailability, diffusion, and non-biologically relevant structural groups) can occur before, during, or after the screening library has been selected based on other criteria. Clearly, however, the earlier these selection criteria are applied, the greater will be the reduction in the number of combinatorial possibilities which will need to be evaluated later in the design process. As will be discussed below, not only are these criteria applied at the reactant level, but some of them will also be applied again at the product level. Reduction of the number of reactants (for the reasons set forth above) in the early stages of the library design process is indicated in FIG. 11 at matrix C.

B. Removal of Non-Diverse Reactants

As noted earlier, an ideal combinatorial screening library will: 1) have molecules representing the entire range of diversity present in the chemical universe accessible with a given set of combinatorial materials; and 2) will not have two examples of the same diversity when one will suffice. The goal is to obtain as complete a sampling of the diversity of chemical space as is possible with the fewest number of molecules, and, coincidentally, at lowest cost. In selecting a subset of a possible combinatorial universe to include in a screening library, there are two opportunities based on diversity considerations to reduce the number of included molecules. The first opportunity occurs when selecting reactants for the combinatorial synthesis. The fewer the number of reactants, the much fewer the number of combinatorial possibilities. The second opportunity occurs after all the combinatorial possibilities from the chosen reactants (and core) have been selected. The method of the present invention utilizes both opportunities by using validated metrics appropriate to each situation.

Any metric which has been shown by the Patterson plot validation methodology to be valid/useful when applied to reactants may be used at this stage of the library design process. However, there are a number of reasons to use a metric which reflects the steric diversity of the combinatorially accessible chemical universe. The principle reason is that the accumulated observation of biological systems is that ligand-substrate binding is primarily governed by three dimensional considerations. Before a reactive side group can get to the active site, before appropriate electrostatic interactions can occur, before appropriate hydrogen bonds can be formed, and before hydrophobic effects can come into play, the ligand molecule must basically "fit" into the three dimensional site of the substrate. Thus a principal consideration in designing screening libraries should be to sample as much of the three dimensional (steric) diversity of the combinatorial universe as is possible. The initial method of the present invention does this by utilizing the validated topomeric CoMFA metric to analyze the steric properties of the proposed reactants.

A second reason for applying a steric metric to the reactants is that all of the three dimensional variability of the products resulting from a combinatorial synthesis resides in the substituents added by the reactants since the core three dimensional structure is common to all molecules in any particular combinatorial synthesis. In a sense it would be redundant to measure the contribution to each product molecule of a core which is common to all the products. A third reason for applying a three dimensional metric to the reactants is that a sterically sensitive metric distinguishes differences among molecules that are not revealed using other presently known metrics. For instance, the topomeric CoMFA metric is more sensitive to the volume and shape of the space occupied by a molecule than is, for instance, either the side chain or whole molecule Tanimoto descriptor. FIG. 12 provides an illustrative example of this feature drawn from the thiol study which confirms what was seen in the Patterson plots of the topomeric CoMFA and Tanimoto whole molecule descriptor. FIG. 12 shows three clusters labeled 24, 25, and 29 for which the Tanimoto whole molecule fingerprint metric does not indicate any substantial difference in molecular structure among the molecules, labeled (a) through (f), making up each of the clusters. The large panel A in the upper right of FIG. 12 shows orthogonal 3D views of the volume differences within clusters 24, 25, and 29 comparing each of the molecules that are not in the majority steric field cluster. For example, the Cluster 24 figure B at the top shows four contours (yellow, green [hidden], red, and blue) indicating the differences in volumes occupied by compounds 24(*a*), 24(*b*), 24(*c*) and 24(*f*) compared to compounds 24(*d*) and 24(*e*) which are found in the same steric field cluster, number 10. The middle C and bottom D figures in the large panel A show similar distinguishable volume differences for Clusters 25 and 29. While the whole molecule Tanimoto metric does not distinguish much difference between the molecules within each of these clusters, it is readily apparent from FIG. 12, even to an untrained eye, that the molecules in the clusters represent very different types of structural diversity; that is, significantly different three dimensional volumes are occupied by the molecules within each whole molecule Tanimoto determined cluster. The topomeric CoMFA metric clearly shows steric differences that are not indicated by the 2D Tanimoto. As seen earlier, a side chain Tanimoto similarity descriptor also does not distinguish steric differences amongst some molecules. A metric responsive to steric differences is, therefore, clearly preferred as a diversity discriminator for reactants.

The initial method for selecting reactants based on diversity is shown schematically at the third filter in FIG. 11. A diversity selection based on three dimensional steric measures begins by: 1) generating 3D structures for the reactants; 2) aligning the 3D molecular structures according to the topomeric alignment rules; 3) generating CoMFA steric field values for the reactants including, if desired, hydrogen bonding fields, and applying a rotatable bond attenuation factor; and 4) calculating pairwise topomeric CoMFA differences for every pair of reactants. At this point the steric diversity of the reactant space has been mapped into the topomeric CoMFA metric space. From the validation of the topomeric CoMFA metric, it was found that the neighborhood radius for an apparent activity difference of 2 log units was defined by a distance of approximately 80–100 topomeric CoMFA units (kcal/mole). Therefore, at this point, the method of the invention clusters (using hierarchical clustering) the reactants in topomeric CoMFA space so that reactants having a pairwise difference of less than approximately 80–100 units are assigned to the same cluster. Put another way, clustering is continued until the inter-cluster separation is greater than approximately 80–100 units. (If desired, there is some leeway in choosing the exact neighborhood radius in and about the neighborhood range to use for any given biological system. An experienced practioner of the clustering art will easily be able to determine, by noting the natural breaks in the clustering, where about the 80–100 range best clustering is obtained.) This process will produce clusters having reactants whose product activities will only rarely differ by more than approximately 2 log units. If reactant clusters having products activities differing by a greater or lesser amount are desired, the neighborhood distance used may be increased or decreased accordingly. The effect on the neighborhood distance of choosing such other activity range can be seen by viewing the Patterson validating plots for the topomeric CoMFA descriptor.

The clustering process now identifies groups (clusters) of reactants having steric diversity from one another but also having the same steric properties within each cluster. Or put in terms familiar to medicinal chemists, the molecules of each cluster should be bioisosters. For purposes of designing a combinatorial screening library which has within it molecules representing the full range of steric diversity present in the universe of reactants, it is now only necessary to select one reactant from each cluster for inclusion in the library. A reasonable way to select the one reactant from each cluster would be to select the lowest priced or most readily available one. However, additional criteria may be considered. The diverse reactants remaining at matrix D need not be adjacent to each other on the combinatorial matrix and are only shown this way for graphic convenience. At this point the first stage of library design has been completed.

While the use of a topomeric CoMFA metric to measure the three dimensional structural diversity of the reactants has been discussed, it should be apparent that any metric: 1) reflective of the three dimensional properties of molecules; and 2) validated as taught above, could be applied to the reactants to be used in a combinatorial synthesis in the manner taught above. The teaching of this invention is not limited to the use of the topomeric CoMFA metric, but also includes the use on reactants of all validated three dimensional metrics. As seen earlier, at the present time initial studies of topomeric hydrogen bonding fields indicate that it should be a very useful metric. For those reactants expected to form large number of hydrogen bonds, this may be the metric of choice. The hydrogen bonding metric would be used as an adjunct to the topomeric CoMFA metric in those situations. There may be situations where a sterically sensitive metric is not needed, in which case it should be clear that any valid metric appropriate to reactants could be used.

C. Identification (Building) of Products

Once the set of diverse reactants has been identified by the above method, the structures of the product molecules can be combinatorially determined based on the synthetic reaction scheme and any desired cores. The reactants are used to build the structures of the combinatorial products using LEGION and are stored in molecular spread sheets. In matrix E the products which can still be built from the available reactants are shown as asterisks in each matrix location.

D. Removal of Products for Non-Diversity Reasons

After the possible product structures have been identified, another opportunity exists to reduce the number of products due to general non-diversity considerations. These considerations will generally be related to the particular chemistry involved and might relate to product instabilities, cyclic structures, etc. (Matrix F)

During the building of the combinatorial product molecules, the size of the product molecules increase and various combinations of core and substituents will affect the likely diffusion of the molecule (and may even form one of the biologically undesirable molecular groupings). Thus, in order to eliminate molecules which would not be used as drugs, the product molecules should be examined with many of the same selection criteria applied to reactants. In particular, molecular weights should be calculated and those compounds which have molecular weights over a predetermined value should be rejected. Typically, a value of 750 is used at this time as a representative weight above which bioavailability may become a problem. In addition, CLOGP should be calculated and any proposed molecule with a value under −2.5 or over 7.5 rejected. The number of structures eliminated at this point will depend in part both on the chemistry involved and the molecular weight range retained at the reactant stage. These additional product structures which are eliminated are reflected in matrix G.

E. Removal of Non-Diverse Products

As noted, a second opportunity based on diversity considerations to reduce the number of molecules to be included in the combinatorial screening library occurs after the products of a proposed combinatorial synthesis have been "built" by the software in the computer. Such an additional reduction is usually necessary since the number of combinatorial products at this stage may still be astronomically large. This is reflected in matrix G. In addition, it makes no sense to screen any more molecules than is absolutely necessary, and redundancy may occur in the products for several reasons. In a simple case, if two diverse reactants may react independently at each of two possible sites on a symmetric core molecule, two identical product molecules will be generated. In a more complex case, it is possible that one combination of core and reactants is similar (due to the similarities of structures contained in the core to the structure of the reactants) to another combination of core and reactants. That is, when the reactants are combined with the core molecule, it is possible that substructures within the core can combine with different substituents to form similar structures. Clearly, it would be redundant to screen both. How to select product molecules has been a vexing problem in the prior art, and this is one reason why the prior art has basically been concerned with clustering criteria. The general approach taken in the prior art to avoid oversampling combinatorial product molecules representing the same diversity has been to cluster the molecules and then maximize the distance between clusters with whatever metric was applied to the products.

Based upon an understanding developed from the theoretical considerations of validating a metric outlined above, the library design method of this invention again makes use of the neighborhood principle to solve this problem. However, it is important to understand that, unlike some methods of the prior art, the method of this invention specifically does not use a metric to cluster product molecules. Rather, the neighborhood definition may be used to decide which product molecules to retain in the final screening library and, correspondingly, when the appropriate number of product molecules have been selected for inclusion in the library. Essentially, starting with one product molecule, additional molecules are selected as far apart as possible (in the validated metric space) from any molecule already in the library until the next molecule to be selected would fall within the neighborhood distance of a molecule already included. Additional molecules are not included because to do so would include two or more molecules within the library representing the same structural diversity. Therefore, the neighborhood principle is used as a sampling rule to insure that molecules representative of the same diversity or otherwise too similar are not included in the library. The resulting combinatorial screening library is not redundant and has not oversampled the diversity space.

In the present invention, the Tanimoto 2D whole molecule similarity coefficient is used for the final product selection. As was seen above, this metric possesses the neighborhood property. Accordingly, from the combinatorial products either a first product is arbitrarily chosen for inclusion in the library or an initial seed of one or more products may be specified. (If an arbitrary product molecule is chosen, Tanimoto coefficients are calculated for all other molecules to the first molecule and a second molecule with the smallest Tanimoto coefficient [greatest distance—least similarity] from the first is chosen for inclusion.) For the efficient selection of additional molecules to be included, the distance (1−Tan. Coeff.) between each additional molecule and all molecules already included in the library is calculated. For each additional molecule, the distance to the closest molecule already in the library is identified. These closest distances for each additional molecule are compared, and the additional molecule whose closest distance is the greatest is selected next for inclusion; that is, the molecule which is farthest away from the closest molecule in the library is selected. A new set of distances is calculated and the process continued, selecting one molecule at a time, until no more molecules remain which are farther away than 0.15 ([1−0.85] the definition of a Tanimoto "distance" using the neighborhood value of 0.85). While this example is presented in terms of the Tanimoto similarity coefficient, any validated whole molecule metric and its neighborhood definition may be used with this sampling procedure.

As noted earlier, the value of 0.85 for the Tanimoto neighborhood definition originally appeared in the sigmoid plots. To confirm whether this is the correct neighborhood definition for the Tanimoto metric, the Patterson plots for the whole molecule Tanimoto in which the $X^2$ indicated significance were used to calculate the neighborhood value. The metric distances corresponding to 2-log and 3-log biological differences were determined by dividing the slope of the density determined line by the values 2 and 3 respectively. Over the data sets, the average metric distance for a 2 log biological difference was 0.14 and the average metric distance for a 3-log biological difference was 0.21. Since the Tanimoto distance of (1−Tan. Coeff.) is plotted in the Patterson plot, these values correspond to a 2-log similarity of 0.86 and a 3-log similarity of 0.79. This confirms the reasonableness of using 0.85 in the sampling process. Also, as discussed earlier, it is reasonable to have more confidence in the definition of the neighborhood derived from the Patterson plots which utilize all the molecular data. As noted with reference to selection of a neighborhood distance using the topomeric CoMFA metric on reactants, there may be a situation where a different biological activity may be appropriate and a correspondingly different neighborhood distance used for product selection.

Figure 13:
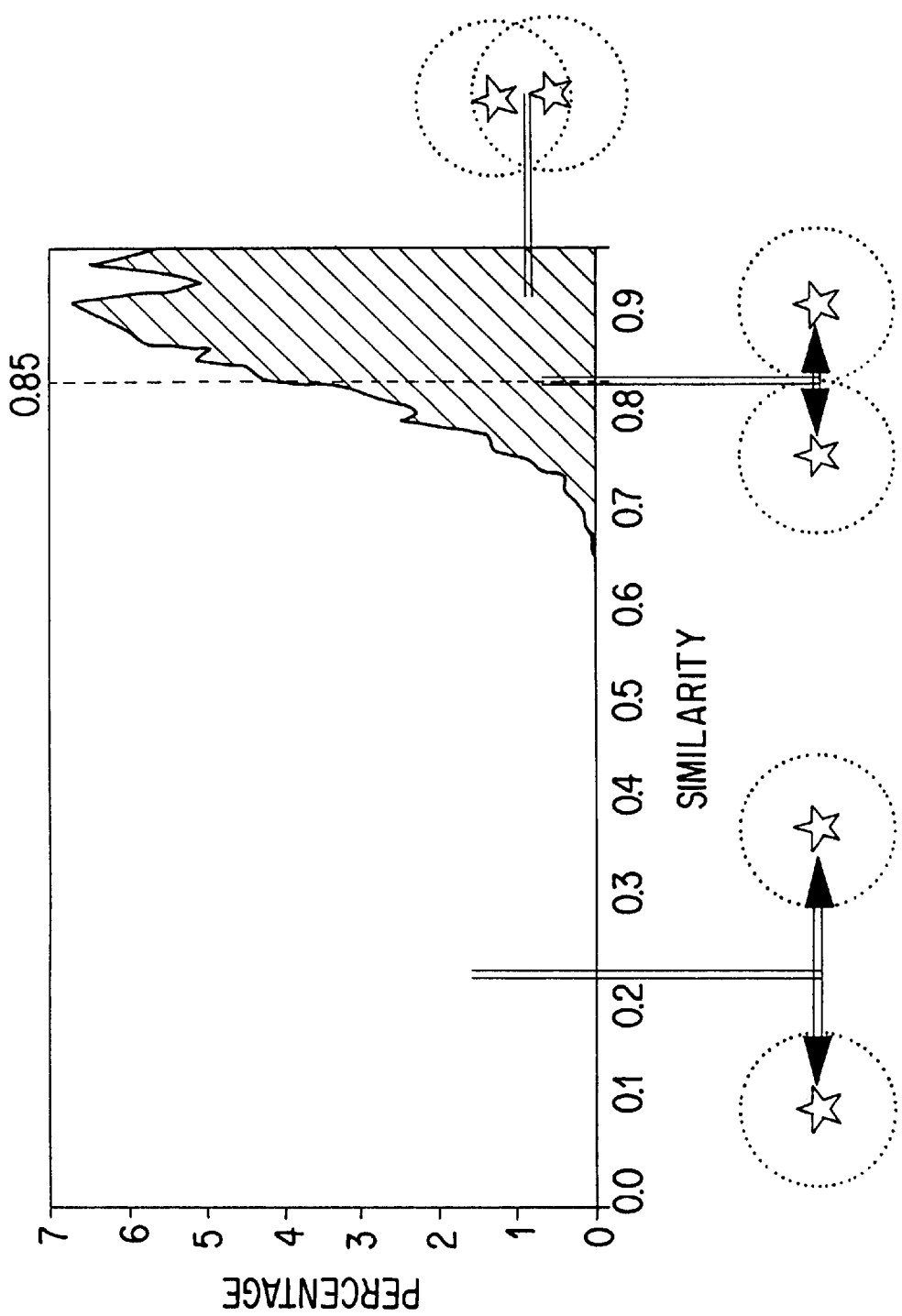
FIG. 13 shows a plot of the Tanimoto 2D pairwise similarities for a typical combinatorial product universe.

Conceptually this selection process is reflected in FIG. 13. FIG. 13 shows a plot of the Tanimoto 2D pairwise similarities for a typical combinatorial product universe in which there has been some selection of reactants based on diversity. As can be seen, a very large percentage of the products have similar structures (Tanimoto coefficients>0.85). The sampling process outlined above results in the following. Molecules having pairwise similarities above approximately 0.85 have overlapping neighborhood radii as shown at 1 and one of each pair is excluded from the library. Molecules having pairwise similarities of approximately 0.85 have almost touching but not overlapping neighborhood radii as shown at 2 and are included in the library. Molecules having pairwise similarities significantly less than approximately 0.85 have no overlapping neighborhood radii as shown at 3 and are also included in the library. Excluding molecules with a Tanimoto similarity greater than 0.85 will eliminate a significant number of molecules in this representative product assembly. This reduction is also reflected in matrix H. While the circles of similarity shown in FIG. 13 represent convenient conceptualizations of the neighborhood distance concept, it should be remembered that most metrics will not define a space in which the "distance" corresponds to an area or volume. In particular, a Tanimoto similarity space does not have this property, yet the "similarity" to a neighbor can be defined and is very useful.

Figure 14:
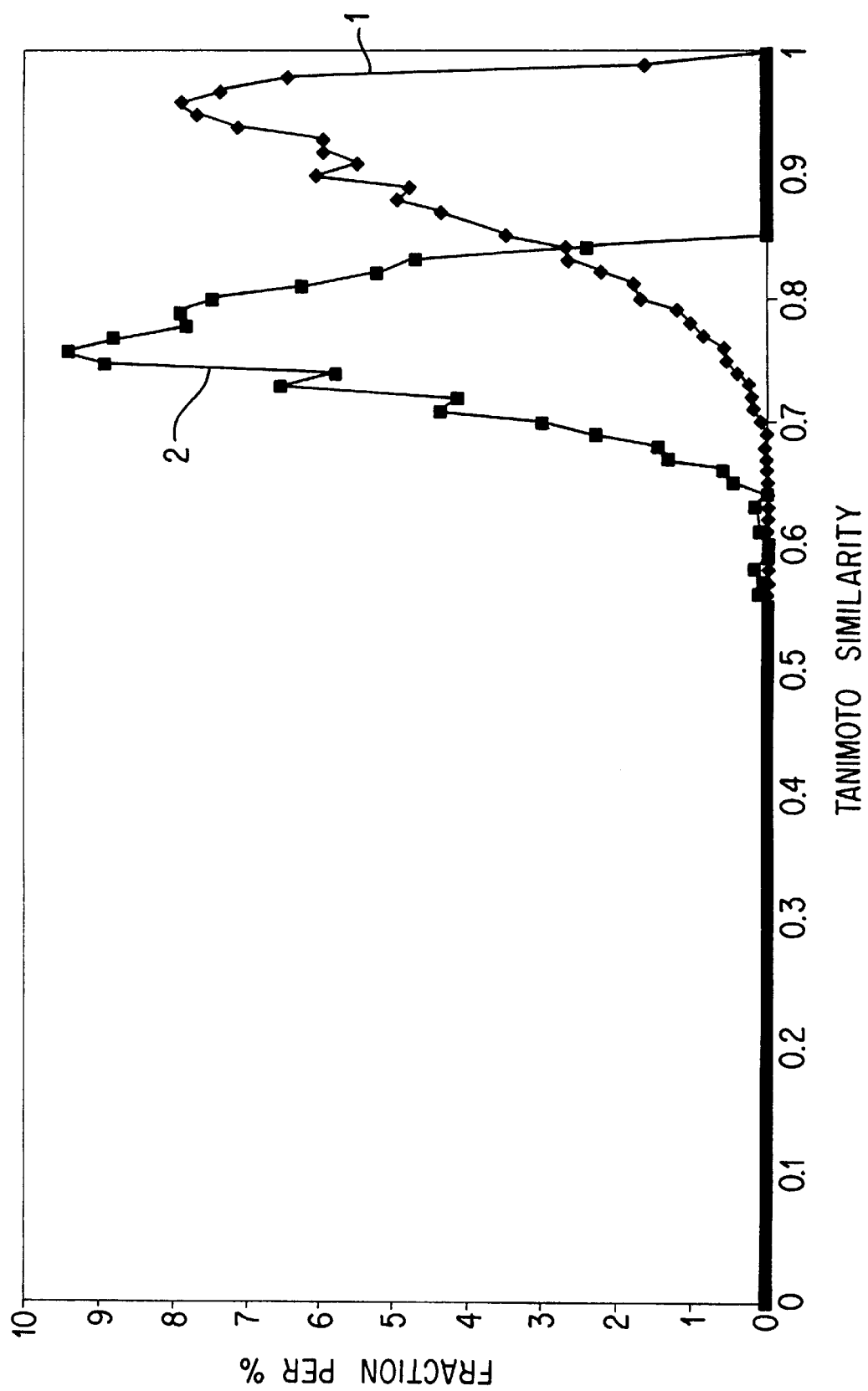
FIG. 14 shows the distribution of molecules resulting from a combinatorial screening library design plotted according to their Tanimoto 2D pairwise similarity after reactant filtering and after final product selection.

A specific example illustrates the dramatic power of the final selection stage in the design process. A proposed combinatorial screening library was designed using thiols and sulfonyl chlorides as reactants. (Many of the same thiols were considered in the study discussed earlier.) The original 716 thiols and 223 sulfonyl chlorides considered would make 159,668 potential products. Topomeric CoMFA analysis indicated that 170 thiols and 61 sulfonyl chloride reactants represented diverse molecules for the purposes of this design and should be used in further library design. 10,370 combinatorial products were now possible. Graph 1 of FIG. 14 shows the Tanimoto similarity distribution of the 10,370 possible products. It can be seen that a large percentage of the possible products were at least 0.85 similar to each other. Following the final stage selection process of the method of this invention, 1,656 product molecules were selected none of which was 0.85 similar to the other. Graph 2 of FIG. 14 shows the plot of the Tanimoto similarities of the final library design products. (The Y axis of the graph is plotted in fraction per % so that the integrated totals are proportional to 10,370 and 1,656 respectively.) The remarkable selectivity of the sampling process is immediately apparent. The products of the designed library have a clearly different similarity profile than the non-selected products. In addition, there has been a greater than 6:1 reduction in the number of product compounds. Thus, from a possible universe of 159,668 potential combinatorial products, 1,656 have been identified which represent the structural diversity of the large ensemble. An approximate 100:1 reduction has been achieved without sacrificing the diversity of the combinatorially accessible universe. As a result of the library design, only the 1,656 compounds have to be synthesized. In addition, these same 1,656 compounds can be tested in any number of biological assays with a high degree of assurance that even in assays with unknown biological activity requirements, these compounds will present the diversity of compounds accessible through this combinatorial universe to the biological assays. Thus there is not only a savings in time and expense in the synthesis and testing of the identified molecules in the library, but it is not necessary to change library design (with concomitant time and expense) each time it is desired to screen a different biological assay. Over time, using the library design of this invention and the process for merging libraries discussed below, it will be possible to build up an optimally diverse combinatorial screening library based on many different combinatorially accessible universes, and this combined library will represent the first real general purpose screening library available to the art—a realization of a long sought after, and previously believed unattainable, goal.

Clearly, other validated whole molecule metrics and their associated neighborhood distances can be used with the sampling process described above to select product molecules for inclusion in a screening library. However, it makes no sense to use the same metric for the products as was used for the reactants. For instance, in the case of the topomeric CoMFA metric, no information would be gained if the metric was used again with the products since all the steric information from the reactants has been transferred to the products. What is critical is that the combinatorial screening library should be constructed by including product molecules which do not fall within the neighborhood radius of other molecules and excluding product molecules which fall within the neighborhood radius of previously chosen molecules. At the end of the design process of this invention, a list of product structures and the reactant sources for each is available in the computer and can be output either in electronically readable or visually discernable form. This data defines the combinatorial screening library. The list of reactants is supplied to synthetic organic chemists. Actual synthesized molecules are then available for testing in the biological assays, typically on multiple well plates. The list of products from each library design can be used to create a definition of a larger combinatorial screening library when merged with other such libraries as discussed below.

The combinatorial screening library designed by the method of this invention is both locally diverse (no two reactants representing the same steric space are present) and globally diverse (no two products having overall similar structures are present). Such a library thus meets the desired combinatorial screening library criteria of being representative of the diversity of the entire combinatorially accessible chemistry universe while at the same time not containing more than one sample of each diversity present (no oversampling). An optimally diverse combinatorial screening library has thus been achieved. By designing an optimally diverse screening library, a reduction in the number of combinatorially generated structures which need to be synthesized and tested of substantially greater than $10^2$–$10^3$ should be possible.

9. Lead Compound Optimization

Unless an entire combinatorially accessible chemical universe is screened, a lead molecule found from screening a library will rarely be the most active or the optimal molecule desired. Therefore, extensive additional work is usually required searching for a related compound possessing the greatest activity or some combination of activity and another desirable feature such as bioavailability. Most of the time, the design of the screening library from which the compound was identified provides little, if any, help in this search. Again, medicinal chemists must resort to traditional methods of lead development. Combinatorial screening libraries based on the methods of this invention provide the means for a directed search of the chemistry space in a way not possible with prior art libraries.

This feature results directly from the fact that the libraries are constructed at each level by selecting molecules which are representative samples of particular molecular diversities. Thus, once a lead is identified, it is a straightforward matter to identify and test compounds representative of the same and/or closely related diversity; ie., it is known how to identify molecules within the neighborhood of the active lead, as defined by the validated metrics used to construct the screening library. Furthermore, the synthetic chemical methods used to construct the screening library are already known and tested and can be used to synthesize additional molecules of the same or similar molecular structural diversity. Since time is always of the essence, especially in exploring a newly discovered biological target, a rational follow up search through an optimally designed library of this invention permits homing in on crucial molecular structures directly and quickly. Not only does this procedure speed up the development process, but it also avoids wasting the time and effort synthesizing and analyzing large numbers of compounds not in the neighborhood of the lead compound which would be erroneously tried prior to knowledge of this invention.

Because the libraries of this invention have been constructed using two selection steps based on molecular structural differences, each step provides an opportunity to identify and explore compounds having similar structural features.

A. Advantages Resulting From Product Filter

Due to the way the final product molecules were selected for inclusion in the library, all compounds with a Tanimoto similarity of approximately 0.85 or greater to a compound already in the library were excluded. Therefore, the first place to look for compounds likely to have the same activity as the lead compound is in the group of all compounds in the combinatorial universe from which the lead was identified having a Tanimoto coefficient with respect to the lead compound of approximately 0.85 or greater. Then, since each of these initial compounds will also have an associated group of different compounds within approximately 0.85 Tanimoto similarity of themselves, this larger group forms the second layer of what can be an expanding area of similar compounds to investigate. How far outwards from the lead compound the search is carried (each time searching within a Tanimoto coefficient of approximately 0.85) will be determined by the success of these additional compounds showing activity in the same assay as the lead compound. Thus, the library design itself identifies and permits a directed search for compounds from the utilized combinatorial universe most likely to have activity similar to the lead compound. The same procedure is followed if another valid metric, not the Tanimoto similarity) was used to create the library. Then all compounds within the neighborhood distance to a compound already in the library were excluded and the first place to look would be for compounds which fall within the neighborhood distance. The process is exactly identical to that followed using the Tanimoto descriptor.

B. Advantages Resulting From Reactant Filter

Two consequences flow from the selection of only one reactant from each cluster. First, combinatorial products containing that reactant may or may not be the most active with respect to any particular given biological screening test. There is no way to guarantee that the reactant that yields the most active product will be selected from the cluster. For any reasonably sized cluster, the probabilities of finding the reactant that yields the most active product would not be greatly increased even if two reactants from that cluster were chosen, and, the size of the library to be tested would have been doubled.

However, the second consequence of selecting only one reactant from each cluster presents the flip side of the selection coin. Once a lead compound is identified, the library design immediately indicates from which diverse clusters the reactant molecules were chosen. All the other possible reactants (in the combinatorial chemical universe under study) representing similar aspects of diversity are included in the clusters from which the reactants were chosen. For lead optimization, compounds containing the other reactants from the identified cluster(s) can be synthesized and tested. The library design itself assures that the exploration of these reactants is likely to yield compounds with similar activity to the lead compound. Thus the reactant selection process not only reduces the number of molecules that need to be screened, but simultaneously identifies the molecular structures which should be subsequently explored to find the compound with the highest activity similar to the identified lead. No other prior art library design process provides so much information for lead optimization.

C. Additional Optimization Methods Using Validated Metrics

The knowledge that a metric is valid, and what that implies for the metric space as discussed earlier, immediately enables methods for lead optimization not previously possible. In particular, knowing that a metric will define a design space where compounds with similar biological properties are found measurably near each other (the definition of a valid metric), now permits for the first time the quantitative examination of the array of molecules used in any screening assay to determine whether any molecules are measurably close to the identified lead compound. One aspect of this approach has already been discussed in sections 9.A and 9.B and certainly works best with an optimal library designed by the method of this invention. In addition, however, validated metrics will permit useful examination of any assemblage of compounds whether or not the lead compound is identified from within the assemblage. There is no restriction on the source of the additional compounds to be examined and they may range from prior art screening libraries to chemical databases. Once a lead is identified, a validated metric would be used to map the lead and all other compounds in the assemblage to be examined into the metric space; ie, the metric characteristics/values are determined for all possible compounds. For reactants (possible substituents) a metric validated on reactants would be used. For whole molecules, a metric validated on whole molecules would be used. Metric differences between the lead molecule and all the other molecules would then be calculated. All molecules with metric distances to the lead within the neighborhood distance of the validated metric should have similar biological activities. Again, if the metric distances from each molecule thus identified as falling within the neighborhood distance of the lead are then calculated with respect to all other molecules (excluding the lead and each other), a second layer of molecules is identified which should have activity similar to the active neighbors of the lead molecule. Additional layers may be similarly identified and explored experimentally. Depending on the structures involved, at least two layers would normally be explored. Thus, because validated metrics are now available, lead optimization will much less often be the hit or miss procedure characteristic of the prior art.

An extension of this procedure yields yet another major advance. In the prior art it was not possible to tell how far away from the lead (in structural terms) one should explore in the search for a compound more active than the lead. In terms of the two dimensional activity island analogy of FIG. 1, no procedure existed for exploring the shape or extent of the island of activity. Without knowledge of the island's shape and extent, not only was it impossible to know by how far a compound missed the island, but even when an active compound was found, it was also not possible to know if the island had been sufficiently explored; that is, whether all compounds representing the range of diversity spanned by the activity island had been identified. In other words, had everyplace been explored that should have been?

With the molecules identified by the expansion procedure outlined above, it will now be possible to map the island. Starting with molecules within the neighborhood distance of the lead, molecules would be synthesized and tested for activity. If all the molecules within the neighborhood distance ("nearest neighbors") show activity, each still falls within the boundary of the island, and the next layer of molecules in the neighborhood distance expansion would be synthesized and tested. If only some of the nearest neighbor molecules show activity, the neighborhood radius of the lead must span an edge of the activity island, and only molecules falling within the neighborhood distance of these nearest neighbor active molecules would be included in the next layer of the expansion and synthesized and tested. Again, some of the newly tested molecules may show activity and some may not. This process of nearest neighbor molecule identification and testing should be repeated until no molecule in the next expansion layer shows any activity. The active molecules determined by this procedure will define the limits and shape of the activity island in terms of structural differences.

The resolution obtainable with this procedure depends upon how well the structural diversity of the activity island is represented by the molecules in the original assemblage. That is, if only a portion of the activity island structural diversity is represented in the assemblage of molecules, that is the only part of the island which can be explored. Alternatively, perhaps only the island's rough outline can be perceived. Within the constraints of the diversity present in the assemblage, exploration of the full extent of the island and of the space within its boundaries can be accomplished with the guidance of the validated metric with which the island is mapped. To explore the island further it is only necessary to identify molecular structures not included within the original assemblage with which to test the unknown territory. In some cases in order to distinguish particular structural differences, it may be necessary to consider additional sources of structurally diverse molecules and, perhaps, to map the lead and additional compounds in more than one metric space. Thus, possible structures can be proposed and examined with the validated metric. If the proposed structures fall within the neighborhood distance of an active molecule, they can be experimentally tested. If those are active, further structures can be proposed and again examined to determine whether they fall within the neighborhood distance of the newly identified active molecule. If they do, they would be experimentally tested. Repeating this cycle of identification and testing will ultimately yield a higher resolution map of the island and assure the searcher that the island has been thoroughly explored and no activity peak has been missed.

The availability of validated metrics enables yet another method of rationally directed lead optimization from a knowledge of the structure of a lead molecule which was not identified from screening an optimally diverse combinatorial screening library. Essentially, the reactant screening process is utilized backwards to identify similar molecular structures, and then the product screening process is utilized to confirm structural similarity of proposed products to the lead. Two cases are important. The first involves lead molecules which can be synthesized directly from reactants. In this method, the lead molecule would be analyzed to determine from what constituent reactants it may be synthesized. These reactants would then be characterized using a reactant metric such as topomeric CoMFA. Molecules in databases of potential reactants would be characterized using the reactant metric and searched for reactants falling within the neighborhood radius of each of the original reactants. The identified reactants will provide a basis for building proposed products having the same structural characteristics (diversity) as the original lead compound. However, before the product is synthesized, its similarity in metric space to the lead would be checked using a product appropriate metric to make sure that it falls within the neighborhood radius of the lead.

The second case involves lead compounds in which substituent groups are bonded to a central or core molecule. The reactants which form the basis of the substituents as well as the core molecule would then be characterized using appropriate validated metrics. Again, molecules in databases of possible reactants and core molecules would be characterized with validated metrics and searched for molecules falling within the neighborhood radius of each of the original reactants and core. The molecules thus identified would provide a basis for building proposed products with structural diversity similar to the lead compound. Again, before synthesis, the proposed products would be evaluated with an appropriate metric to confirm that they fall within the neighborhood distance of the lead compound.

Since it is known that molecules resulting from different chemistries and involving different constituents often show activity in the same biological assay, it would be desirable to search as wide a range of molecules as possible when performing the searches outlined above to identify additional molecules that are within the neighborhood distance of some lead compound. Clearly, when contemplating these procedures, it must be recognized that the universe of all accessible chemical substances, even under the constraints of molecular weight that characterize a useful drug, numbers trillions of structures. While such unprecedented directed searches are only now possible with validated metrics, until the discovery and creation of the virtual library discussed later, even with today's powerful computers, the practicality of such large searches depended on preorganizing the trillions of candidate structures in such a way that the vast majority of candidates could be excluded, to the greatest extent possible, at the start of the search.

For instance, one such useful preorganization involves dividing the candidates into series of molecules accessible by some common synthetic route, and thus describable in terms of a core and reactants. (Typically, the synthetic route used to create the lead would be the first investigated and other sets of alternative routes explored secondarily.) A combinatorial SYBYL Line Notation (cSLN) affords a useful description of such a series of molecules.

Molecules represented by a cSLN would be considered for overall similarity to an active lead molecule in the manner discussed above. Using validated metrics, it is most efficient to: 1) first identify each of the individual lists of reactants within the cSLN with the most similar side chain within the active lead; 2) next, to consider the similarity of the "core" within the lead (the atoms remaining after the side chains are identified) to the non-variant core within the cSLN; and 3) then, if the "core" similarity is not so low that this series of molecules can immediately be excluded, to order the variation lists by similarity to the corresponding side chains within the lead. The advantage of such a partitioning and preordering by similarity is the ability to break off the search as soon as no remaining member of the series would be likely to be sufficiently similar.

As an overly simplistic example, consider the series of sixteen possible dihalogenated methanes which may be represented by a cSLN as: X2CH2X1{X1:F|Cl|Br|I}\{X2:F|Cl|Br|I}.) If bromobenzene were the "active lead" and the dihalomethanes were the series to be considered, an appropriate metric that indicated the lack of similarity of the aromatic core of bromobenzene to the methylene core of the dihalomethanes would immediately eliminate all dihalomethanes without considering each of the sixteen individual possibilities. However, if ethyl bromide were the "active lead", an appropriate metric might show that the methylene and ethylene moieties were sufficiently similar to warrant consideration of the individual methylene dihalides, and preordering of the variation list might immediately lead to dibromomethane as the most similar dihalomethane to ethyl bromide (the first bromine atom being identical to the ethyl bromide bromine, and the second bromine atom probably being the most similar to the $CH_3$ of the ethyl bromide). In this hypothetical example only one molecule instead of sixteen would need to be considered in identifying similar molecules most likely to lie within the same neighborhood as the lead. Within actual cSLNs (each possibly representing perhaps millions of structures by including more points of variation and many more and larger variations at each point), the speed enhancement obtainable from this searching strategy would be many orders of magnitude greater than sixteen.

There may be other variations of the applications of the methods outlined above which are not yet recognized at the present time since the concepts and applications of this invention are still so new. However, reasonable extrapolations/techniques of molecular discovery which follow from the disclosure of the present invention and, in particular, from the ability to validate metrics, are considered within the teaching of this application.

10. Merging Libraries

The final selection (sampling) methodology of this invention has broader uses than yet described. So far, this disclosure has been primarily concerned with the design of a combinatorial screening library based upon either sets of reactants or sets of reactants and central cores. Each combinatorial screening library based on these materials only explores the diversity of that part of the chemical universe accessible with those compounds. Unless as much of the diversity of the entire combinatorially accessible chemical universe is explored in a screening library as is possible, there is no assurance that a molecule possessing activity with respect to any particular unknown biological assay will be found. Clearly, the useful diversity of the combinatorially accessible chemical universe can only be explored with as many sets of reactants attached to as many cores as is possible. Stated slightly differently, there may be large parts of the diversity of the chemical universe not explored by one or even a few combinatorial schemes. Thus, combinatorial screening libraries based on multiple reactants and multiple cores would be desirable. Just such libraries can now be created through the use of the virtual library discussed later. However, even with screening libraries constructed with the method of this invention discussed above, the simple addition to each other of many such libraries will quickly increase the total number of molecules which need to be screened. Worse yet, since many of the possible reactants used for combinatorial synthesis with different cores have similar structures, and since many of the possible cores used for combinatorial synthesis may differ little from each other, it is highly likely that much of the same diversity is represented to a greater or lesser extent in each of the libraries generated from these materials. Simply combining the libraries would again result in oversampling of the same diversity space. It would clearly be more useful and economical (efficient) in terms of time, money, and opportunity to use additional screening to explore different aspects of the diversity of the chemical universe.

Another significant feature of this invention is the recognition that the neighborhood selection (sampling) criteria also provides a method to combine combinatorial screening libraries to avoid this oversampling problem. Starting with an arbitrary first library, using a validated metric which can be applied to whole molecules, each molecule of a second library is added to the first library if the molecule does not fall within the neighborhood radius of any molecule in the first library as supplemented by all the added molecules from the second library. This process is continued until all the molecules in the second library have been examined. In this manner, only molecules representative of a different aspect of diversity are added from the second library to the first. Each successive library is added in the same manner. The molecules in a final combined library formed from smaller libraries selected according to the method of this invention represent diverse molecular compounds and have the optimal diversity which is desired of a general combinatorial screening library. However, even if the groups of molecules to be merged have not been selected by the methods of this invention, they may be merged according to the above procedure if first, a subset of each group of molecules is selected according to the product sampling method of the design process. This will insure that similar molecules within each group are eliminated. The resulting merged library will not be optimally diverse, but it should not redundantly sample the diversity present in the separate groups.

Figure 15:
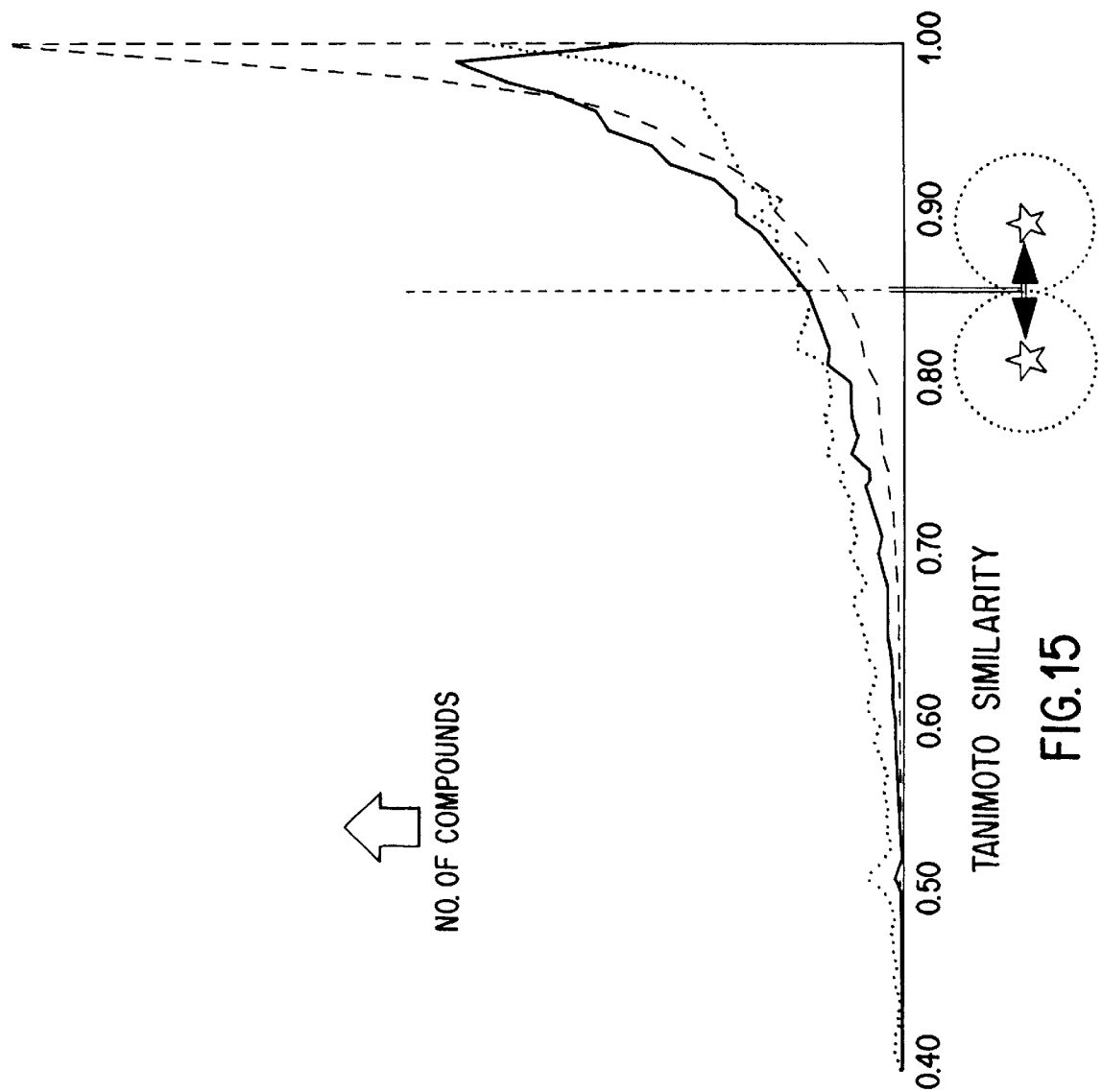
FIG. 15 shows the distribution of molecules plotted according to their Tanimoto 2D pairwise similarity of three database libraries (Chapman & Hall) from the prior art.

The 2D Tanimoto fingerprint metric is useful in performing the library additions. The 2D Tanimoto similarity coefficient of each molecule in the first library to all molecules in a subsequent library are calculated. Each molecule of the second library is added to the first library if the molecule does not fall within a 0.85 Tanimoto coefficient (the neighborhood radius) of any molecule in the first library as supplemented by all the added molecules from the second library. As long as the metric used for sampling and endpoint determination is valid (has the neighborhood property), this selection method guarantees a combined library in which all of the accessible diversity space is represented with little likelihood of oversampling. An example of three prior art libraries not designed with the method of this invention which might be merged using the neighborhood sampling criteria is shown in FIG. 15. FIG. 15 shows the distribution of molecules plotted according to their Tanimoto 2D pairwise similarity of the Chapman & Hall Dictionary of Natural Products, Dictionary of Pharmacological Agents, and Dictionary of Organic Compounds (CD ROM Versions). It is immediately clear from FIG. 15 that simply adding the three libraries together would produce a combined library in which most of the compounds would be very similar to each other (Tanimoto similarities >0. 85). Further redundant similarity would be expected from a comparison of the similarities between the molecules in the three libraries! The position of the 0.85 similarity point to the bulk of the molecules in each library indicates that, most of the molecules in these databases would be excluded from a combined library formed by merging the databases by the procedure outline above.

11. Other Advantages of Optimally Diverse Libraries

There are additional benefits achieved by designing combinatorial libraries according to the method of this invention. For instance, as noted earlier, one of the difficulties of screening several compounds simultaneously is the possibility of non-specific activity being detected due to the contributory effect of the combination of compounds. In fact, the likelihood of this effect is increased when compounds of the same molecular structural and chemical diversity are tested in the same assay. With the libraries of this invention, it will be possible to design the assay combinations so that only compounds representing different aspects of diversity are tested together. While this procedure can not guarantee that no combination effects will occur, it makes it much less likely. Another benefit achieved is that complex deconvolutions will generally be unnecessary. Deconvolution problems are accepted in the prior art as a necessary evil due to the enormous number of molecules which must be synthesized and screened since virtually all combinatorial possibilities are included in the libraries. Clearly, with smaller optimally diverse combinatorial screening libraries covering the same search territory as the larger prior art libraries, it is possible with the aid of computer controlled robots and data bases to individually synthesize and track each compound.

As mentioned at the beginning of this disclosure, the methods of this invention are also applicable to problems outside the specific area of drug research. The notion of choosing compounds based on diversity is a general concept with many applications and is applicable any time the problem is presented of having more compounds than can usefully be tested/used. The example was given earlier of determining what compounds had the same structural diversity as a previously identified (biologically active) compound. Of course, with the methods of this invention, the activity may be any chemical activity. In addition, the universe of chemicals from which only some are to be selected does not have to result from a combinatorial synthesis, but may result from any synthesis or no synthesis at all. An example of the later would be the solution to the question of selecting molecules of similar diversity from among those in a large corporate or catalog data base. In these cases, an appropriate metric (remembering that different metrics are applicable in different circumstances) would be applied to all the compounds and clustering would result in compounds of the same diversity. The methods of this invention, including metric validation, topomeric CoMFA metric characterization, end-point neighborhood sampling, lead compound optimization, and library design can all be applied separately and together to solve the selection problem.

12. Virtual Library Construction & Searching

The two step sequential design process for selecting optimally diverse product molecule libraries set out so far in this application is necessarily computationally time consuming, limited to consideration of one set of synthetic reactions at a time, and eliminates at the first stage reactants which might be capable of generating products which would pass the product stage neighborhood filtering criteria. The process is computationally time consuming since, for any given set of reactants, the steric metric must first be computed, the resulting descriptors clustered, and a selection of reactants made based on the neighborhood rule. Only after this first stage can the possible product molecules be determined, a second product metric calculated, and selection made of the final library members.

The process is limited to one set of synthetic reactions at a time in the following sense. First, a particular organic chemical reaction scheme is identified as well as the core and possible reactants which may be used in the scheme. Each sequential step of library design is sequentially implemented and results in an optimally diverse library for that reaction. For a slightly different core which involves the same chemical reaction scheme and the same reactants, the entire process including all calculations must be repeated. Each combination of core and reactants generates a different library. In the method of the above referenced patent application, the resulting libraries, individually derived, are then combined. This process also adds additional time to the assemblage of a larger optimally diverse library. Finally, the product stage of the design is constrained by the reactant stage; that is, since it is desirable to generate as many diverse products as possible, some products may be sufficiently diverse (as confirmed by the product neighborhood metric) when created from similar reactants (those failing within a topomeric neighborhood cluster) by virtue of the mere combination of the reactants into the products, and such products should be included in the library.

In addition, consideration of the above techniques of optimally diverse library design, lead optimization, and merging libraries all point to the distinct advantages of being able to explore the diversity of combinatorially accessible chemical universes using/including as many reactions, core, and reactants as possible. Thus, it was recognized that, ideally, library design and lead optimization would be most useful if all combinatorially accessible molecules could be meaningfully searched. The sheer number of molecules involved (trillions) would seem to suggest that even with today's fastest computers, such a library design and searching would be unachievable. However, using the power and utility of validated metrics, a way to create and search a data base containing representations of products from as many combinatorial reactions and reactants as desired (a huge combinatorially accessible universe) has been discovered. This data base is essentially a virtual library of combinatorial products because, as will be explained below, all information necessary and sufficient to search across and construct all possible product molecules is contained within the virtual library even though the structure of each combinatorial product is not explicitly contained within the virtual library.

The virtual library can be used not only to select screening libraries, to find molecules with similar structures to a lead compound, to perform lead explosions, but, through the use of validated metrics, it can also be used to search for and select compounds likely to have similar biological or other physical properties from across the broader chemical universe. In fact, as will be seen below, use of the virtual library opens up possibilities for searching the accessible chemical universe in ways not heretofore possible.

With respect to the selection of screening libraries, it has been discovered that the same approach to design as previously described can be performed more efficiently and more exactly by combining the formerly separate steps of topomeric selection of reagents and Tanimoto selection of products into one step which operates on the entire set of all possible products from the reaction under consideration. Another advantage of this approach is that generally a larger group of diverse compounds are identified; that is: the significant (active) metric space is sampled more extensively. Additionally, the method by which the maximally diverse set is selected can be modified to yield results which more readily suit the practical issues of laboratory synthesis. As a consequence of this discovery, an efficient method for identifying molecules of interest from the billions of possible products obtainable from combinatorial syntheses has been discovered. Indeed, use of the virtual library is not limited to finding molecules derivable from known synthetic combinatorial reactions, but is generally applicable to molecular selection. As with the selection methodology discussed above, the ability to create and search the virtual library relies upon the power of the neighborhood property of validated metrics to distinguish the similarity or dissimilarity of molecular properties between molecules.

The creation of a virtual library using validated molecular descriptors enables methods to identify compounds of interest from many possible compounds and is particularly applicable to identifying compounds of interest from extraordinarily large numbers of compounds. The application of these novel methods speeds the searching operation and in some ways extends the types of searching criteria which may be used. Most importantly, construction of a virtual library makes it possible to identify compounds of interest by an exhaustive search through all possible compounds from a series of known synthetic reactions—thus providing a capability which does not currently exist otherwise. In particular, the virtual library provides a large number and variety of ways to select a subset of compounds from a very large number of compounds. The number of compounds from which to make the selection is likely to range in the trillions of compounds, based only on known synthetic reactions and commercially available reagents appropriate for each reaction.

The following disclosure of the method of constructing and searching a virtual library will be discussed with respect to those compounds accessible through combinatorial syntheses. However, as noted above, the virtual library is not limited to such combinatorial compound universes and these universes are disclosed by way of an example of the methodology of the discovery, not a limitation thereof.

The significant aspect of being able to create a virtual library using validated metrics is the ability to identify from the large universe of compounds those with related properties and/or structural characteristics without having to examine individual structures; in other words, to do structural searches without directly comparing (looking at) structures. This is made possible by precalculating, as much as possible, characteristics for the component parts of the product structures. Clearly, then, the beginning point for this method is the construction of a database, or "virtual library", of possible chemical compounds, products, which can be synthesized from a common reaction.

A. Derivation of the Database (Virtual Library) of Compounds

The database of compounds, "virtual library", to which the method of this invention may be applied is an assembly of the combinatorially derived product structures resulting from any number of synthetic reactions. In initial applications tens of reactions are used to construct the database (virtual library) of interest. The total number of possible product compounds becomes astronomically large very quickly. For instance, there are approximately 500 commercially available molecules having reactive diamino groups and approximately 15,000 commercially available reactants which will react independently with each of the amino groups. Combinatorially there can therefore be generated 15,000×15,000×500 (112 billion) possible product molecules from this one reaction scheme alone.

B. Overview of Methodology

A fundamental part of the discovery of how to create and use a virtual library is a method to precompute properties based on $1+N_1+N_2+N_3+\ldots N_M$ structural variations which can be used to exactly, or with useful degree of approximation, predict the $1 \times N_1 \times N_2 \times N_3 \times \ldots N_M$ product structure properties which arise from all combinations of the structural variations about the 1 core at all M substitution sites. In the earlier part of this disclosure, the variable parts of a combinatorially derived molecule were referred to either by reference to their source (reactants) or their molecular configuration when attached to the core (side chains). When discussing creation and searching of a virtual library, the more generic term "structural variations" is appropriate for the groups appended to a core. The reasons for adopting this term will become clear later during the discussion of searching the virtual library with respect to non-combinatorially derived structures.

Figure 16:
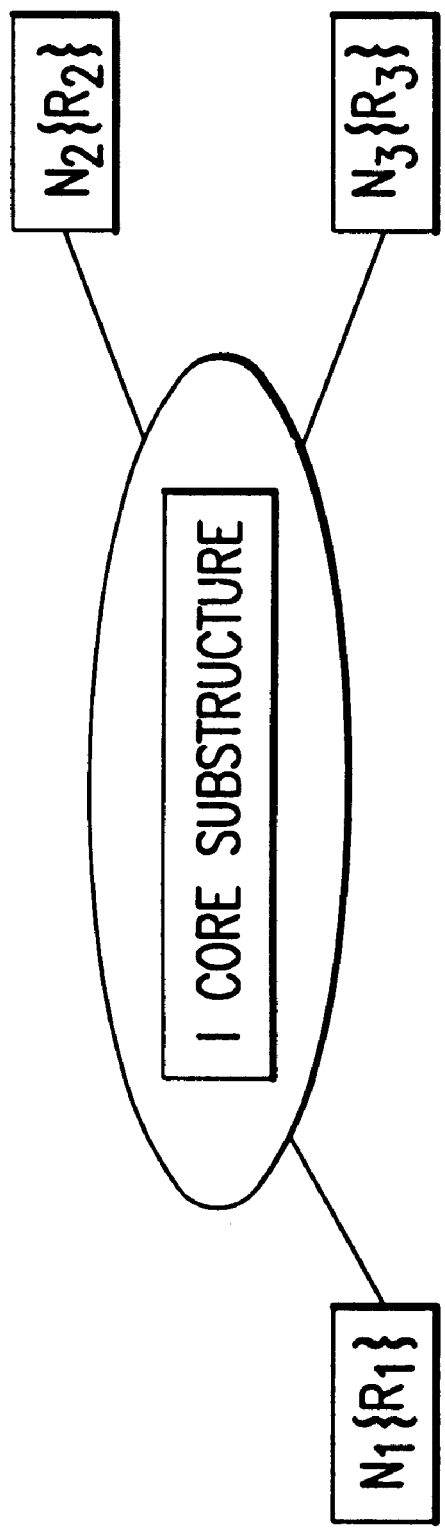
FIG. 16 shows a schematic representation of sets of possible reactants attached to a central core.

FIG. 16 shows in schematic form a representation of three structural variations attached to a central core. In FIG. 16, each possible product structure arises from combining the core substructure with exactly one of the $N_1$ choices in the set of structural variations $\{R_1\}$, exactly one of the $N_2$ structural variations in the set $\{R_2\}$, etc.

For many properties, such as molecular weight and price, or count of rotatable bonds, or number of H-bond donors and acceptors, the values associated with the product compound are exactly the sum of the appropriately created structural variations.

For some properties, such as logP, the assumption of additivity is inexact but adequate for the purpose of selecting a small subset from a very large number of possible products. For other properties, particularly the topomeric shape descriptor, the comparison of two product compounds' properties requires a decision on how to match each structural variations's descriptor in the first product to one structural variations's descriptor in the second product such that each structural variation is referenced exactly once.

There are also some properties (such as molecular fingerprints) which are representative of the whole combinatorial product molecule and can not be represented by the sum of the constituent structural variations. The method for deriving these properties will be discussed below. Generally, however, by this method a virtual library containing descriptions of the structures of all possible combinatorially generated products can be created from a knowledge of the properties of the structural variations.

C. Overview of Virtual Library Construction

Figure 17:
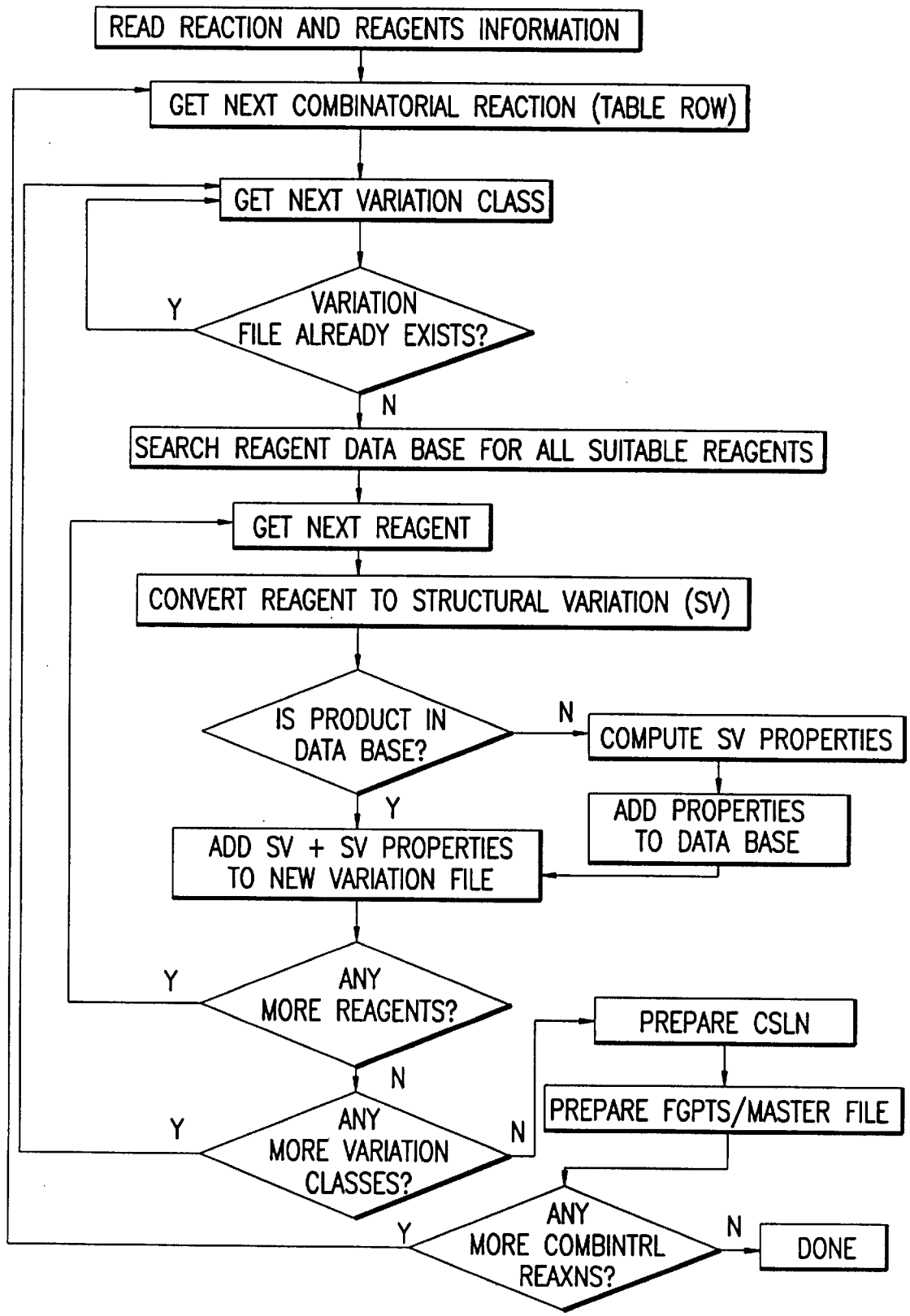
FIG. 17 is a flowchart summarizing the overall process of virtual library construction.

Initially information on the reactions to be included and the reagents which may be used with those reactions needs to be gathered and entered. In addition, the reagents need to be converted to their corresponding structural variations. The overall process of virtual library construction is summarized in the flowchart of FIG. 17. The first step in the creation of the virtual library is to create for each possible structural variation (variable part) a file containing various parameters/characteristics associated with that structural variation. Typically the file may contain information on the price, source, availability, MW, and logP. In addition, the metric characteristics for the structural variation resulting from the application of validated metrics to the structural variation structure are included in the file. Other characteristics which might be used for searching may be added to the file. Similar files are created for core structures. As with the earlier discussion of designing optimally diverse libraries, any validated metric may be chosen to characterize the structural variations or cores. For purposes of discussion of the virtual library, the same metrics, topomeric CoMFA and Tanimoto fingerprints, will be used as in the examples earlier.

The second step in creation of the virtual library is a description of the chemical transformation represented by the chosen chemistry. The virtual library is then created by combinatorially combining all structural variations in the chemical transformation to generate virtual library descriptions of all possible product molecules.

Substantial effort is required to produce the representation of the structural variations forming the database from a given reaction. The software provided as Appendix "E" and Appendix "F" to this application is used in conjunction with the commercial software products, Selector and Legion, to compute properties of the structural variations and to combine two or more such lists of structural variations along with a core structure to produce the representation of all possible products.

Particular skill is required to convert the chemist's description of reaction conditions and reaction validation into a set of selection criteria applied to a database of available reagents, by which only those reagents which are actually likely to yield the desired product in the specific reaction conditions are included. (Here "reagents" refers to chemical starting materials which undergo reaction to produce the products. A reagent corresponds to a molecule used in a structural variation in the method, after some rearrangement of bonds.) Additionally, methods for automating chemical judgment to derive the list of reagents and to compute the properties such as the topomeric shape descriptor have been developed. Finally, a key concept in constructing the virtual library is to organize the process of library definition so that it depends on a relatively small number of parameters which can be stored in a table so that each row in the table defines all the information that is necessary to specify a combinatorial library. While the following discussion addresses formation of the virtual library in terms of chemical transformations, cores, and reagents and/or structural variations which may be used, it should be appreciated that data in the virtual library may be generated by any cores and structural variations as long as the resulting compounds can be described by a cSLN. Thus, even product molecules which can not be synthesized by a known combinatorial reaction can be included in the virtual library and their structures searched.

D. Virtual Library Construction

The first phase of construction of a combinatorial library to be included in the virtual library takes as input a description of the chemical transformation represented by that combinatorial library and a list of available reagents and produces as output all the part structures (a/k/a structural variations) found in the list of available reagents which are appropriate for the chemical transformation, along with all structure-invariant physicochemical properties of those fragments that might be useful in different types of subclass (subset) searches. As is apparent from the earlier discussion, the same general and biologically based elimination criteria can be applied to the proposed structural variations before selection of the structural variations for inclusion in the virtual library. Alternatively, structural variations which would be eliminated by the general or biologically based criteria can be flagged but still included. Having the structural variations flagged, few potential product structures are eliminated from the virtual library, but the products containing particular types of undesirable structural variations can still be removed during selection.

In the course of this process, data are entered and recorded permanently into three tables:

| | |
|---|---|
| REACTIONS | (a Molecular Spreadsheet) = information about a reaction scheme. Each record corresponds to a reaction. A typical reaction would be: "reaction of each nitrogen of a diamine with various reagents such as acids (acylation) or ketones (reductive amination)". |
| REAGENTS | (a Molecular Spreadsheet) = information about a particular set of reagents used in some instance of a reaction. Each record corresponds to a particular logical reagent structure search in a database of such reagents, presumably a set of reagent structures which will all react in the same way. For example, there are sixteen reagent records for the diamine reaction, enumerating each of eight reactant classes that might react with each of the two nitrogens. One record for example describes a reaction with epoxides, that could be ring opened nucleophilically (and regioselectively) by an amine to yield a beta-amino alcohol. |
| RDATA | (an Oracle Table) = invariant physicochemical data computed about structural variations, typically the varying portions in a CSLN, with one record for each structural variation encountered in any cSLN constructed. Thus data need not be recomputed when such structural variations are reencountered, a substantial savings in processing time. For example, records will be added describing the properties of a —CH2CH(OH)R chain (structural variation) for each (new) epoxide-R reagent retrieved by the example record just given for the REAGENTS spreadsheet. |

Entering a new reaction into the system involves inputting the data for a new row to REACTIONS and at least two new rows to REAGENTS. This data entry operation is the only required data entry in preparation for virtual library production.

All these operations of table preparation are carried out by the SPL script getacd.core (Appendix E) and executed within the commercially available software product SYBYL. The code for producing the topomeric CoMFA field descriptor of each structural variation is provided as Appendix F, CTOPS.

i. Representation of the Database of Compounds

The virtual library database of compounds for any one synthetic reaction is represented as a set of chemically bonded (connected) structural variations where the connecting elements may consist of a common core (one or more atoms which are identified in all members of the set). More than two variable sites may be involved. The list of structural alternatives therefore contains two or more elements, each of which represents a specific molecular fragment and a number of associated molecular properties. Table 6 and Table 7 below are produced by getacd.core. For each combinatorial scheme a set of files is generated. For a di-substitution scheme the first file defines the combinatorial scheme, and the second and third files describe the structural variations which can be utilized at the two sites. For a tri-substituted scheme, there will be a set of four files: the first defining file, and three additional files describing the structural variations for each of the three sites. The number of files in each set of files is clearly determined by the combinatorial scheme involved.

In Table 6, the information following #@CORE describes the core, the information following #@CONNECTOR describes the location of attachment of each of the two varying sites, and the #@QUERY line shows an example of how the list of structural variations may be specified. Essentially this QUERY describes how to combinatorially construct product molecules out of the structural variations and is used after searching of the data base is complete to generate actual product structures.

TABLE 6

Sample cSLN File

SYBYL/3DB HITLIST
Created: Date Time
@CLASS STRLIST
@DATABASE NONE
@SOURCE VDB_BUILDER
@SUPPLIER
@PRICE
@FCD
@MW 85.062
@LOGP −1.05
@CORE X1C(=O)CH2NHC(=O)X2
@CONNECTOR 1,X1=2;11,X2=9
@QUERY
Y_01C(=O)CH2NHC(=O)Y_02{Y_02:FC(F)(F)C[5]:C:C(:CH:CH:CH:@5)C(F)(F)F<V=6>}\
{Y_01:FC(F)(F)C[5]:CH:C(:CH:C(:CH:@5)OCH3)NH<V=19 >} ii. Application of a First Metric (Topomeric CoMFA)

Table 7 shows the format in which the structural variations for the first variable site are listed, including both the structure in Sybyl Line Notation (SLN) and a set of related properties such as SUPPLIER, PRICE, molecular weight MW, estimate of hydrophobicity LOGP, and a field, CTOPS, which in encoded form represents the novel shape descriptor, the topomeric field (the steric field of the topomeric conformation) for the corresponding structural variation. Information on only two possible structural variations is shown. For the diamino example above, this structural variation file would contain all of the structural variations which react with an amino group, approximately 15,000 entries.

TABLE 7

Structural Variations At First Site

FC(F)(F)C[5]:CH:C(:CH:C(:CH:@5)OCH3)NHR1 < FCD = TRIPOS_0393;PRICE = 101.4
;SUPPLIER = ALDRICH;MW = 190.14;LOGP = 2.33;CTOPS = 111111111111111111111
1111111111111111111111111111111111111111111111111111111111111111111111
1111111111111111111111111111111111111111111111111111111111111111111111
1111111111111111111111111111111111111111111111111111111111111111111111
1111111111111111111111111111111111111111111111111111111111111111111111
111111111111111111111111a111111113f21111111141111111111111111111111111
11111111111111111111111111111111111111111111112f1111111ffe11111114ff111111
11ff311111112f11111111111111111111111111111111111111111111111111112fff111
1115ff31111112ff21111111fff1111111ff411111111111111111111111111111111111
1111112111111111fff1111111fff2111111fff1111111ff11111119421111111111111111111111
1111111111111111111111111111111111ff11111114ff11111111711111111111111111111
1111111111111111111111111111111111111111111111111111111111111111111111

TABLE 7-continued

Structural Variations At First Site 11111111111111111111111111111111111111111111111111111111111111111111
1111111111111111111111111111111111111111111111111111111 >
FC(F)(F)C[5]:CH:C(:CH:C(:CH:@5)C(F)(F)F)NHR1 < FCD = TRIPOS_0394;PRICE = 14
.84;SUPPLIER = ALDRICH;MW = 228.12;LOGP = 3.32;CTOPS = 11111111111111111111
11111111111111111111111111111111111111111111111111111111111111111111
11111111111111111111111111111111111111111111111111111111111111111111
11111111111111111111111111111111111111111111111111111111111111111111
11111111111111111111111111111111111111111111111111111111111111111111
1111111111111111111111111a1111111113f21111111141111111111111111111111
111111111111111111111111111111111111111111111112f111111111ffe11111114ff1111
1111ff31111112f11111111111111111111111111111111111111111111111111112ff11
1111115ff11111112ff21111111fff1111111ff4111111111111111111111111111111111
1111111111111111111fff11111111fff1111111fff1111111fff11111119421111111111111111111
11111111111111111111111111111111111ff21111111ff41111113f11111111111111111111
11111111111111111111111111111111111111111111111111111111111111111211111
11111111111111111111111111111111111111111111111111111111111111111111
1111111111111111111111111111111111111111111111111111111 >

A second file similar in appearance to that of Table 7 which lists all the structural variations which may occur at the second site is also created.

iii. Application of a Second Metric (Tanimoto Fingerprint)

Figure 18:
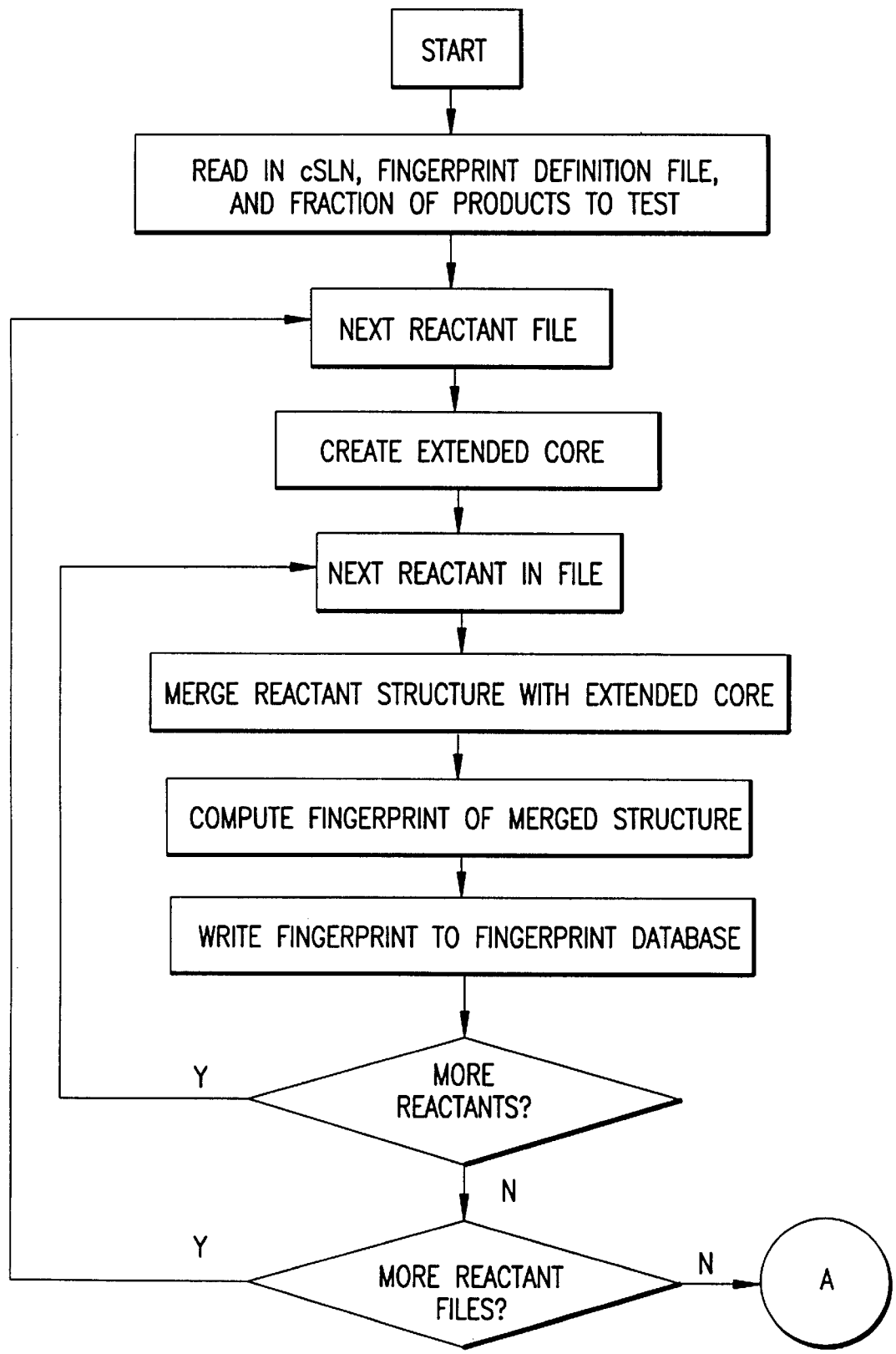
FIGS. 18, 19, and 20 are a flowchart summarizing the overall process of applying the Tanimoto fingerprint metric for use in the virtual library.
Figure 19:
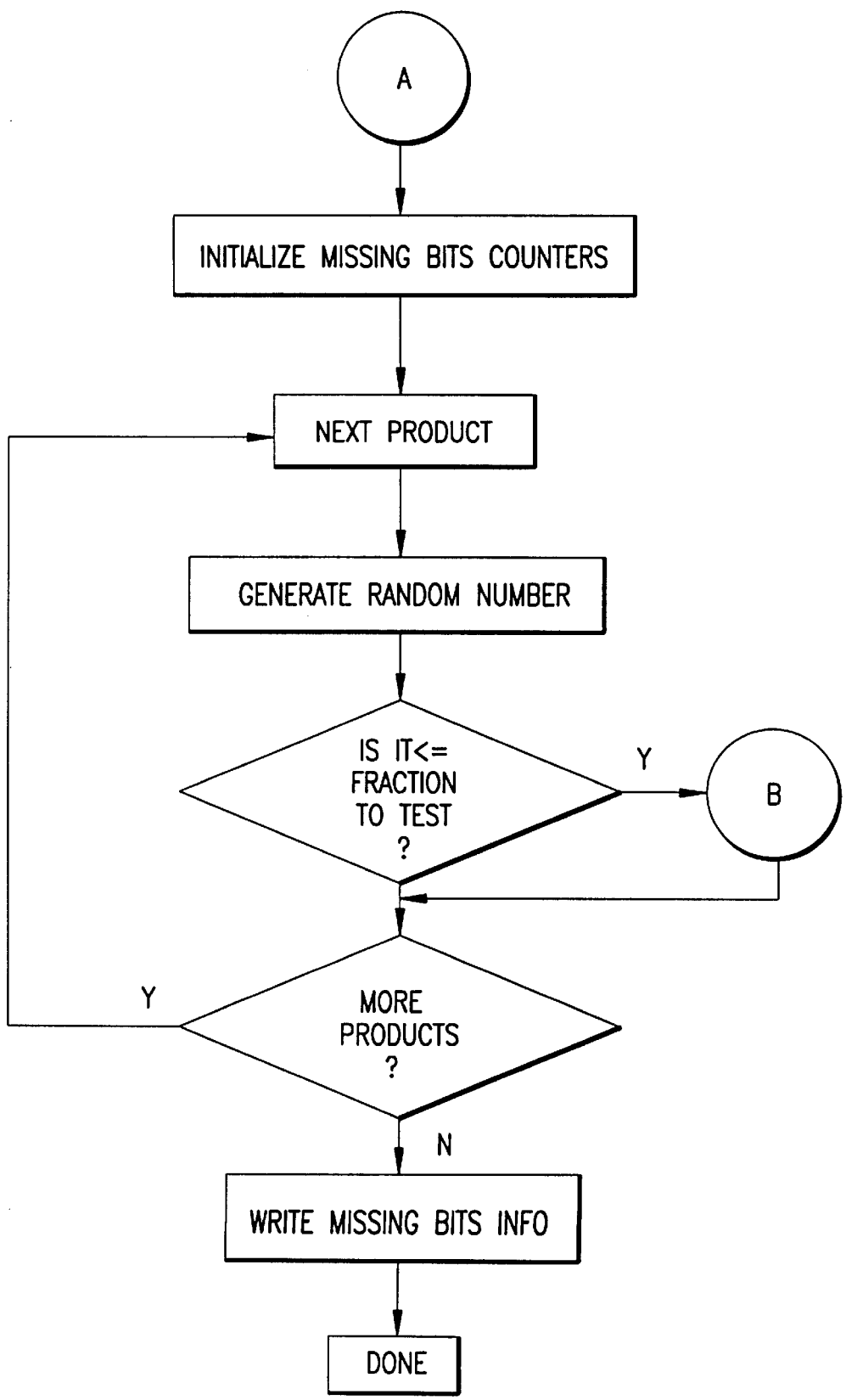
Figure 20:
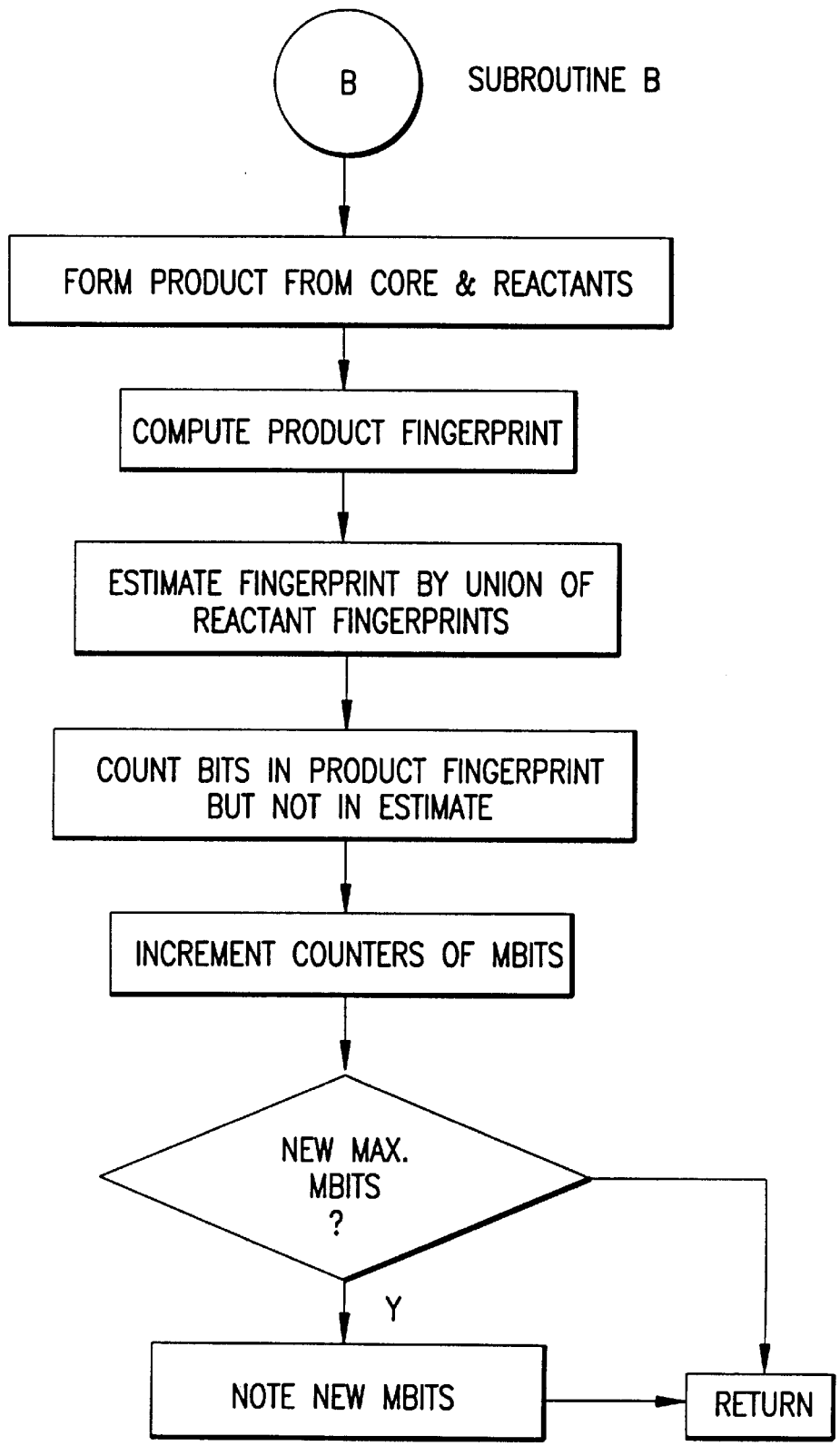

The overall process of applying the Tanimoto fingerprint metric for use in the virtual library is summarized in the flowchart of FIGS. 18, 19, and 20. As mentioned above, certain properties (molecular descriptors) of the product molecules can not be simply computed as the sum of the associated properties of the substructures used to form the product molecule. One of the most important and challenging to compute of these molecular descriptors is the molecular fingerprint. This product descriptor can not be calculated as the simple additive results of the descriptor of its pieces. For fingerprints, any fragment which is not fully contained within the core alone or within one structural variation alone will not be represented by treating each piece separately. Therefore, a fingerprint descriptor is computed for an extended core consisting of the structural variation at site $R_1$ and including the substructures which consist of:

1) the structural variation;
2) the common core substructure; and
3) all invariant atoms contiguously connected to the core occurring in structural variations at sites other than $R_1$.

This process is repeated for all sites.

Thus, in FIG. 16, if each selection in $\{R_2\}$ includes an OCH2 group connected to the core and each selection in $\{R_3\}$ contains a CH connected to the core, the fingerprints corresponding to a selection from $\{R_1\}$ will describe the substructure formed by this selection connected to the core and also including an OCH2 connected to the core at site 2 and a CH connected to the core at site 3.

For the standard definition of 2D fingerprints, this method can yield an exact result of the product fingerprint whenever the shortest connected path through the extended core is 5 atoms or more by OR-ing (a Boolean algebra manipulation) the fingerprints of each of the 3 structural variations in the example above. There is no need to include a separate fingerprint for the core, since it is contained in all the structural alternative descriptors. There is no hazard of duplication, since a fingerprint with a few exceptions notes only the presence of a connected fragment, not the number of occurrences. That is; either a bit is set in the fingerprint for that structure or it is not set. Duplicate occurrences of the same structure can not set the bit twice. In the few cases, such as ring and halogen structural features, where a count is maintained, correction for these bits of the fingerprint may be accomplished by explicit correction by count of structural variations plus core.

In some cases the extended core is not large enough to assure exact construction of the product fingerprint from that of the pieces (i.e. some relevant fragments start in one structural variation, span the extended core and reach into the individual alternatives at another site). To create and explicitly fingerprint every compound is in fact possible for a set of one million products. For the creation of a virtual library with initially tens of millions of products and ultimately hundreds of millions and even hundreds of billions of product compounds, explicit fingerprint computation is not feasible in any realistic time frame. For this scale of virtual library creation an approximation is both acceptable and necessary. Finally, since the purpose of the creation of the virtual library is to provide a basis for searching for molecules matching some subset criteria, the approximation method must ensure that such searches are reliable.

For the approximation, a random sample of a statistically significant fraction (typically for a very large virtual library, 0.001) of the products is taken. Each sample product is checked to see how many bits are in the product but not in the fingerprint composed from the pieces. The largest observed difference value, MBITS, is maintained for future calculations and is used to identify, for example, all products which might be similar to a given structure in the extreme case in which all MBITS missing bits were in fact those which would make every product most similar.

The Tanimoto is defined as (#bits in common)/(#bits in either) for the similarity of two compounds' fingerprints. In the case at hand, the estimated product fingerprint might have as many as MBITS bits which are actually present in the product fingerprint but missing from the estimate. In the worst case, every one of those bits would be in common with the bits in the query compound's fingerprints. Since Tanimoto=(#bits in common)/(#bits in either), in our worst case this is (apparent #bits in common+MBITS)/(#bits in either), since every one of the MBITS bits is already represented in the #bits in either but is not present in the apparent #bits in common (i.e. the #bits in common based on the estimated product fingerprint).

By adopting this approach, an upper bound is calculated on the largest possible Tanimoto between two compounds. The actual product fingerprint cannot yield a higher Tanimoto than this, and almost always yields some value between the apparent Tanimoto and the upper bound. In some cases this estimates the largest possible Tanimoto to be greater than the actual maximum of 1.0; it serves no purpose to correct for this!

An example may be useful. Details of the computations are provided in the attached code, dbcslnprepro, but to illustrate the concept assume that what is desired is a subset of compounds defined as those with a Tanimoto similarity of 0.80 or higher to a specified reference compound. By the alternative's structure is augmented is that of the core. Appendix G contains the code dbslnprepro which calculates and adds fpcard and fp.

When the fingerprint terms, fpcard and fp, are added to the file structure shown in Table 7, the complete file format for each structural variation follows the form:

TABLE 8

FC(F)(F)C[5]:CH:C(:CH:C(:CH@5)OCH3)NHR1 < FCD = TRIPOS_0393;PRICE = 101.4
;SUPPLIER = ALDRICH;MW = 190.14;LOGP = 2.33;CTOPS = 1111111111111111111111
1111111111111111111111111111111111111111111111111111111111111111111111
1111111111111111111111111111111111111111111111111111111111111111111111
1111111111111111111111111111111111111111111111111111111111111111111111
1111111111111111111111111111111111111111111111111111111111111111111111
11111111111111111111111111a1111111113f2111111114111111111111111111111111111
1111111111111111111111111111111111111111111112f11111111ffe11111114ff111111
11ff311111112f11111111111111111111111111111111111111111111111111111112fff111
1115ff31111112ff211111111fff1111111ff411111111111111111111111111111111111111
1111112111111111fff1111111fff2111111fff1111111fff111111119421111111111111111111111
11111111111111111111111111111111111111ff11111114ff11111111711111111111111111111
1111111111111111111111111111111111111111111111111111111111111111111111
1111111111111111111111111111111111111111111111111111111111111111111111
111111111111111111111111111111111111111111111111111111;fpcard = 141;fp = 08000020
2000008002080008804080481000000008003280c42a1010000000100f888044011824c809000
4000200080000e0088004202040028100000000000112010a80000400111800000c2184c0060a8
06180480001810200000000020000002481201020a024008c800040100000520000118476e0c000
38e7c10100 >
FC(F)(F)C[5]:CH:C(:CH:C(:CH:@5)C(F)(F)F)NHR1 < FCD = TRIPOS_0394;PRICE = 14
.84;SUPPLIER = ALDRICH;MW = 228.12;LOGP = 3.32;CTOPS =1111111111111111111111
1111111111111111111111111111111111111111111111111111111111111111111111
1111111111111111111111111111111111111111111111111111111111111111111111
1111111111111111111111111111111111111111111111111111111111111111111111
1111111111111111111111111111111111111111111111111111111111111111111111
11111111111111111111111111a1111111113f2111111114111111111111111111111111111
1111111111111111111111111111111111111111111112f11111111ff211111114ff1111
11111ff311111112f11111111111111111111111111111111111111111111111111111112ff11
111115ff11111112ff211111111fff1111111ff411111111111111111111111111111111111111
1111111111111111fff1111111fff1111111fff1111111fff11111119421111111111111111111
11111111111111111111111111111111ff211111111ff411111113f1111111111111111111
1111111111111111111111111111111111111111111111111111111111111111211111
1111111111111111111111111111111111111111111111111111111111111111111111
111111111111111111111111111111111111111111111111111111;fpcard = 121;fp = 0800002
02000008000080008800080480000000008003280442a0010000000100f008044011024c80900
04000200080000e0088004200040028100000000000100129900000400111900040821848060
880618048000101020000000020000002081201080200084800040000000042000001847c0c0
003cff810100 > methods of this invention the fingerprints of every one of the 2000 structural variations at two sites (1000 each) have been precomputed. An estimate can be made of the fingerprints of every one of the 1,000,000 possible products by OR-ing the two site's fingerprints for every selection of one from each site. For a specific possible product the number of common bits is 78 and the "# of bits in either" is 100, so that the apparent Tanimoto is 78/100 which is below the cutoff of 0.80 and the product would not be selected. However, if the MBITS is 3, then the worst case could have 78+3=81 bits in common out of 100 bits in either, and the largest possible Tanimoto would be 81/100 which is greater than the cutoff. If it is desired to err on the side of not missing any possible products, this value would be accepted even though the apparent Tanimoto is too small.

The results of the fingerprint calculations discussed above are added as two additional fields to the structural variation files: fpcard and fp, which together represent the two-dimensional fingerprint of the structural alternative and everything to which it is connected in all of the resulting products; this additional structure being needed to more fully represent the fingerprint of a product compound by that of the structural variations which combine to form it. At the minimum, the common structural portion by which the When initially constructed the virtual library consisted of the files described above. However, since the fingerprint metric is calculated for each set of structural variations attached to a specific core, separate structural variations files containing the fingerprint data were required for each combination of core with the structural variations. The virtual library therefore contained a great deal of redundant data (structural variation files repetitively containing the same non-fingerprint data). Accordingly, a more efficient virtual library is constructed by locating the fingerprint files associated with each structural variation file and different cores in separate files. Thus, only one copy of each structural variation file (like Table 7) is required, and there is an associated fingerprint file containing fpcard and fp for every core with which the structural variation file is used. The virtual library keeps track of all the individual files in a master file. For instance, on one line of the master file is kept the information that the Table 6 file is associated with its appropriate structural variation files and fingerprint files. Each line of the master file relates one Table 6 like file (CSLN) file with the appropriate structural variation files and fingerprint files. The same structural variation files may now be used with more than one cSLN as long as the same type of chemical reaction is involved. Appendix G contains the code dbcslnprepro (a/k/a "power") which calculates fpcard and fp, writes the fingerprint files, and updates the master file.

Clearly, the data associated with each structural variation in each file can be directly expanded to include the results of the application of any other validated metric to the structural variation.

iv. Summary of Method & Scope of Chemistry

Creation of a virtual library of structural variation files along with one definition file is all that is needed to describe all the products of a combinatorial synthesis, that is; all possible products of the combinatorial synthesis are now described using only descriptors of the structural variations. As many additional combinatorial synthesis may be added to the virtual library as is desired. Clearly, the larger the number, the more comprehensive will be the universe of accessible compounds which can be searched. In this manner the $N_1 \times N_2 \times N_3 \times \ldots$ number of products may be analyzed using only the $N_1+N_2+N_3+ \ldots$ number of structural variations. This ability to search a geometrically large number of product structures by searching through only the arithmetic sum of their parts is the key feature of the virtual library and is possible because of the identification and use of validated descriptors possessing the neighborhood property. Clearly, this same method is equally applicable to any large assembly of compounds not derived from a combinatorial synthetic scheme which can be described as combinations of structural variations. Any number of additional fields containing information about the structural variation may be added to the file format, and may be meaningfully used as part of the search criteria for subset selection.

There is special merit in assuring that each product which a user may select from this database (virtual library) corresponds to a known synthetic route and known available reagents. However, the routines which the user applies to select subsets of the virtual library, described below, do not depend on this. Neither does the representation itself inherently depend on the assumption of known synthesis pathway. Therefore it can be applied to any situation in which the set of compounds of interest can be expressed concisely as a core and points of enumerated structural variations. This makes the scope of the method, in principle, cover virtually all of small molecule chemistry. In the limit, any molecule is divisible into such a representation where there may be only one "structural variation" known in each list. In fact, the practical advantages of the invention will only obtain when the number of structural variations is large.

E. Searching the Virtual Library

The techniques of constructing and searching the virtual library present the molecular researcher with powerful methods of discovery not previously possible and represent another major advance in the state of the art. Since the virtual library is constructed for purposes of finding molecular similarities in structure and function, a unique feature of the virtual library is that you can ask questions of similarity in two fundamental ways—providing, essentially, two sides of the same coin. The first way is in the design of screening libraries—subsets of the virtual library where what is sought are all those product molecules meeting some set of similarity criteria and not their structurally and/or functionally equivalent neighbors (as illustrated in FIG. 1B). The second way is in expanding on a lead compound (lead explosion)— subsets of the virtual library where what is sought are all those product molecules meeting some set of similarity criteria to the lead and all the structurally and/or functionally equivalent neighbors. Clearly, as a given line of inquiry is followed, the search for the desired subsets may, at any given level of detail, take on aspects of one or the other of these two methods of inquiry. For instance, a search for all product molecules matching a lead compound may result in 10 million possibilities. In order to make the synthesis and actual screening more efficient, out of these 10 million, a screening library may be selected which does not sample the same neighborhood space more than once. This ability to perform different types of similarity searches underlies the discussion which follows.

Any of the characteristics associated in the virtual library file with each structural variation may be searched separately or in conjunction with other characteristics. Since validated metrics are used as descriptors for each structural variation, it is possible using only the data contained in the structural variation files to quickly identify those product molecules which could be formed from the structural variations similar in structure and biological activity to known molecules (such as lead compounds) or arbitrarily chosen molecules (screening libraries). With the virtual library, a structural search can be carried out without having to actually generate and compare any explicit structures of any possible product molecules. Subset libraries (screening libraries) representing molecules with selected characteristics can thereby be directly created by a search of the virtual library, and product structures created and generated only for those molecules included in the subset library. It is important to understand that the virtual library can be formed from any number of combinatorial synthetic schemes or can include molecules which, while not based on a combinatorial synthetic scheme, may be expressed in the form of a cSLN. Methods of including and searching such molecules will be discussed below. Not only does the discovery of a way to create the virtual library make it possible to search an extraordinarily large number of possible molecular structures, but it also makes it possible to do the searching in an extremely efficiently manner and in a very short period of time.

Since a variety of data associated with each structural variation, including that resulting from the application of validated metrics, is stored in the virtual library, the range of questions (searches) and the types of answers (subset libraries) one can ask of and receive from the virtual library is virtually unlimited and the number of possible product molecules examined to answer the questions is extraordinarily large. As emphasized earlier, the virtual library associates precomputed metric values with each structural variation. Library searching is based on the discovery that the metric characteristics of product molecules can be usefully estimated by the metric values of the structural variations used to form the products. As has been seen above, in the case of the Tanimoto fingerprint, it was also necessary to take into consideration in preparing the precomputed metric values some estimation of the core structure. For topomeric field searching, a useful method of comparison involves taking the root mean sum of squares differences between the metric field values of one structural variation and another. This value can then be compared to a chosen neighborhood distance to determine similarity. Finally, it should be recognized that in discussing core structures used in combinatorial arrangements, for purposes of creating and searching the virtual library, it is possible to consider a singe bond as a core structure. In such a case, the structural variations would be combinatorially combined across a single bond.

As presently implemented by the inventors, the virtual library has to date 170 billion possible product compounds representing 70,000 combinatorial reaction schemes over various cores, and it is being expanded monthly. The sheer size of the virtual library suggests that search times must be similarly enormous. However, using the search methodology described below, made possible by the construction of the virtual library based on validated metrics, real world searching rates of greater than 200–500 million compounds per hour have been routinely achieved with a single processor. Higher rates are achievable on a parallel processing computer with multiple processors such as are now available from several vendors including Silicon Graphics, Inc.

i. Example Search Routine of Virtual Library—Tanimoto Similarity

Figure 21:
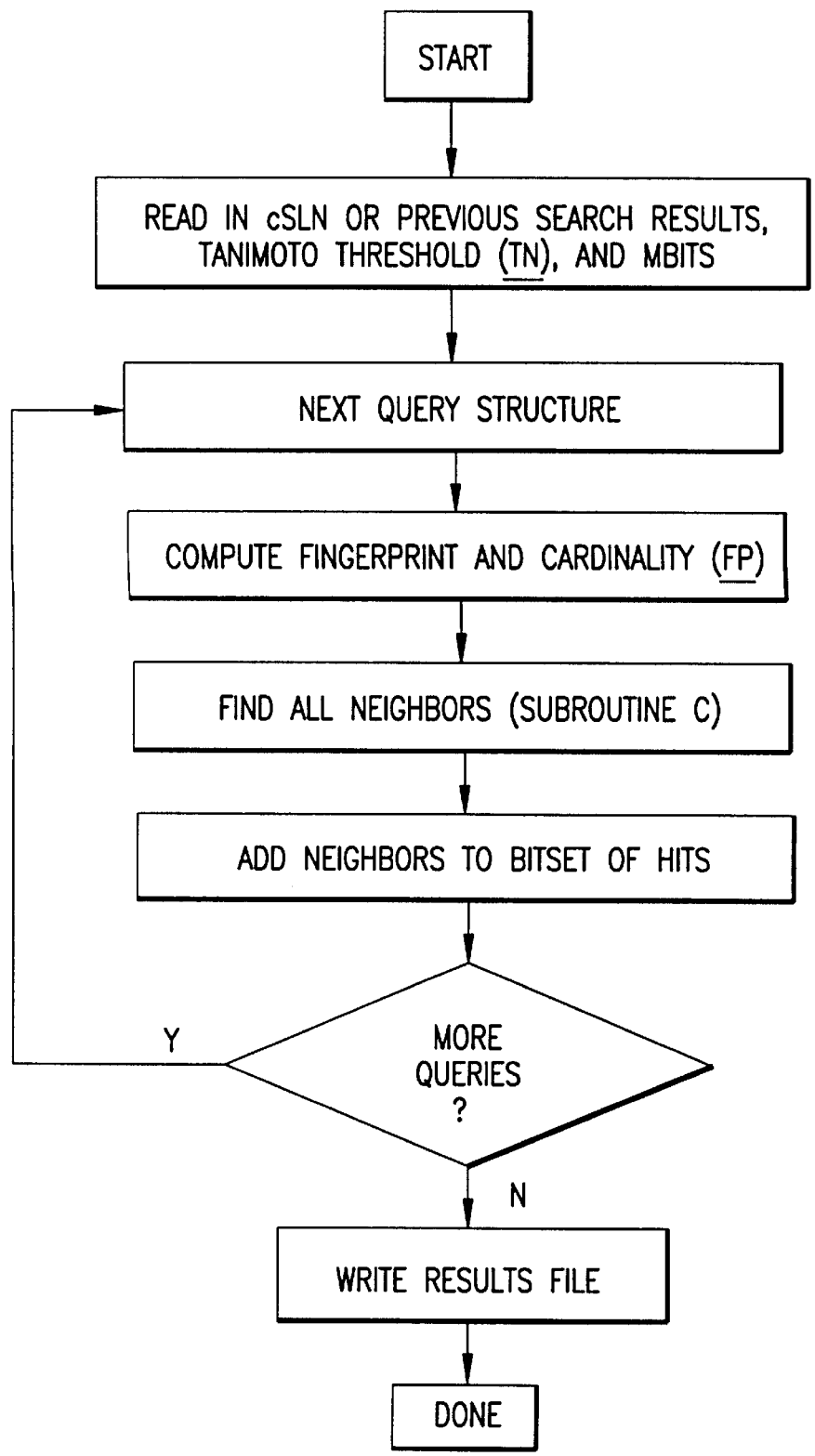
FIGS. 21, 22, and 23 are a flowchart summarizing the overall process of using the Tanimoto fingerprint metric to search for molecules.
Figure 22:
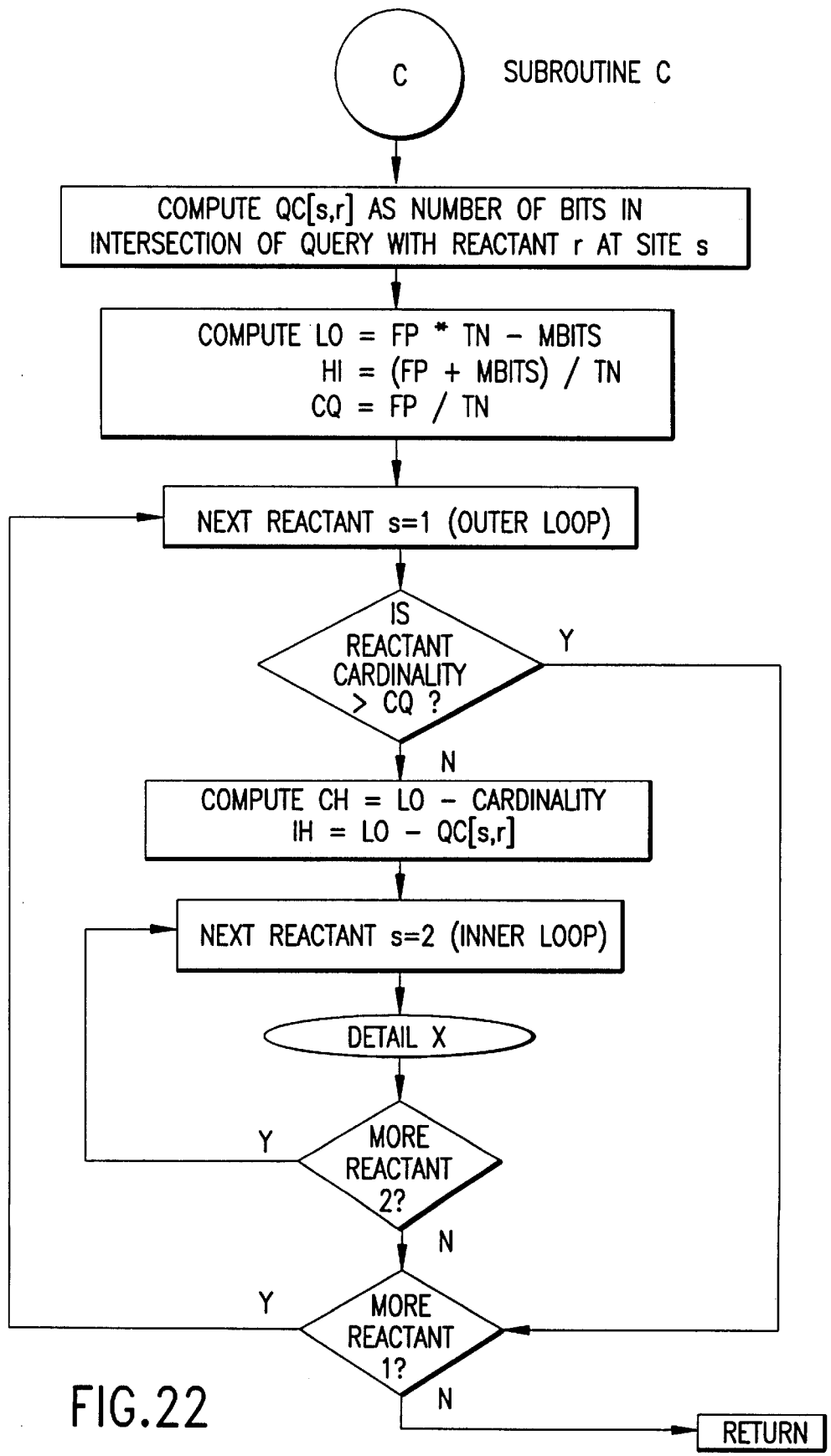
Figure 23:
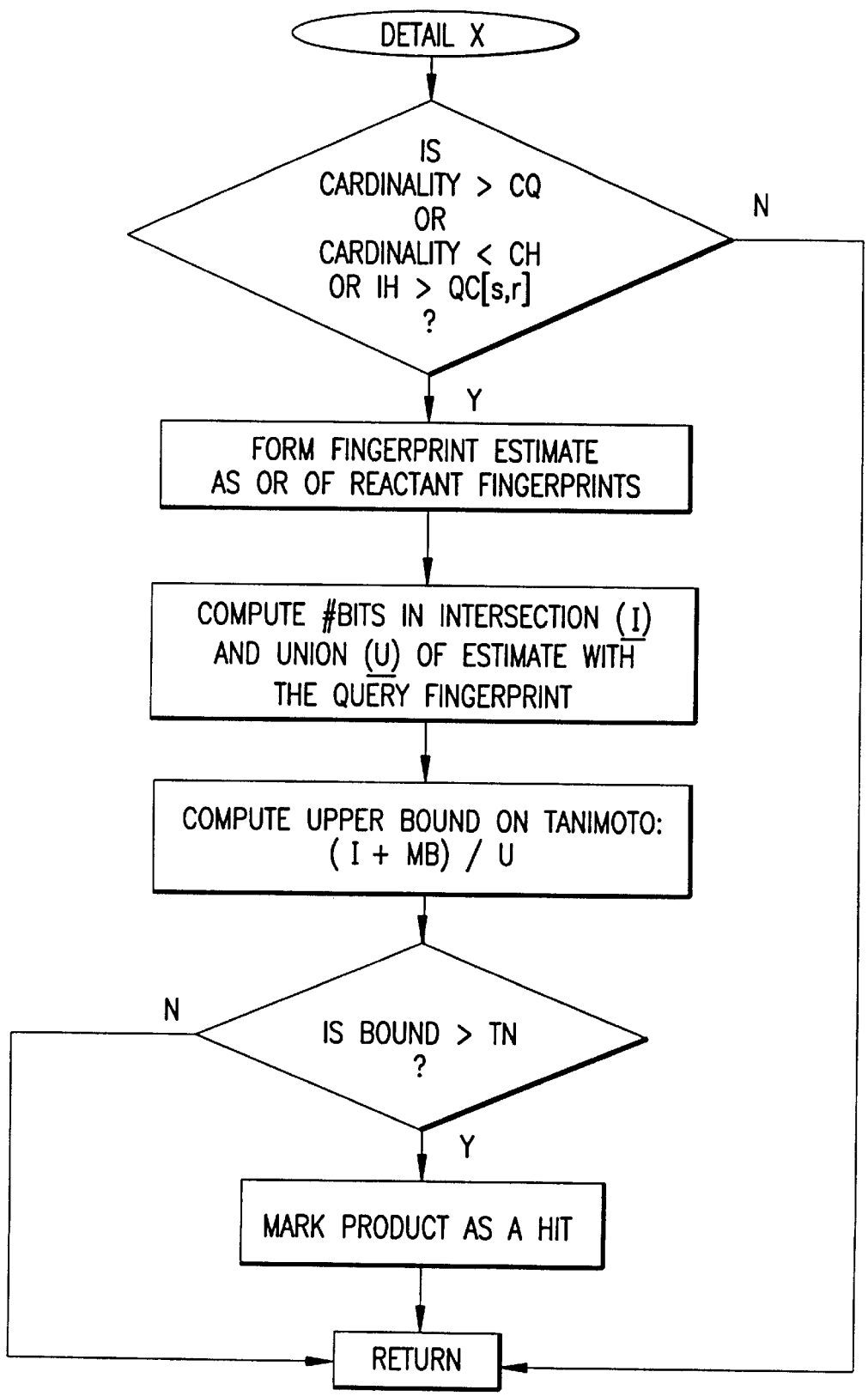

A brief overview of a typical search utilizing 2D fingerprints (a validated metric) will highlight the general approach used for all searches of the virtual library, which at their most fundamental level, rely on the values of the neighborhood distances found for the validated metrics. The overall process of using the Tanimoto fingerprint metric to search for molecules is summarized in the flowchart of FIGS. 21, 22, and 23. A typical library based on the combinatorial synthetic scheme utilizing a reactive diamino core will be used again as an example. As noted, this synthetic scheme alone contributes approximately 112 billion compounds to the virtual library data base. The question typically presented will ask whether the virtual library contains any molecules having a structure likely to yield a biological activity close to that of some known compound. To complete the search nothing need be known about the actual chemical compound for which close structures are desired, provided a 2D fingerprint for the molecule is supplied. Of course, generally, the molecular structure of the known molecule is provided and the software calculates the 2D fingerprint. A particularly important consideration is that the known molecule need not have resulted from a combinatorial synthesis and can, in fact, have any possible structure. The searching method of this invention independently searches each set of associated files generated by the virtual library construction method of the invention; in the case of the diamino example, a set of three files as outlined earlier. The reason each must be searched independently is that the searching program utilizes a knowledge of the number of sites (at which structural variations occurred in the synthetic scheme) to analyze the closeness of structure to the test molecule.

Based on knowledge of the neighborhood property of the validated Tanimoto metric, any molecule falling within a neighborhood Tanimoto similarity of 0.85 of another molecule should possess similar structural and biological characteristics. For this example, a Tanimoto similarity of 0.85 provides the basic selection criteria for examining the virtual library data base. Continuing with the example above, the fingerprint of the known molecule would first be compared to the fingerprint contained in every structural variation occurring at each of the two sites (2×15,000). The method determines how many of the bits set by the known molecule would be set by each structural variation. For all 15,000 choices at varying site $R_1$ (all 15,000 structural variations at $R_1$) the method compares the known molecule's fingerprints to the structural variation fingerprint. The same is then done for all 15,000 structural variations at site $R_2$. Then, for each one of the 15,000 choices at varying site $R_1$ the number of the matching bits set by that structural variation is added to the number of the matching bits for each one of the structural variations at $R_2$. For the entire set of structural variations at $R_1$ and $R_2$, this involves only the integer addition of 15,000× 15,000 terms and may be typically accomplished within fractions of a minute.

As each addition is completed, the resulting sum is compared to the Tanimoto neighborhood criteria. Suppose 100 bits were set by the known molecule. If the sum of bits totaled 65 and the neighborhood Tanimoto criteria of 0.85 (85 out of 100) were used, it would not be possible for any combination of those structural variations to form a molecule which would closely match the structure of the known molecule.

As noted above, the method also provides a check (MBITS) on the approximation routine used to calculate the fingerprints of the product molecules which would be formed from the two structural variations at sites $R_1$ and $R_2$. In this example, a typical MBITS value of 4 is assumed. Adding the 4 MBITS to the 65 only yields 69 which is clearly not within the required degree of Tanimoto neighborhood. However, had the bits from the structural variations added to 82, then the addition of the MBITS 4 would yield a total of 86, and the molecule formed from those structural variations would be considered close enough to check further. To confirm a match, the fingerprints from the two structural variations involved are OR-ed (Boolean) so that commonly set bits are counted only once and then compared to the fingerprint of the known molecule. Only if the resulting number when added to the MBITS term is greater than 85, is the product molecule represented by the two variations considered a match and included in a subset library resulting from the search. While these additional calculations take extra time, it is only necessary to perform them on structural variation combinations which pass the first level of screening (set bits>85). Therefore, typically only thousands of extra additions need to be calculated instead of millions, and the method is very fast. By the method of this invention hundreds of millions of possible compounds may be searched within a couple hours of computer time.

This testing procedure is continued through every set of structural variation virtual library files. Different sets of files resulting from other two site synthetic schemes would be checked in a similar fashion. When the known molecule was tested against a file set constructed from a synthetic scheme having three sites at which a structural variation could occur, the sum of the matching fingerprints contributed from three structural variations would be used and tested against the fingerprint of the known molecule in an identical manner. The actual method embodied in the software, performs many quick checks on each set of structural variation files and quickly ascertains whether that set of files could yield a product structure with the required structural characteristics (fingerprint in this example). If the quick check indicates that the set of files could not yield the known molecule, the search is quickly advanced to the next set of files. In fact, on a parallel processing machine, many simultaneous searches are performed. Thus, the time to search the entire virtual library is relative short.

Several points are extremely important. First, the characteristic of the known molecule is checked against only files associated with the structural variations. Thus, a set of associated files containing 2,000 structural variations (where 1,000 structural variations may occur at each of two sites) requires the examination of only 2,000 structural variations to accomplish a search of 1,000,000 (1,000×1,000) possible product molecules. Second, during the search only the structural variations which would contribute to a molecule having the desired structural characteristics are identified. Only after all such structural variations are identified, are the actual product molecules assembled from the structural variations and their entire structure specified for inclusion in the desired subset. Third, it does not matter whether the known molecule could be synthesized by a known combinatorial scheme. The information derived from a search such as in the example, would identify those molecules which could be derived from a combinatorial scheme which most likely have the same structural and biological characteristics as the known molecule. However, in creating the virtual library, all that is required is that the compounds can be described by a CSLN. The searching method of this invention, could equally well find one or more of these molecules not derived from a combinatorial synthetic scheme as being likely to have the same structural and biological characteristics of the known molecule. The only difference in this later case is that no information about a possible synthetic route is available from the results of the search.

Clearly, the greater the number of compounds specified in the entire virtual library data base whether based on known combinatorial synthetic schemes or resulting from other synthetic pathways and expressed as a CSLN, the greater the likelihood of finding molecules with similar structural and biological characteristics. Fourth, such structural searches require the use of validated metrics exhibiting a neighborhood property to characterize both the structural variations and the known molecule. Fifth, once the virtual library data base is constructed based on the method of this invention, there are any number of different types of searches which can be run. The software code provided with this application permits many such searches as outlined in the descriptions of the code below.

ii. Design Screening Libraries (Subsets of the Virtual Library)

In the current invention, one single method is used to select among all possible products from one or more reactions which share a common core substructure. A bitset is used to represent all the possible products (generally in the tens of millions). One may choose to limit the design subset selection to those compounds which are made of reagents from a specified subset of suppliers, to those of suitable price, to those of suitable molecular weight, logP, etc. One may seed the design with a set of preselected products. One may remove all products in the neighborhood of a subset of compounds as a preface to the design run.

The design process, once all the above initial subset operations have been performed, is extremely simple:

select a compound to add to the design, and remove its neighbors from further consideration continue until no other compounds are left The selection may be random, or may be directed to maximize use of a reagent once selected (this matches the practical requirements for a laboratory two-step synthesis in which maximum use of the first step's intermediate structures offers a substantial advantage in speed and cost). In principle, any rule can be invoked to prioritize which compound to select next, since any remaining compound is allowable at every step. Examples of this type of search are given below.

(a) Subset Screening Library Based on Topomeric Fields and Tanimoto

Figure 24:
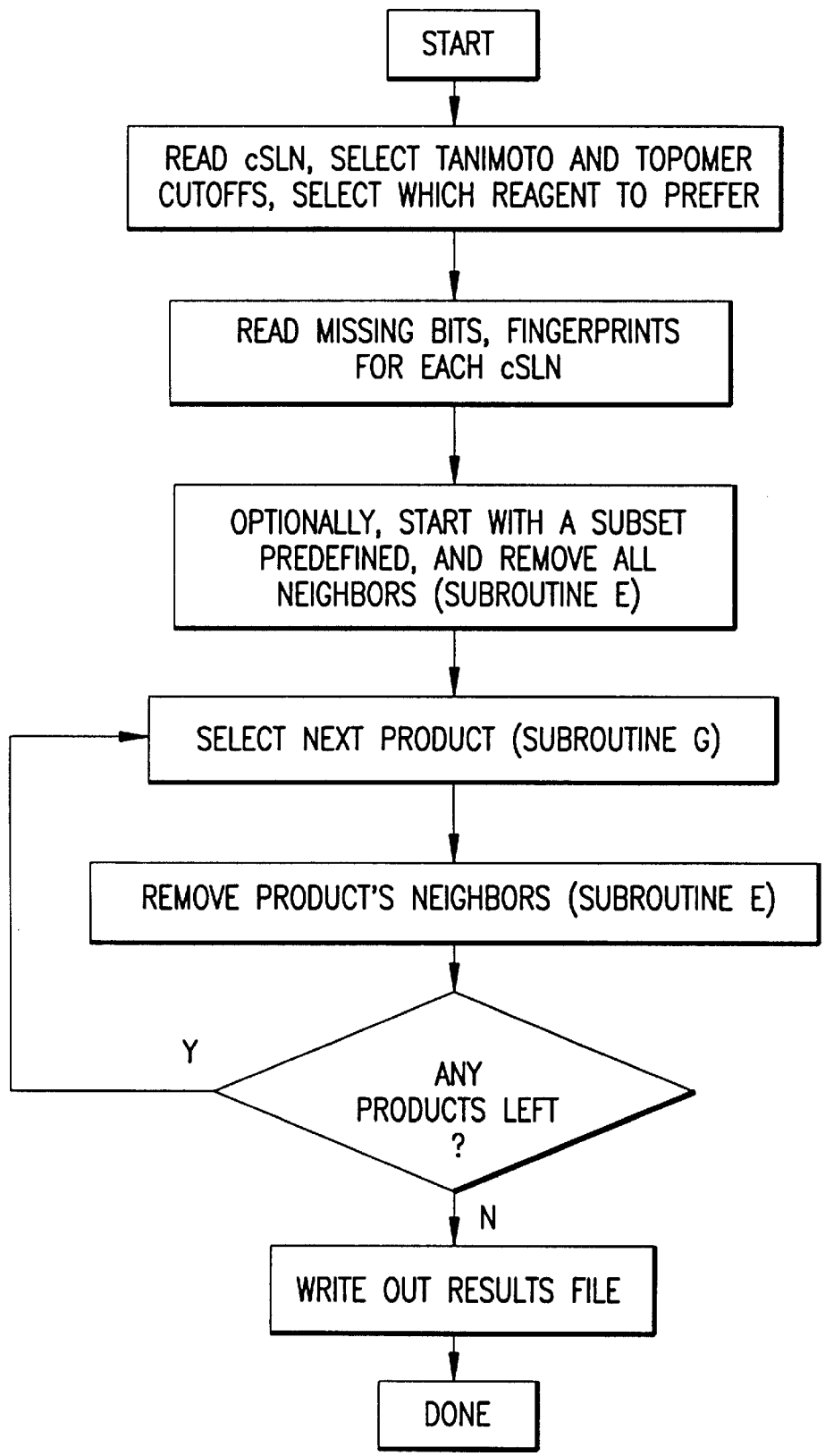
FIGS. 24, 25, and 26 are a flowchart summarizing the overall process of using both the topomeric CoMFA and Tanimoto metrics to search for molecules in the virtual library.
Figure 25:
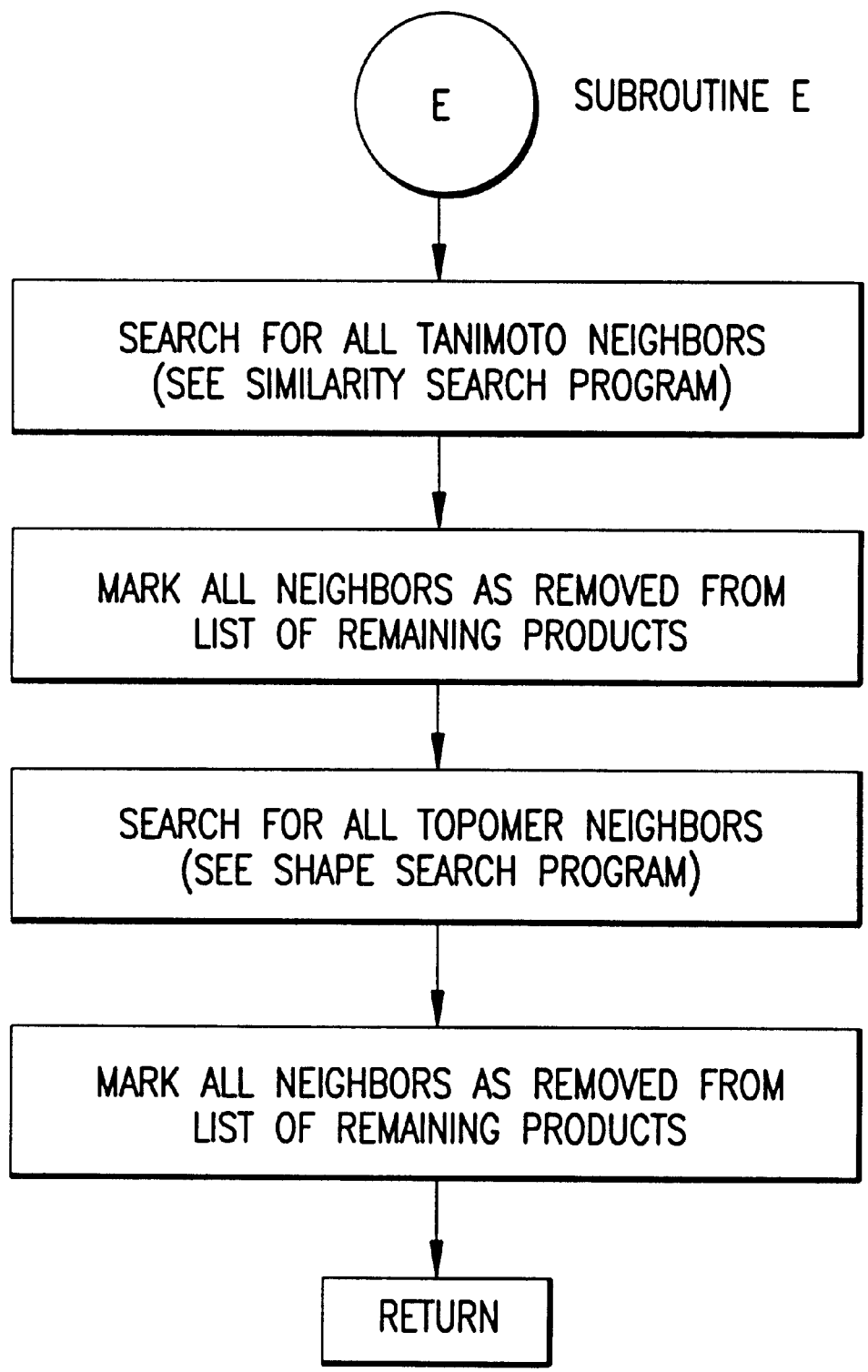
Figure 26:
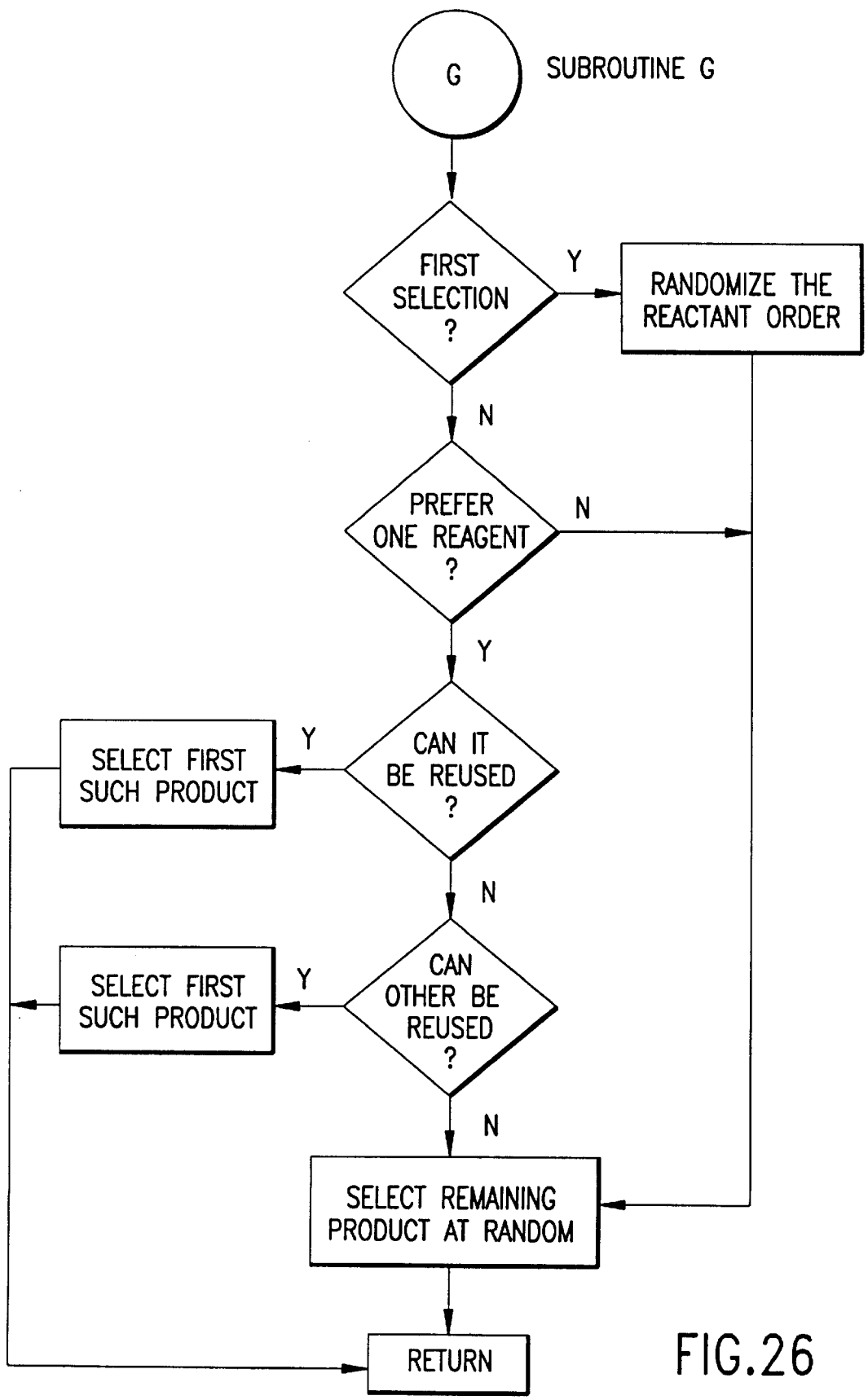
Figure 27:
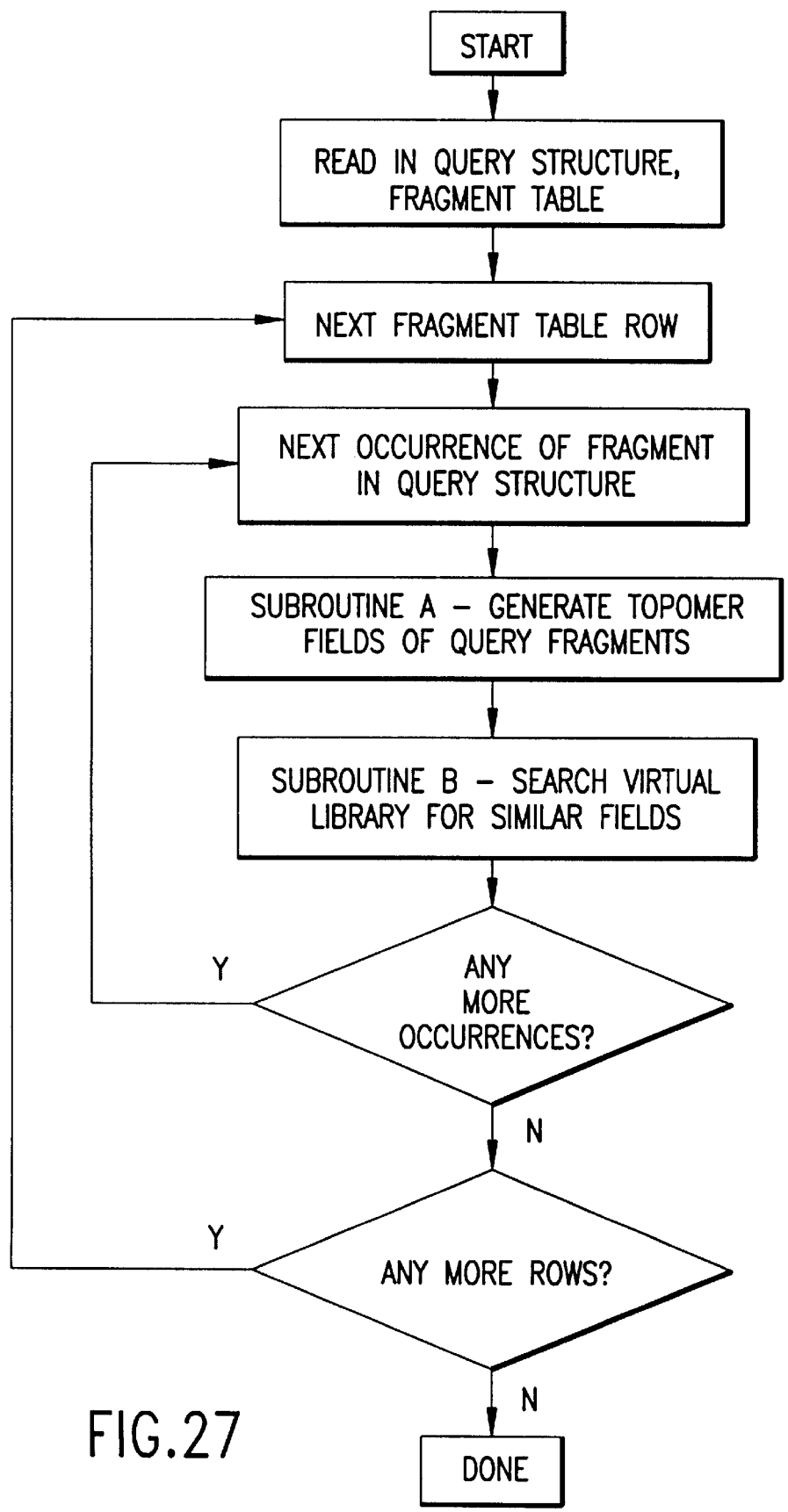
FIGS. 27, 28, 29, and 30 are a flowchart summarizing the overall process for topomeric searches of arbitrary query molecules.
Figure 28:
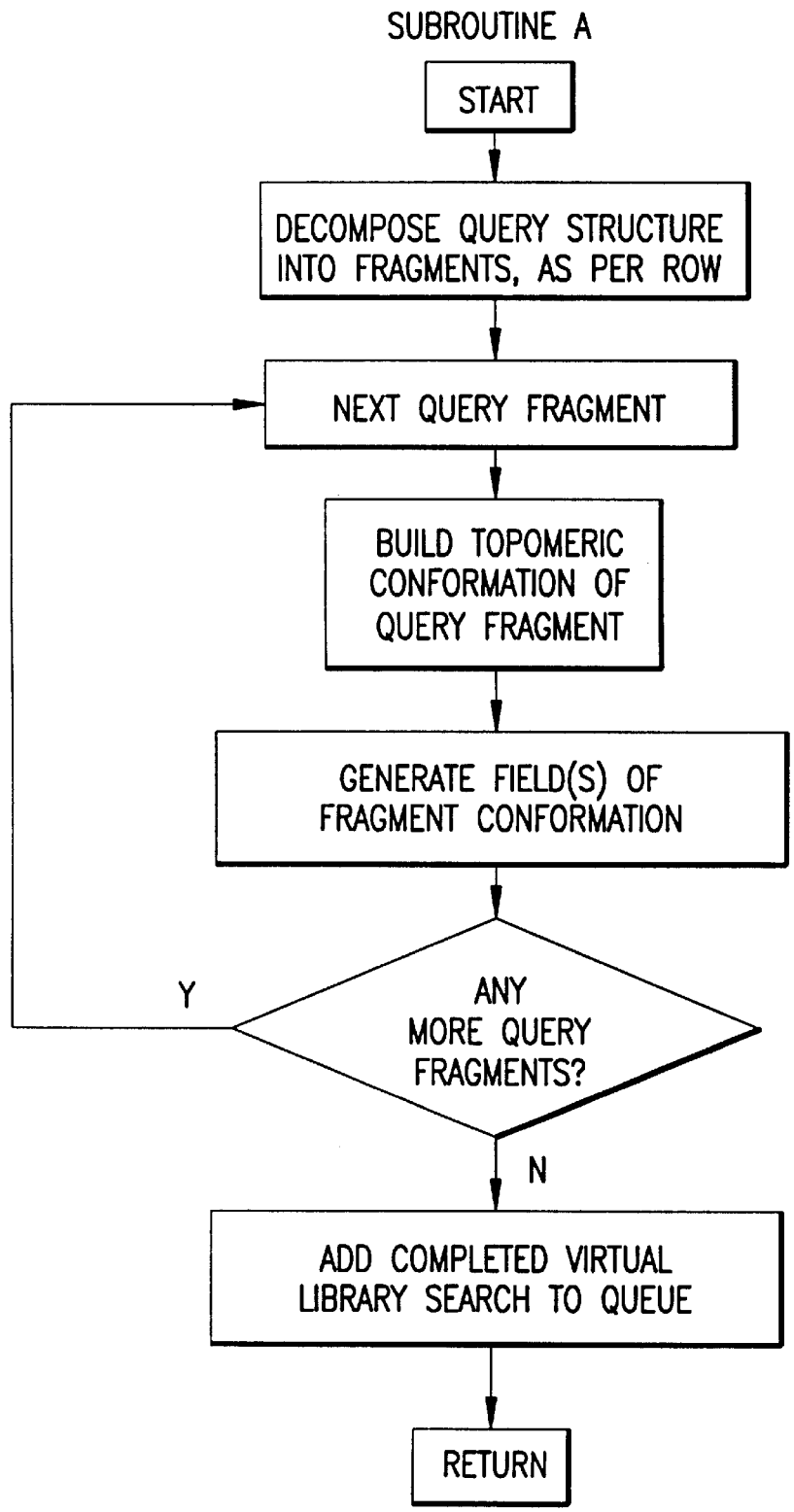
Figure 29:
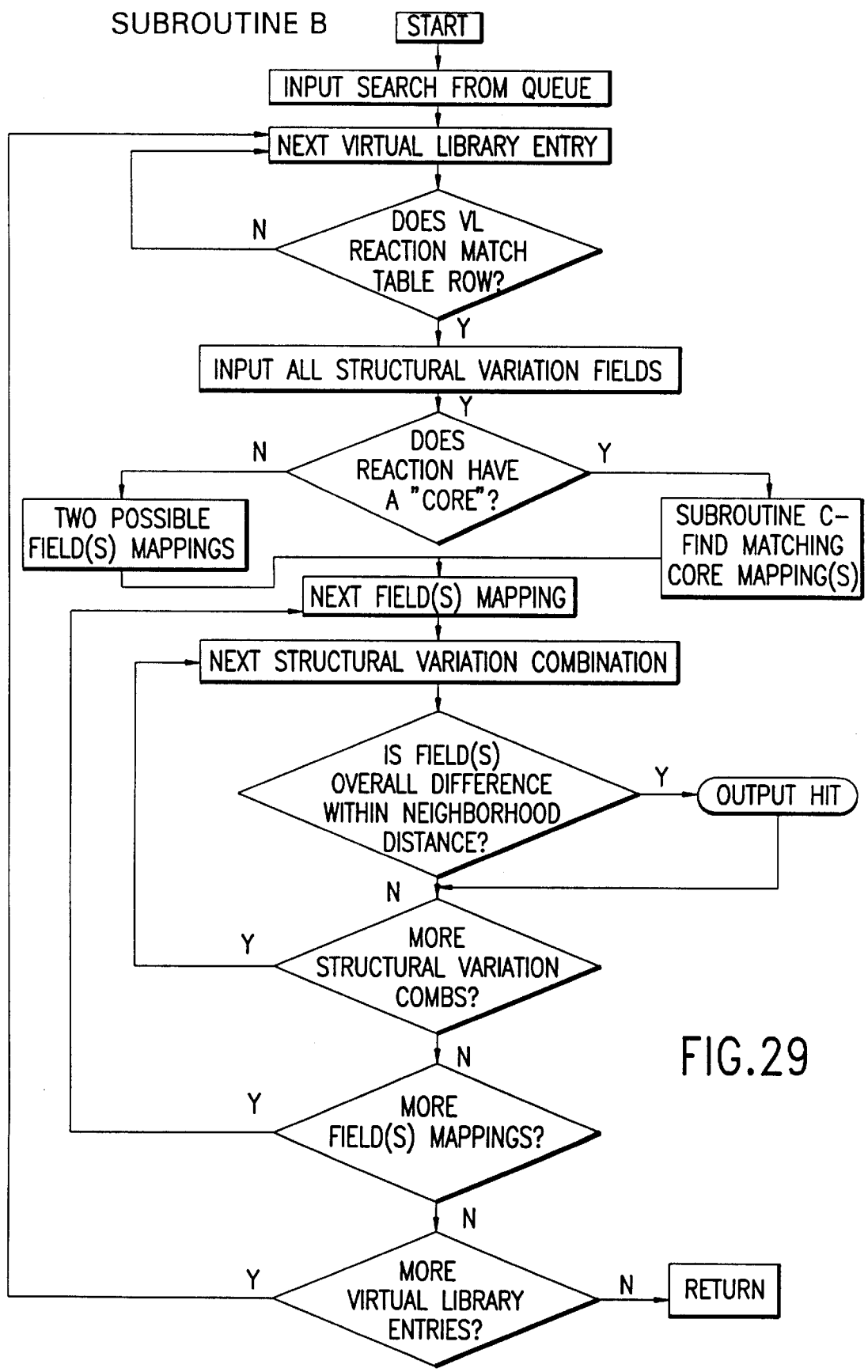
Figure 30:
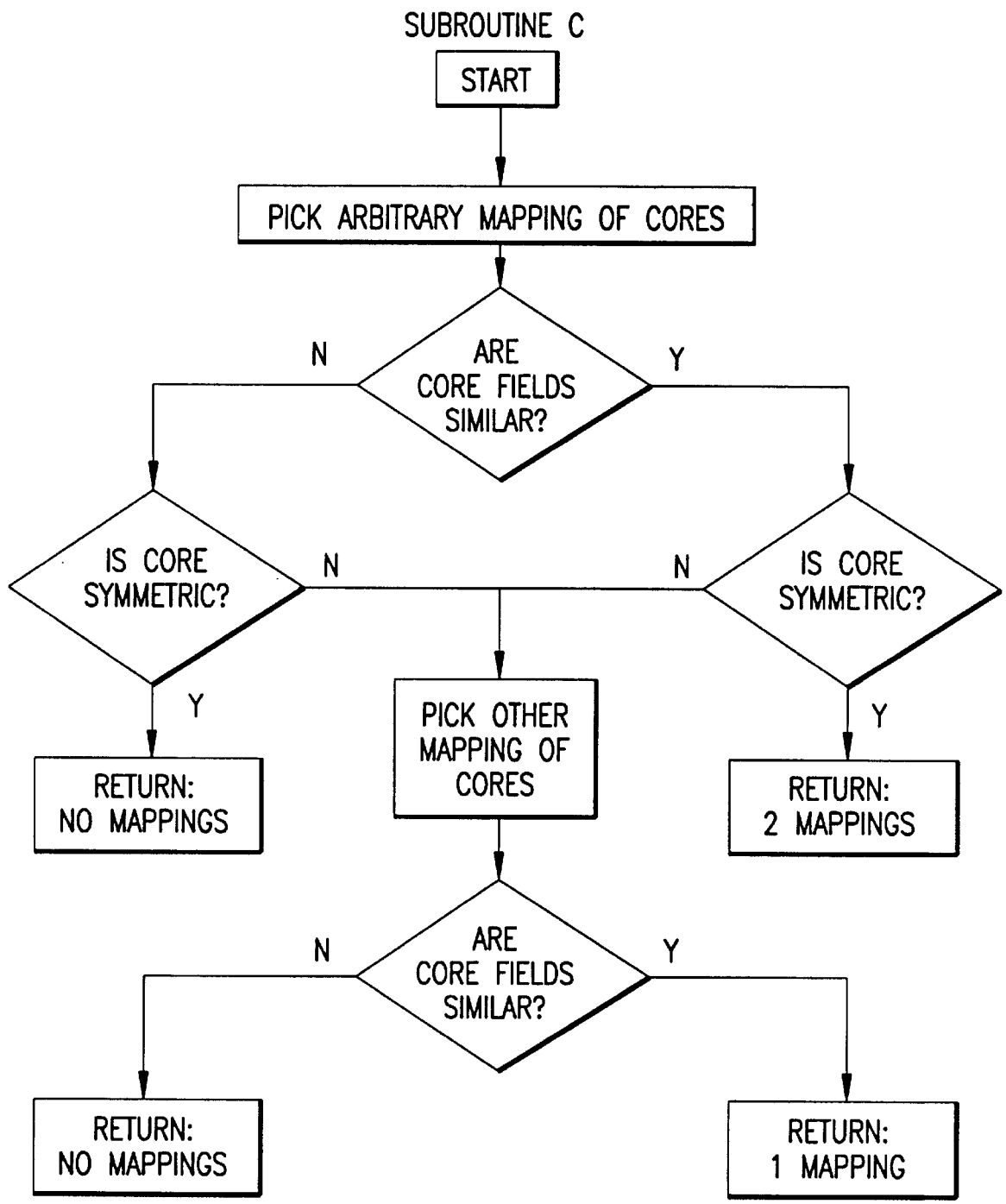

A selection of a screening library based on the same criteria as were discussed in the first part of this application is easily implemented using the virtual library. The library members are identified based on topomers (is the distance too small in topomer space) and on Tanimoto similarity separately, as was done in the earlier disclosed method. However, every reagent is always allowed, unlike the earlier method in which only a small subset of reagents made it through the reagent filter to the product stage. The earlier methods selected products based on maximal dissimilarity of product Tanimoto at each selection. Since by using the virtual library only the final selection set (all possible combinatorially created molecules meeting the selection criteria) is used, and does not depend upon or rely upon the ordering within a selected set (of reagents), the virtual library method is more flexible and in practice faster than the earlier disclosed method. In fact, since the product selection is not constrained by reagent stage selection, somewhat larger screening libraries result from using the virtual library. The overall process of using both the topomeric CoMFA and Tanimoto metrics to search for molecules in the virtual library is summarized in the flowchart of FIGS. 24, 25, and 26. Code to implement this search, db_des, is contained in Appendix K. A more extensive description of the code may be found in section G which follows.

(b) Subset Based on Tanimoto Similarity

A subset of the virtual library chosen just based on Tanimoto similarity/dissimilarity of product molecules, which could be created meeting some initial selection criteria, can be directly chosen. Code to implement this search, dbcslqs, is contained in Appendix I. A more extensive description of the code may be found in section G which follows.

(c) Subset Based on Topomeric Fields

A subset of the virtual library chosen just based on topomeric CoMFA field similarity/dissimilarity of product molecules, which could be created meeting some initial selection criteria, can be directly chosen. Code to implement this search, db_qstop, is contained in Appendix J. A more extensive description of the code may be found in section G which follows.

(d) Subset Based on Combined Metric

A subset of the virtual library may be based as well upon the combined topomeric-fingerprint metric described earlier. Code to implement this search, db_both, is contained in Appendix L. A more extensive description of the code may be found in section G which follows.

iii. Designing Lead Optimizations

The various techniques of lead optimization to explore the island of activity were discussed earlier. The same techniques used with the virtual library are much more powerful since a vastly larger chemical universe is being investigated. Generally, any property associated with a structural variation in the virtual library can be used to expand and define the product molecules sought.

Subsets of molecules from the virtual library database may be selected based on descriptors typically including, but not limited to, the following:

reagent identifier reagent supplier reagent or product molecular weight reagent or product price reagent or product estimated logP reagent shape contribution; product shape contribution under certain restrictions reagent or product 2D fingerprint product substructural features Subsets may be selected by applying by the following methods, including, but not limited to, simple filters, by requiring that filters meet a specific degree of similarity to reference compounds, or by applying proprietary design tools.

Specifically, the initial modes of subset selection may include:

- substructural searching, to identify compounds which have a set of required structural features, is perhaps the most often used method of chemical database subset selection
- 3D feature searching, to add interatomic distance requirements to the substructural searching, is also familiar to experts in chemical database searching
- similarity searching, to find subsets which are substantially like a reference compound, is widely used as well and corresponds to application of a neighborhood principle applied to 2D fingerprints or—planned extensions—atom pair distance fingerprints, etc.
- scalar searches corresponding to traditional nonstructural database queries, to find compounds with for example logP between 5 and 8 and molecular weight under 500 and price above 750.
- maximum dissimilarity queries, which are used primarily to order a large subset of compounds such that as one reads down the ordered list, compounds are less distinct from each other as a group
- STIGMATA (a procedure popularized by the scientists at Parke Davis) queries, in which compounds are selected based on the presence of specific bits in a fingerprint (2D, atom pair, pharmacophore triplets, etc.). Commonly such a query is derived by reference to a set of desirable compounds, from which the bits present in all compounds in the set are derived.
- design queries (scalar, topomer, fingerprint, arbitrary weightings of any of these) of either of two types:
  - gridding methods, in which the objective is to have one compound within each specific "hypercube" of the design space
  - neighborhood methods, in which the objective is to obtain a set in which no two compounds are overly similar, and in which no "holes" exist needlessly (a) Search Based on Tanimoto Similarity Details of a typical lead optimization using the Tanimoto metric were highlighted under section 12(E)(i) above. Essentially, what is sought is a list of all compounds to be found within the Tanimoto neighborhood of the lead. Code to implement this type of search, db_sim, is contained in Appendix H. A more extensive description of the code may be found in section G which follows.

(b) Searches Based on Topomer Similarity

The notion of topomer similarity of a pair of molecules is well defined if the molecules have some common "core". An enhanced method has also been discovered which allows arbitrary structures as search queries not just those which result from a combinatorial synthesis. Therefore, to find molecules similar to some target within the virtual library, the following three phase operation as summarized in the flowchart of FIGS. 27, 28, 29, and 30 must be performed:

1) Determine which of the "common core" substructures (where the core may consist of a single bond and any single bond is equivalent to any other single bond for topomer searching) within the virtual library are wholly contained within the search target molecule. This can be done by any standard searching program, such as Tripos' Unity package.
2) For each of the common cores found, remove that common core from the search target. The atoms remaining will comprise one or more side chains. Generate the topomeric conformations of each of the side chains, using the same code that is used to build topomeric conformations during library ("all possible products") generation. Generate the topomeric conformation of the core.
3) Using these topomeric conformations of each of the target molecule's side chains, search the combinatorial libraries corresponding to the previously identified common cores for all side chains whose sum of corresponding side chain topomeric differences is less than the neighborhood radius within the typical neighborhood range of 80–100 kcal/mol. (91 kcal/mol.) Alternatively, the root sum of square differences between the fields may be used to determine the selection criteria. The procedure is shown in the flowsheet of FIGS. 27, 28, 29, and 30 and described below.

(c) Topomeric (3D) Searching of Arbitrary Molecular Structures

In addition to searching the virtual library as outlined above, it is possible to conduct searches which were heretofore impossible by any means. In particular, a critical question which frequently occurs in chemical research, and especially in biological research, can now be addressed by the discovery and creation embodied in the virtual library. The problem, as it is usually presented, takes the form: given an arbitrary query molecule (generally one previously found to exhibit a desired activity), find biologically similar molecules, that is molecules of similar 3D shape and activity, that can readily be made and tested. Generally, such a query molecule will not have resulted from a combinatorial synthesis, and, in fact, no knowledge of a possible synthetic route to the molecule may be available. As an example, suppose that compounds similar in 3D shape to but structurally different from the structure (written in SLN) CH3C(=O)NHCH(CH3)CH2NHCH2CH2OH are desirable, perhaps because this hypothetical structure was reported to be highly active in a competitive pharmaceutical preparation.

As described earlier, the topomeric 3D shape data within the Virtual Libraries actually describe fragments (structural variations) of molecules. To find similarly shaped molecules within the virtual library, the query molecule must be fragmented and the shapes of its fragments compared with the shapes of corresponding fragments (structural variations) in the virtual library. The difficulty is that a query molecule can be fragmented in so very many ways for searching against the virtual library containing in excess of 10^12 molecules. (The example given has nine bonds connecting heavy atoms, so there are nine two-fragment combinations that could be considered, 9×8=72 three-fragment combinations, 9×8×7=504 four-fragment combinations, etc.) Given this situation, what is needed is a way to emphasize those fragmentations that are most likely to conform to efficient synthetic routes from available starting materials, without requiring the searcher of the virtual library to have any knowledge of what synthetic routes it includes.

The solution to this problem which can be uniquely achieved with the virtual library is a "fragmentation table", where each row constitutes a rule of the following sort: "for each occurrence of this particular structural feature combination (structural variation) in the query molecule, decompose the query molecule in a particular way specified in terms of this structural feature, and search only those combinatorial libraries that utilize specified reactions (sequences) and/or building blocks, mapping specified query fragments onto specified classes of building blocks". Each such query decomposition found generates a search of the virtual library, returning all those products whose sum of squares of differences in shape between corresponding product and query fragments is less than a user specified neighborhood distance threshold. Passing the query molecule (by means of a suitable computer program) against all the rows of this table generates all searches.

To illustrate this approach with a simple example, one row in the table might have as its structural feature C(=O)—[!r]NH (amide bond, where [!r] states that the preceding bond must not be cyclic). This row would specify cleavage between the N and C of any matching fragment within the query, for our example query yielding the fragments CH3C(=O)— and —NHCH(CH3)CH2NHCH2CH2OH, and the characteristics that a matching subset library should have (primary or secondary amine reacting with an acid, acid chloride, isocyanate, chloroformate). The similarity searching engine then returns all products in the virtual library formed from amines close enough in shape to —NHCH(CH3)CH2NHCH2CH2OH and acylating reagents close enough in shape to CH3C(=O)—.

Note that the amide bond is a synthetic convenience, not an absolute arbiter of shape similarity. Molecules in which the amide bond is "reversed" might also be sufficiently shape similar overall to have biological similarity to the query molecule, despite the local differences in shape resulting from the NH to C=O mismatch. Indeed, any reaction that forms a single acyclic bond might contain bioisosteres of our query molecule within its virtual library. On the other hand, an amide library would contain both the most accessible and also the largest number of bioisosteres and so this is the library that should first be searched.

Another row in the fragmentation table might designate a query decomposition into three fragments, with a structural feature R—[!r]NXN—[!r]R. Application of this row to our query molecule would generate CH3C(=O)—, —NHCH(CH3)CH2NH—, and —CH2CH2OH. When searching the "diamine" library (about 10^11 structures) for similarity using these fragments, the "core" or diamine component is searched first for fragments similar in shape to —NHCH(CH3)CH2NH— (see below for a description of the special features of core shape similarity). Core shape similarity is much rarer than side-chain shape similarity and so an efficient search process considers core similarity before considering side chain similarity.

An example of what a few rows in a typical fragmentation table look like is shown below. The description of the individual named columns are as follows:

CLASS_ID=equivalent in meaning and value to CLASS_ID in the REACTIONS table. Identifies a particular reaction sequence as it would be carried out in the laboratory. Only those virtual library records whose CLASS_ID matches this value will actually be searched.

PRIORITY=Allows a searcher to control the depth of a search. Lower values correspond to reactions which are less general, but whose products are more likely to resemble a matching query. Deeper searches will also consider rows having higher values of PRIORITY.

SLN=the structural pattern that will be matched within the query molecule. Each match found within the query molecule generates a decomposition of the query into fragments for topomeric similarity searching, as detailed elsewhere.

REACTANTS=Allows the developer of this table to limit application of a particular row to reactions involving particular classes of reactants.

ATOMS=Specifies, by reference to the fragment description with the SLN column, the bonds in the query whose breaking will generate the fragments to be used in topomeric field similarity searching.

The three rows shown illustrate the three examples discussed elsewhere in this description: Row 1—diamine derivatization; Row 3—amide formation; Row 7—thioether cleavage. For clarity the information for these rows is broken into three sections:

| | 1<br>CLASS_ID | 2<br>PRIORITY | 3<br>SLN |
|---|---|---|---|
| ROW1 | 5 | 2.00 | Hev-[!R]NXN-[!R]Hev |
| ROW3 | 6 | 2.00 | HevHev(=O)-[!R]NHev |
| ROW7 | 22 | 2.00 | CS-[!R]HevHev |

| | 4<br>REACTANTS |
|---|---|
| ROW1 | X1=RN=C=O,ClC(=O)OR,Epoxide,Ald/Ket,RC(=O)Cl,<br>RCOOH,RCOO[-],RSO2Cl,ArF(activated),N:CHal,C=CCX,H<br>X2=RN=C=O,ClC(=O)OR,Epoxide,Ald/Ket,RC(=O)Cl,<br>RCOOH,RCOO[-],RSO2Cl,ArF(activated),N:CHal,C=CCX,H |
| ROW3 | X1=Amine(~3) X2=RCOOH,RN=C=O,ClC(=O)OR,<br>RC(=O)Cl,RCOO[-],RSO2Cl,ArF(activated),N:CHal,C=CCX |
| ROW7 | X1=RSH X2=RN=C=S,RN=C=O,RSO2Cl,RCl,<br>ArF(activated),N:CHal,RBr |

| | 5<br>ATOMS |
|---|---|
| 1 ROW1 | 1,2 5,4 |
| 3 ROW3 | 4,2 2,4 |
| 7 ROW7 | 2,3 3,2 |

The power and utility of topomeric steric field analysis of fragmented structures is highlighted by a recent analysis of the structures of Tagamet and Zantac (H2 antagonists). Tagamet and Zantac were each fragmented according to Row 7 of the fragmentation table and the topomeric steric fields calculated. The metric distance (difference in metric values) for the two compounds was 127.

Figure 31:
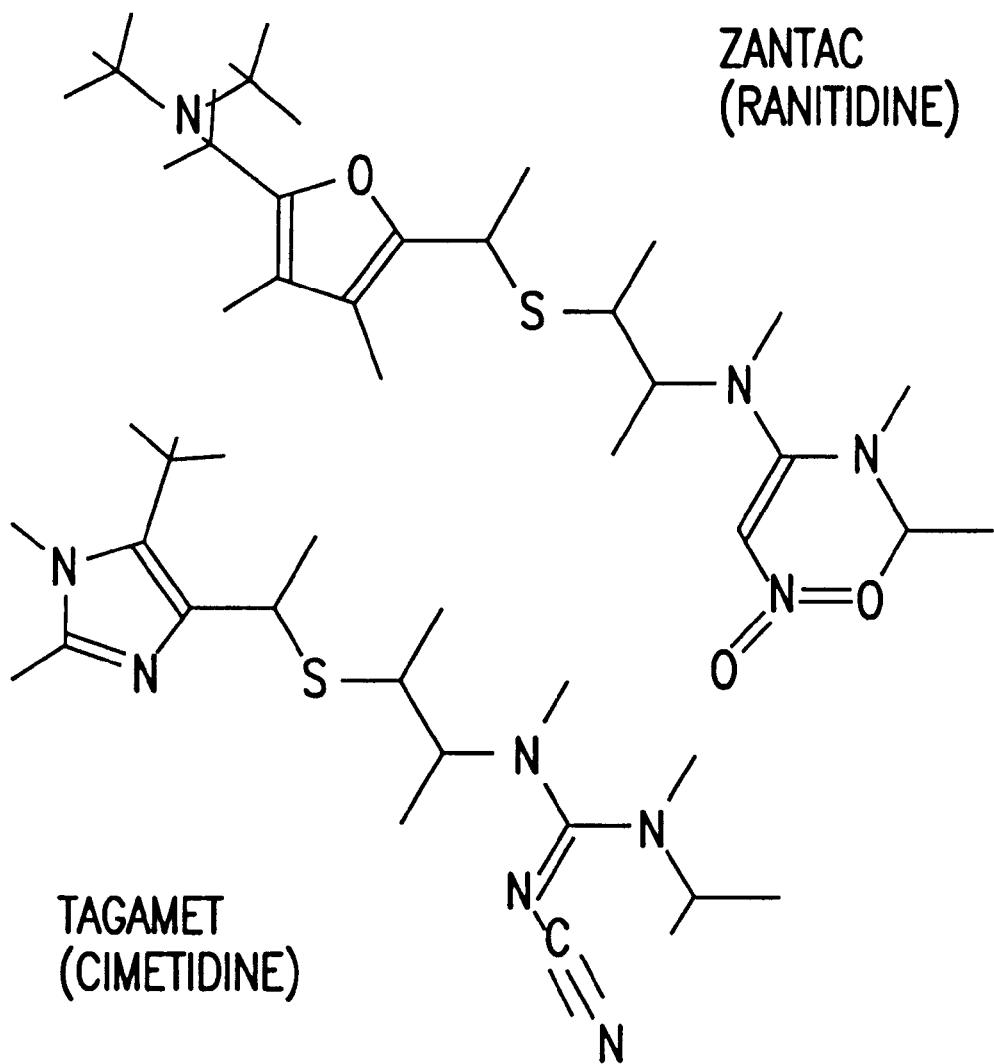
FIG. 31 shows the topomeric conformations of TAGAMET(cinctidine) and ZANTAC(ranitidine).

Remembering that a range of 80–100 defines a neighborhood distance for an approximate log2 biological difference for the topomeric CoMFA descriptor, the value of 127 strongly suggests that Tagamet and Zantac should have similar biological activities. Such knowledge would have been very useful to those either seeking to protect molecules with similar structure/activity to the known molecule or to those seeking to find molecules which look similar to the receptor but which are not entirely structurally identical to the known molecule. It should be noted that other widely used diversity approaches, 2D fingerprints and pharmacophoric patterns show a remarkable lack of similarity between the drugs. Indeed, in the topomeric configuration generated by the methods of this invention, Tagamet and Zantac look very similar even to the unaided eye as shown in FIG. 31.

(d) Topomeric (3D) Searching of Core Structures

An ancillary problem when attempting to find molecules in the virtual library (constructed principally from combinatorial chemistries) which are structurally and biologically similar to a given query molecule, is the treatment of the central core to which structural variations can be attached. The virtual library defines the shape similarity of two molecules as the sum of the similarities of comparable fragments. "Core" fragments are any fragments that have multiple attachment bonds to other fragments, in contrast to "side chain" fragments which have only one attachment bond.

Overall molecular shape will be affected most by the relative positions of core attachment bonds. Consider the three possible bivalent phenyl cores, ortho, meta, and para. These will be quite similar in their intrinsic shapes—only a hydrogen changes place—but the molecules derived from the three cores will be very different in shape if the side chains are at all bulky. Therefore in considering the shape similarities of cores the relative positions of attachment bonds must be weighted far more heavily than the shape differences themselves.

The prior art has attempted to deal with this problem. Lauri and Bartlett[17] have described CAVEAT, which in the nomenclature of this disclosure would be considered a "core similarity" searching system that considers only relative attachment bonds, not shape, of all theoretically constructible cyclic cores. In their work, the relative geometry of two attachment bonds is expressed in terms of their distance, angle, and torsions. In contrast the present inventors have found that a much more self-consistent shape classification of, for example, all 750 commercially offered diamines, is obtained when one of the attachment bonds is aligned on the X-axis (as in the standard topomer conformation, described earlier) and the differences calculated as the root mean square of summed differences in the x, y, and z coordinates of the two ends of the other attachment bond. (The conformation used in this procedure is the topomeric conformation of the core with a methyl group replacing the more distant attachment bond.) This procedure differentiates cyclic from acyclic fragments much more strongly than it differs among the linear acyclic moieties pentylyl, hexylyl, and heptylyl.

In addition to this RMS difference in x, y, and z, the differences in steric (and any other fields) also contribute to the bioisosteric differences between two cores. Because there are potentially two or more possible attachment bonds in a core, there are two or more ways in which two or more cores may be compared. So the difference in fields is taken as the least of these possible differences. The combination of two descriptors in considering the difference between two core structures, the attachment bond differences and the field differences, introduces a relative weighting concern. In practice it has been found in clustering experiments like those described for the thiols that the internally most self-consistent classification of 750 diamines results from numerically equal weighting of the two RMS differences.

Thus, the successful generation of a topomeric descriptor for cores involves two advances. In comparison with the procedure for side chains, the relative position of attachment points has been introduced, for example, to distinguish ortho phenylene from para phenylene. In comparison with the treatment of attachment points previously described by Bartlett et al., the use of differences in x,y,z coordinates, rather than relative geometries such as distances and solid angles, provides a stronger differentiation needed between, for example, cyclic and acyclic cores.

G. Code Attachments

The following software code comprising the main sections of the invention is described below and is attached in the Appendices. In addition, necessary auxiliary code is also set forth in the Appendices. All together, all code necessary to fully disclose an enabling embodiment of the invention in the computational chemistry environment specified earlier is set forth in the several appendices. In some cases new code is provided which differs from that in the priority documents to include enhancements described in the text. In particular, as the virtual library has been expanded, it has been found that the larger number of compounds identified from the searches is more conveniently handled which can deal with bitsets rather than as ASCII text. The additional auxiliary code required to manipulate the bitsets is contained in Appendix R. However, the use of bitsets is a computation convenience and does not involve any change in the construction or searching of the virtual library.

Appendix A

One section of the code in this Appendix generates topomeric conformations, and another section generates the best slope line for Patterson plots.

Appendix B: This code calculates the hydrogen bond variation to be applied to the CoMFA steric field.

Appendix E: getacd.core This code handles the first phase of the construction of the virtual library.

Appendix F: SYB_MGEN_GPLS_COMFA_HEX *** CTOPS This code calculates the topomeric CoMFA field of each structural variation and adds it to the structural variation files. It also allows the computation and use of other than just steric fields. This Sybyl expression generator, written in C, in invoked from SPL by a call %comfa_hex (Row Column). It returns an ASCII hexadecimal representation (0–9,a–f) for each CoMFA grid point in row "Row" and CoMFA column "Column" in the string which is seen as CTOPS in the input files.

The encoding is as shown in the subroutine lookup_my_comfa_code( ). As indicated, a missing value is assigned "0" and all legitimate values are assigned a number according to their numerical value. The binning is not quite linear; since the COMFA values are infrequently between 10 and 30 this was empirically found to reproduce the exact CoMFA distances very well. The distances arising from this CTOPS description were validated against data sets to confirm that the encoding and decoding introduced no significant round-off problems. The distance corresponding to the coded topomer field values of CTOPS are seen in the dbcsln_des routine called WhatsTheDifference( ).

Appendix G: dbcslnprepro

This program takes the description of the common core and solicits for each substituted position the SLN for the extended core. From this, and the list of structural variations, it computes the fingerprint and the fingerprint's cardinality for each structural variation and appends this as the fpcard and fp fields.

Additionally, the program creates a specified fraction of product compounds and computes their fingerprints exactly. The actual product fingerprint is compared to the fingerprint estimated from the pieces, and any discrepancy is noted by counting how many tested products have 0 missing bits, how many have 1, etc. The largest observed value is used as the MBITS parameter for the reaction. The new version of this code performs the same functions as the original code except that it writes separate files for fpcard and fp. In addition, it forms a master file to keep track of the association of all the files.

Appendix H: dbcslnsim

This program takes one or more SLN structures as queries, along with the MBITS and the desired Tanimoto similarity, and the output of the dbcslnprepro run. It produces a listing of all products which may be above the Tanimoto cutoff value, by listing the index of each structural variation and both the apparent Tanimoto and the maximum possible Tanimoto (it is the maximum possible Tanimoto which defines the results). This code now reads master files and can read bitsets output from other files.

Appendix I: dbcslnQS

This program takes the results of the dbcslnprepro program, along with the MBITS and the Tanimoto similarity neighborhood, to select a designed subset based on Tanimoto similarity alone. Additional options allow one to remove from consideration products with a parameter outside of the desired range (such as molecular weight or logP or price), and to remove all products whose enumerated fields for one or more reagents are not in a list of acceptable choices (such as supplier).

The design selection consists of first removing products from consideration based on range of variables or acceptability of reagent. An initial selection is made, normally by random selection among all remaining products. Every product whose maximum possible Tanimoto similarity is above the cutoff is removed from further consideration. A product is then selected from among all remaining products, either randomly or by rule to continue using one of the reagents (R1, R2, etc) so long as possible (so long as any product remains using that reagent). This selected product's neighbors are removed from further consideration also, and this simple loop continues until no products remain or a maximum specified number of selections have been made. The loop is simply: select, remove neighbors in Tanimoto space.

Appendix J: dbclsn_qstop

This program takes the results of the dbcslnprepro program, along with a value to define the topomeric similarity neighborhood, to select a designed subset based on topomeric similarity alone.

This program operates exactly like dbcslnQS, except that the step at which neighbors are removed is based on topomeric similarity based on the CTOPS fields of the reagents, rather than the estimate of Tanimoto similarity. Thus after a selection it scans all remaining products to find every one which has a distance within the similarity radius, and marks these neighbors as unavailable for further consideration.

(Note that this is equivalent to doing a topomeric similarity search for each selection. The results are not returned to the user, since their use is to make potential selections disappear!)

Appendix K: dbcsln_des

This program takes the results of the dbcslnprepro program, along with the MBITS and the Tanimoto similarity neighborhood, plus a value to define the topomeric similarity neighborhood to select a designed subset based on Tanimoto similarity and topomeric similarity acting independently. This corresponds closely to the method of designed subset selection in the earlier described method. This code now reads and writes master files and bitsets.

This program operates exactly like dbcslnQS, except that in addition to removing every Tanimoto neighbor of the selected compound, we also remove the topomeric neighbors. Thus after a selection it scans all remaining products to find every one which has a distance within the Tanimoto range, removes them, scans all remaining products to find every one which has a distance within the topomer range, and removes them.

This is equivalent to doing the dbcslnQS and dbclsn_qstop one after another in the innermost loop where neighbors are identified and removed. By setting either the Tanimoto or topomer neighborhood radius to be zero, one should be able to achieve the same results as dbclsn_qstop or dbcslnQS in fact.

Appendix L: dbcsln_both

This program takes the results of the dbcslnprepro program, along with the MBITS and a way to scale topomeric distance, plus a similarity cutoff for the combined descriptor of topomer and Tanimoto, to select a designed subset based on Tanimoto similarity and topomeric similarity acting as one combined descriptor.

This program operates exactly like dbcslnQS, except that the removal of neighbors is not based on either Tanimoto or topomeric distance by itself.

This utilizes the new, combined descriptor described earlier. It is not directly equivalent to either dbcslnQS or dbclsn_qstop in this sense. This code now reads and writes master files and bitsets.

Appendix M: dbcslntohits

This program takes the index results of dbcslnQS, dbclsn_qstop, dbcsln_both, dbcsln_des, or dbcslnsim and generates a full product structure SLN hitlist for them. This hitlist of products is suitable for treatment just as any set of chemical compounds—it loses its combinatorial identity as it becomes an assembly of independent chemicals. The new version of this code can now work with bitsets.

Appendix N: CODATA

This is a header file to declare variables.

Appendix O: DB_UTL

This code is a set of subroutines used in many places, and, in particular, by the design programs.

Appendix P: ELIMATE

This code is a set of subroutines used in many places, and, in particular, by the design programs.

Appendix Q: FILTER

This code contains subroutines for filtering undesired characteristics from product molecules.

Appendix R: dbcsln_bitset

This code provides the additional routines need and called by the other code to handle bitsets.

Appendix S: topsim

This code performs a topomeric CoMFA search for molecules similar to a query compound.

Appendix T: topsetup.core

This code performs the fragmentation required to implement a topomeric search of a query molecule not necessarily derived from a combinatorial synthesis.

From the proceeding description of the construction, generation, and searching of a virtual library, it should be clear that there are many variations which may be employed and, having taught how to generate and search one specific embodiment, all equivalent embodiments are considered within the scope of this disclosure.

While the preceding written description is provided as an aid in understanding, it should be understood that the source code listings appended to this application constitute a complete disclosure of the best mode currently known to the inventors of the methods of constructing and searching the virtual library and obtaining selected subsets of molecules with specified characteristics.

Thus, while this invention has been particularly described with reference to the drug lead identification art, it is clear that the validation of molecular structural descriptors and their use in selecting structurally diverse sets of chemical compounds can be applied anywhere a large number of compounds is encountered from which a representative subset is desired. Since the implications and advances in the art provided by the methods of this invention are still so new, the entire range of possible uses for the methods of this invention can not be fully described at the present time. However, such as yet identified uses are considered to fall under the teachings and claims of this invention if validated molecular structural descriptors are employed to characterize the diversity of molecules.

References Cited

1. Seligmann, B. (1995) *Synthesis, Screening, Identification of Positive Compounds and Optimization of Leads from Combinatorial Libraries: Validation of Success*, p. 69–70. Symposium: "Exploiting Molecular Diversity: Small Molecule Libraries for Drug Discovery", La Jolla, Calif. Jan. 23–25, 1995 [conference summary available from Wendy Warr & Associates, 6 Berwick Court, Cheshire, UK CW4 7HZ]
2. Johnson, M. and Maggiora, G. (Editors) *Concepts and Applications of Molecular Similarity*, John Wiley, New York, 1990
3. Martin, E., Blaney, J., Siani, M., Spellmeyer, D., Wong, A., and Moos, W. (1995) *Measuring Diversity: Experimental Design of Combinatorial Libraries for Drug Discovery*. J. Med. Chem. 38, 1431–1436
4. Martin, E., Blaney, J., Siani, M. and Spellmeyer, D. (1995) *Measuring diversity: Experimental design of combinatorial libraries for drug discovery*. Abstract, ACS Meeting, Anaheim, Calif. COMP 32, and Martin, E. (1995) *Measuring Chemical Diversity: Random Screening or Rationale Library Design*, p. 27–30. Symposium: "Exploiting Molecular Diversity: Small Molecule Libraries for Drug Discovery", La Jolla, Calif. Jan. 23–25, 1995 [conference summary available from Wendy Warr & Associates, 6 Berwick Court, Cheshire, UK CW4 7HZ]
5. Brown, R., Bures, M., and Martin, Y. (1995) *Similarity and cluster analysis applied to molecular diversity*. Abstract, ACS Meeting, Anaheim, Calif. COMP 3
6. Herndon, W. (1995). *Similarity and Dissimilarity of Molecular Structures*. p. 25–27. Symposium: "Exploiting Molecular Diversity: Small Molecule Libraries for Drug Discovery", La Jolla, Calif. Jan. 23–25, 1995 [conference summary available from Wendy Warr & Associates, 6 Berwick Court, Cheshire, UK CW4 7HZ]
7. Chapman, D. and Ross, M. (1994) Poster at the symposium: "Chemical and Biomolecular Diversity", San Diego, Calif. Dec. 14–16, 1994, and Ross, M. (1995) *Assessing Diversity (Or Lack Of It) in Chemical Libraries*. p. 63–65. Symposium: "Exploiting Molecular Diversity: Small Molecule Libraries for Drug Discovery", La Jolla, Calif. Jan. 23–25, 1995 [conference summary available from Wendy Warr & Associates, 6 Berwick Court, Cheshire, UK CW4 7HZ]
8. Cramer, R., Redl, G., and Berkoff, C. (1974) *Substructural Analysis: A Novel Approach to the Problem of Drug Design*. J. Med. Chem. 17, 533
9. U.S. Pat. No. 5,025,388 (1988) and Cramer, Patterson, D., and Bunce, J. (1988) Comparative Molecular Field Analysis (CoMFA). Effect of Shape on Binding of Steroids to Carrier Proteins. J. Am Chem. Soc. 110, 5959–5967
10. Kubinyi, H. Editor (1993) *3D QSAR in Drug Design, Theory, Methods, and Applications*. ESCOM, Leiden, Holland
11. Dean, P. Editor (1995) *Molecular Similarity in Drug Design*. Chapter 12, Kim, K. *Comparative molecular field analysis* (ComFA). p. 291–324. Chapman & Hill, London, UK
12. Y. Martin, M. Bures, E. Danaher, J. DeLazzer, I. Lico, P. Pavlik (1993) *A Fast Approach to Pharmacophore Mapping and its Application to Dopaminergic and Benziodiazepine Agonists*. J. Comp.-Aid. Mol. Des. 7, 83–102
13. P. Willett, V. Winterman (1986) *A comparison of some measures for the determination of intermolecular structural similarity*. Quantitative Structure-Activity Relationships 5, 18–23
14. R. P. Sheridan, R. B. Nachbar, B. L. Bush (1994) *Extending the trend vector: The trend matrix and sample-based partial least squares*. J. Comp.-Aid. Mol. Des. 8, 323–340
15. G. Moreau, P. Broto (1980) (no title given). Nouv. J. Chim. 4, 757–7644
16. L. B. Kier, L. H. Hall (1976) *Molecular Connectivity in Chemistry and Drug Research*. Academic Press, NY
17. Georges Lauri, Paul A. Bartlett (1994) *CAVEAT: A Program to Facilitate the Design of Organic Molecules*. J. Comp.-Aid. Mol. Des. 8, 51–66

What is claimed is:

1. A computer-based method for generating a virtual library of component parts and their characteristics in which all possible product molecules combinatorially derived from the component parts can be searched, without the necessity of generating the product structures during the search, for product molecules having desired properties by searching through only a combination of the descriptore of the component parts of the product molecules comprising the following steps:
   a. defining chemical transformations and reagents and cores to be used to specify possible product molecules; and
   b. using appropriate molecular descriptors, validated as possessing a neighborhood property, to precalculate characteristics of the component parts of all possible product molecules.

2. The method of claim 1 further comprising a computer-based method for selecting from the virtual library, for all possible product molecules which could be created by all combinatorial arrangements of specified reagents and cores, a subset of product molecules, comprising the following additional step:
   c. selecting a subset by summing the characteristics of the component parts for each possible product molecule derived from one or more cores and selected reagents and selecting for inclusion in the subset all those product molecules whose sum of component part characteristics does not fall with a chosen neighborhood distance of any other product molecule.

3. A computer-based method for generating and searching a virtual library of structural variations, cores, and their associated molecular structural descriptors, which can be searched for product molecules, derived from the combinatorial assembly of the structural variations and cores, having a high probability of sharing an activity possessed by a molecule of interest not known to be derived from a combinatorial reaction if the descriptor values of the molecules are within the neighborhood distance of the descriptor values of the molecule of interest, without the necessity of generating the product structures during the search, comprising the following steps:
   a. generating a virtual library by:
      (1). creating one or more files identifying one or more combinatorial reactions for one or more core structures;
      (2). creating separate structural variation files, associated with the reaction identifying files, in which are listed together the structural variations representative of those reactants which will react at each variation site of each combinatorial reaction;

(3). associating with each structural variation, data, characterizing each structural variation including:
   (a) characterizing data, which has not been derived from applying at least one molecular structural descriptor, validated as possessing a neighborhood property, to the structural variations, taking into account the structures of the cores with which the structural variations would be combined in the combinatorial syntheses; and
   (b) characterizing data which has been derived from applying at least one molecular structural descriptor, validated as possessing a neighborhood property, to the structural variations taking into account to the extent appropriate for application of the descriptor the structures of the cores with which the structural variations would be combined in the combinatorial syntheses;
(4). associating with each core, data, characterizing each core including:
   (a). characterization data which has not been derived from application of molecular descriptors, validated as possessing a neighborhood property; and
   (b). characterizing data which is derived from the following additional steps:
      (i). selecting a first core;
      (ii). selecting an attachment bond on the core;
      (iii). topomerically aligning the core;
      (iv). characterizing the core with CoMFA fields and the coordinates of the end points of the other attachment bonds;
      (v). repeating steps (ii) through (iv) for all attachment bonds on the core;
      (vi). selecting a next core; and
      (vii). repeating steps (ii) through (vi) for all cores;

b. fragmenting the molecule of interest as described in a fragmentation table;
c. selecting a fragmentation pattern;
d. aligning the fragments according to topomeric alignment rules;
e. generating CoMFA fields for each aligned fragment;
f. identifing whether the fragmentation pattern generated a core, and, if so, implementing the following steps:
   (1). selecting an attachment bond on the core;
   (2). topomerically aligning the core;
   (3). characterizing the core with CoMFA fields and coordinates of end points of the other attachment bonds;
   (4). repeating steps (1) through (3) for all attachment bonds on the core;
   (5). calculating the differences in CoMFA fields and differences in attachment bond coordinates for all attachment bond orientations;
g. identifying which reaction types within the virtual library correspond to the reaction type resulting from the fragmentation;
h. selecting any of the corresponding reaction types in the virtual library identified in step g;
i. if the fragmentation pattern generated a core, determining acceptable cores from the reaction type in the virtual library selected in step h by the following steps:
   (1). selecting any core from the virtual library;
   (2). generating a list of all the possible ways the attachment bonds in the virtual library core correspond to the attachment bonds in the fragmentation core by the following steps:
      (a). selecting a corresponding way;
      (b). determining the root sum of squared differences in attachment bond coordinates over all attachment bonds and of CoMFA field values;
      (c). if the difference determined in step (b) is greater than a chosen neighborhood value, delete the corresponding way from the list;
      (d). repeat steps (a) through (c) for all corresponding ways;
   (3). repeat steps (1) through (2) until a core is found with at least one corresponding way;
j. selecting the structural variations matching the reaction type in step h which were used in generating the virtual library;
k. selecting and outputting the combinations of structural variations which yield a product molecule falling within a chosen neighborhood value by the following steps:
   (1). selecting any combination of structural variations;
   (2). selecting a way in which the combination of structural variations may correspond to the fragments generated in step d;
   (3). if the fragmentation pattern generated a core and the correspondence of step (2) is not on the list generated in step i, proceed to step k.(7);
   (4). determining the root sum of squared differences between the CoMFA fields for the selected correspondence and combination of structural variations and the fields generated in step e;
   (5). if the fragmentation pattern generated a core, adding to the root sum determined in step k.(4) the root sum determined in step i.(2)(b);
   (6). if the total of the root sums determined in step (5) is less than a chosen neighborhood value, output the selected combination of structural variations, with the core, if any, and proceed to step k.(8);
   (7). repeat steps k.(2) through k.(6) until either the combination of structural variations has been output in step k.(6) or until no more possible correspondences remain;
l. if the fragmentation pattern generated a core, repeat steps i through k until all cores in the matching reaction type of the virtual library have been considered;
m. repeat steps h through l until all matching reaction types in the virtual library have been considered;
n. repeat steps c through m until all fragmentation patterns in the table have been considered.

4. A computer-based method for identifying from a virtual library of structural variations, cores, and their associated molecular structural descriptors, which can be searched for product molecules derived from the combinatorial assembly of the structural variations and cores, those molecules having a high probability of sharing an activity possessed by a molecule of interest of unknown synthetic pathway, if the descriptor values of the molecules are within the neighborhood distance of the descriptor values of the molecule of interest, comprising the following steps:
   a. fragmenting the query molecule as described in a fragmentation table;
   b. by using molecular structural descriptors, validated as possessing a neighborhood property, with which the virtual library was generated, generating the descriptor values for each fragment; and
   c. searching the virtual library for structural variations whose descriptor values fall within the neighborhood distance of the descriptor values for each fragment and identifying all possible combinatorial product molecules which could result from the specified structural variations.

5. The method of claim 4 in which the molecular structural descriptor validated as possessing a neighborhood property, appropiate to structural variations, is a topomeric CoMFA field.

6. The computer-based method of claim 4 further comprising after step c the following additional steps:
   d. selecting from all possible combinatorial product molecules a product molecule for inclusion in the subset;
   e. by using a molecular descriptor, validated as possessing a neighborhood property, appropriate to whole molecules with which the virtual library was generated:
      (1). generating representative descriptors for all product molecules including the selected molecule; and
      (2). removing from the set of all remaining product molecules those molecules whose descriptor values fall within a chosen neighborhood distance of the descriptor values of the selected molecule;
   f. by using a molecular descriptor, validated as possessing a neighborhood property, appropriate to the structural variations with which the virtual library was generated, removing from the set of all remaining product molecules those molecules formed from structural variations whose descriptor values fall within a chosen neighborhood distance of the descriptor values of the structural variations of the selected molecule;
   g. selecting from the set of all product molecules remaining after step f a product molecule for inclusion in the subset;
   h. repeating steps e through g until no additional product molecules remain to be selected in step g; and
   i. outputting a list of the selected subset and/or the structural variations from which the subset can be formed.

7. A computer-based method for generating a virtual library of structural variations, cores, and their associated molecular structural descriptors, which can be searched for product molecules derived from the combinatorial assembly of the structural variations and cores having desired properties, by combining descriptors of the structural variations and cores to generate descriptors representative of the product molecules, without the necessity of generating the product structures during the search, comprising the following steps:
   a. creating one or more files identifying one or more combinatorial reactions for one or more core structures;
   b. creating separate structural variation files, associated with the reaction identifying files, in which are listed together the structural variations representative of those reactants which will react at each variation site of each combinatorial reaction;
   c. associating with each structural variation, data, characterizing each structural variation including:
      (1) characterizing data, which has not been derived from applying at least one molecular structural descriptor, validated as possessing a neighborhood property, to the structural variations, taking into account the structures of the cores with which the structural variations would be combined in the combinatorial syntheses; and
      (2) characterizing data which has been derived from applying at least one molecular structural descriptor, validated as possessing a neighborhood property, to the structural variations taking into account to the extent appropriate for application of the descriptor the structures of the cores with which the structural variations would be combined in the combinatorial syntheses.

8. The method of claim 7 in which the molecular structural descriptor, validated as possessing a neighborhood property, appropriate to structural variations is a topomeric CoMFA field.

9. The method of claim 8 in which topomeric hydrogen bond fields are used in conjunction with the topomeric CoMFA descriptor.

10. The method of claim 7 in which the molecular structural descriptor, validated as possessing a neighborhood property, appropriate to structural variations is the Tanimoto 2D coefficient.

11. The method of claim 7 further comprising a computer-based method for selecting from the virtual library, for all possible product molecules which could be created by all combinatorial arrangements of specified structural variations and a common core molecule, a subset of product molecules, comprising the following additional steps:
   d. identifying all possible combinatorial product molecules which could result from the specified structural variations and selected core molecule;
   e. selecting from all possible combinatorial product molecules a product molecule for inclusion in the subset;
   f. by using a molecular descriptor, validated as possessing a neighborhood property, appropriate to whole molecules with which the virtual library was generated:
      (1). generating representative descriptors for all product molecules including the selected molecule; and
      (2). removing from the set of all remaining product molecules those molecules whose descriptor values fall within a chosen neighborhood distance of the descriptor values of the selected molecule;
   g. by using a molecular descriptor, validated as possessing a neighborhood property, appropriate to the structural variations with which the virtual library was generated, removing from the set of all remaining product molecules those molecules formed from structural variations whose descriptor values fall within a chosen neighborhood distance of the descriptor values of the structural variations of the selected molecule;
   h. selecting from the set of all product molecules remaining after step g a product molecule for inclusion in the subset;
   i. repeating steps f through h until no additional product molecules remain to be selected in step h; and
   j. outputting a list of the selected subset and/or the structural variations from which the subset can be formed.

12. The method of claim 11 in which the molecular structural descriptor, validated as possessing a neighborhood property, appropriate to whole molecules is the Tanimoto 2D coefficient.

13. The method of claim 11 in which the additional step f is performed immediately after the step of using a molecular descriptor, validated as possessing a neighborhood property, appropriate to whole molecules and further in which step g' is performed immediately after the step of using a molecular descriptor, validated as possessing a neighborhood property, appropriate to structural variations:
   f'. repeating the previous step for another molecular descriptor, validated as possessing a neighborhood property, appropriate to whole molecules with which the virtual library was generated until no additional whole molecule descriptor, validated as possessing a neighborhood property, remains to be used;
   g'. repeating the previous step for another molecular descriptor, validated as possessing a neighborhood property, appropriate to structural variations with which the virtual library was generated until no additional structural variation descriptor, validated as possessing a neighborhood property, remains to be used.

14. The method of claim 11 in which the molecular structural descriptor, validated as possessing a neighborhood property, appropriate to structural variations is a topomeric CoMFA field.

15. The method of claim 14 in which topomeric hydrogen bond fields are used in conjunction with the topomeric CoMFA descriptor.

16. The method of claim 7 further comprising a computer-based method for selecting from the virtual library, for all possible product molecules which could be created by all combinatorial arrangements of specified structural variations and core molecules, a subset of product molecules, comprising the following additional steps:
   d. selecting from all possible cores a core upon which to base the subset;
   e. by using a molecular descriptor, validated as possessing a neighborhood property, appropriate to cores:
      (1). generating descriptors for all cores including the selected core; and
      (2). selecting from the set of all possible cores those core molecules whose descriptor values fall within a chosen neighborhood distance of the descriptor values of the selected core molecule;
   f. identifying all possible combinatorial product molecules which could result from the specified structural variations and selected core molecules;
   g. selecting from all possible combinatorial product molecules a product molecule for inclusion in the subset;
   h. by using a molecular descriptor, validated as possessing a neighborhood property, appropriate to whole molecules with which the virtual library was generated:
      (1). generating representative descriptors for all product molecules including the selected molecule; and
      (2). removing from the set of all remaining product molecules those molecules whose descriptor values fall within a chosen neighborhood distance of the descriptor values of the selected molecule;
   i. by using a molecular descriptor, validated as possessing a neighborhood property, appropriate to the structural variations with which the virtual library was generated, removing from the set of all remaining product molecules those molecules formed from structural variations whose descriptor values fall within a chosen neighborhood distance of the descriptor values of the structural variations of the selected molecule;
   j. selecting from the set of all product molecules remaining after step i a product molecule for inclusion in the subset;
   k. repeating steps h through j until no additional product molecules remain to be selected in step j; and
   l. outputting a list of the selected subset and/or the structural variations and cores from which the subset can be formed.

17. The method of claim 16 in which the molecular structural descriptor, validated as possessing a neighborhood property, appropriate to structural variations is a topomeric CoMFA field.

18. The method of claim 17 in which topomeric hydrogen bond fields are used in conjunction with the topomeric CoMFA descriptor.

19. The method of claim 16 in which the molecular structural descriptor, validated as possessing a neighborhood property, appropriate to whole molecules is the Tanimoto 2D coefficient.

20. The method of claim 7 further comprising a computer-based method for selecting from the virtual library, for all possible product molecules which could be created by all combinatorial arrangements of specified structural variations and a common core molecule, a subset of product molecules, comprising the following additional steps:
   d. identifying all possible combinatorial product molecules which could result from the specified structural variations and selected core molecule;
   e. selecting from all possible combinatorial product molecules a product molecule for inclusion in the subset;
   f. by using a molecular descriptor, validated as possessing a neighborhood property, appropriate to whole molecules with which the virtual library was generated,
      (1). generating representative descriptors for all product molecules including the selected molecule; and
      (2). removing from the set of all remaining product molecules those molecules whose descriptor values fall within a chosen neighborhood distance of the descriptor values of the selected molecule;
   g. selecting from the set of all product molecules remaining after step f a product molecule for inclusion in the subset;
   h. repeating steps f through g until no additional product molecules remain to be selected in step g; and
   i. outputting a list of the selected subset and/or the structural variations from which the subset can be formed.

21. The method of claim 20 in which the molecular structural descriptor, validated as possessing a neighborhood property, appropriate to whole molecules is the Tanimoto 2D coefficient.

22. The method of claim 7 further comprising a computer-based method for selecting from the virtual library, for all possible product molecules which could be created by all combinatorial arrangements of specified structural variations and a common core molecule, a subset of product molecules, comprising the following additional steps:
   d. identifying all possible combinatorial product molecules which could result from the specified structural variations and selected core molecule;
   e. selecting from all possible combinatorial product molecules a product molecule for inclusion in the subset;
   f. by using a molecular descriptor, validated as possessing a neighborhood property, appropriate to the structural variations with which the virtual library was generated, removing from the set of all remaining product molecules those molecules formed from structural variations whose descriptor values fall within a chosen neighborhood distance of the descriptor values of the structural variations of the selected molecule;
   g. selecting from the set of all product molecules remaining after step f a product molecule for inclusion in the subset;
   h. repeating steps f through g until no additional product molecules remain to be selected in step g; and
   i. outputting a list of the selected subset and/or the structural variations from which the subset can be formed.

23. The method of claim 22 in which the molecular structural descriptor, validated as possessing a neighborhood property, appropriate to structural variations is a topomeric COMFA field.

24. The method of claim 23 in which topomeric hydrogen bond fields are used in conjunction with the topomeric CoMFA descriptor.

25. The method of claim 7 further comprising a method of determining within the virtual library the molecules which could be created by all combinatorial arrangements of specified structural variations and a common core molecule which have a high probability of sharing an activity possessed by a molecule of interest if the descriptor values of the molecules are within the neighborhood distance of the descriptor values of the molecule of interest, comprising the following additional steps:
    d. identifying in the virtual library all possible combinatorial product molecules which could result from the specified structural variations and selected core molecule;
    e. generating representative descriptors for all product molecules and the molecule of interest with a molecular structural descriptor, validated as possessing a neighborhood property, appropriate to whole molecules with which the virtual library was generated;
    f. using the same molecular descriptor, validated as possessing a neighborhood property, appropriate to whole molecules, selecting the set of all product molecules whose descriptor values fall within a chosen neighborhood distance of the descriptor values of the selected molecule; and
    g. outputting a list of the selected subset and/or the structural variations from which the subset can be formed.

26. The method of claim 25 in which the molecular structural descriptor, validated as possessing a neighborhood property, appropriate to whole molecules is the Tanimoto 2D coefficient.

27. The method of claim 7 further comprising a method of determining within the virtual library the molecules which could be created by all combinatorial arrangements of specified structural variations and a common core molecule which have a high probability of sharing an activity possessed by a molecule of interest if the descriptor values of the molecules are within the neighborhood distance of the descriptor values of the molecule of interest, comprising the following additional steps:
    d. identifying in the virtual library all possible combinatorial product molecules which could result from the specified structural variations and selected core molecule;
    e. characterizing the molecule of interest with a molecular structural descriptor, validated as possessing a neighborhood property, appropriate to structural variations with which the virtual library was generated;
    f. using the same molecular descriptor, validated as possessing a neighborhood property, appropriate to structural variations, selecting the set of all product molecules formed from structural variations whose descriptor values fall within a chosen neighborhood distance of the descriptor values of the structural variations of the selected molecule; and
    g. outputting a list of the selected subset and/or the structural variations from which the subset can be formed.

28. The method of claim 27 in which the molecular structural descriptor, validated as possessing a neighborhood property, appropriate to structural variations is a topomeric COMFA field.

29. The method of claim 28 in which topomeric hydrogen bond fields are used in conjunction with the topomeric CoMFA descriptor.

30. The method of claim 7 further comprising a method of determining within the virtual library the molecules which could be created by all combinatorial arrangements of specified structural variations and a common core molecule which have a high probability of sharing an activity possessed by a molecule of interest if the descriptor values of the molecules are with a chosen neighborhood distance of the descriptor valued of the molecule of interest, comprising the following additional steps:
    d. identifying in the virtual library all possible combinatorial product molecules which could result from the specified structural variations and selected core molecule;
    e. generating representative descriptors for the molecule of interest with both a molecular structural descriptor, validated as possessing a neighborhood property, appropriate to whole molecules with which the virtual library was generated and with a molecular structural descriptor, validated as possessing a neighborhood property, appropriate to structural variations with which the virtual library was generated;
    f. by using the same molecular descriptor, validated as possessing a neighborhood property, appropriate to whole molecules, selecting the set of all product molecules whose descriptor values fall within a chosen neighborhood distance of the descriptor values of the selected molecule, and by using the same molecular descriptor, validated as possessing a neighborhood property, appropriate to structural variations, selecting the set of all possible molecules formed from structural variations whose descriptor values fall within a chosen neighborhood distance of the descriptor values of the structural variations of the selected molecule; and
    g. outputting a list of the selected subset and/or the structural variations from which the subset can be formed.

31. The method of claim 30 in which the molecular structural descriptor, validated as possessing a neighborhood property, appropriate to structural variations is a topomeric CoMFA field.

32. The method of claim 31 in which topomeric hydrogen bond fields are used in conjunction with the topomeric CoMFA descriptor.

33. The method of claim 30 in which the molecular structural descriptor, validated as possessing a neighborhood property, appropriate to structural variations is the Tanimoto 2D coefficient.

34. The method of claim 7 further comprising a method of determining within the virtual library the molecules which could be created by all combinatorial arrangements of specified structural variations and core molecules which have a high probability of sharing an activity possessed by a molecule of interest if the descriptor values of the molecules are within the neighborhood distance of the descriptor values of the molecule of interest, comprising the following additional steps:
    d. selecting from all possible cores a core upon which to base the subset;
    e. by using a molecular descriptor, validated as possessing a neighborhood property, appropriate to cores:
        (1). generating descriptors for all cores including the selected core; and
        (2). selecting from the set of all possible cores those core molecules whose descriptor values fall within a chosen neighborhood distance of the descriptor values of the selected core molecule;
    f. identifying all possible combinatorial product molecules which could result from the specified structural variations and selected core molecules;

g. generating representative descriptors for all product molecules and the molecule of interest with a molecular structural descriptor, validated as possessing a neighborhood property, appropriate to whole molecules with which the virtual library was generated;

h. by using the same molecular descriptor, validated as possessing a neighborhood property, appropriate to whole molecules, selecting the set of all product molecules whose descriptor values fall within a chosen neighborhood distance of the descriptor values of the selected molecule; and i. outputting a list of the selected subset and/or the structural variations from which the subset can be formed.

35. The method of claim 34 in which the molecular structural descriptor, validated as possessing a neighborhood property, appropriate to structural variations is the Tanimoto 2D coefficient.

36. The method for generating a virtual library of molecules of claim 7 in which the following additional step is performed immediately after the steps of associating with each structural variation, data characterizing each structural variation:

d. associating with each core, data characterizing each core including:
  (1). characterizing data which has not been derived from application of molecular descriptors, validated as possessing a neighborhood property; and
  (2). characterizing data which is derived by the following additional steps:
    (a). selecting a first core;
    (b). selecting an attachment bond on the core;
    (c). topomerically aligning the core;
    (d). characterizing the core with CoMFA fields and the coordinates of the end points of the other attachment bonds;
    (e). repeating steps (b) through (d) for all attachment bonds on the core;
    (f). selecting a next core; and
    (g). repeating steps (b) through (f) for all cores.

37. The method of claims 11 or 16 or 20 or 25 or 30 or 34 in which the following additional step is performed immediately after the step of using a molecular descriptor, validated as possessing a neighborhood property, appropriate to whole molecules:

repeating the previous step for another molecular descriptor, validated as possessing a neighborhood property, appropriate to whole molecules with which the virtual library was generated until no additional whole molecule descriptor, validated as possessing a neighborhood property, remains to be used.

38. The method of claims 11 or 16 or 22 or 27 or 30 in which the following additional step is performed immediately after the step of using a molecular descriptor, validated as possessing a neighborhood property, appropriate to structural variations:

repeating the previous step for another molecular descriptor, validated as possessing a neighborhood property, appropriate to structural variations with which the virtual library was generated until no additional structural variation descriptor, validated as possessing a neighborhood property, remains to be used.

* * * * *